(12) United States Patent
Yager et al.

(10) Patent No.: US 6,180,114 B1
(45) Date of Patent: Jan. 30, 2001

(54) THERAPEUTIC DELIVERY USING COMPOUNDS SELF-ASSEMBLED INTO HIGH AXIAL RATIO MICROSTRUCTURES

(75) Inventors: Paul Yager; Michael H. Gelb; Anatoly N. Lukyanov; Alex S. Goldstein, all of Seattle; Mary L. Disis, Renton, all of WA (US)

(73) Assignee: University of Washington, Seattle, WA (US)

( * ) Notice: Under 35 U.S.C. 154(b), the term of this patent shall be extended for 0 days.

(21) Appl. No.: 09/219,057

(22) Filed: Dec. 22, 1998

Related U.S. Application Data

(63) Continuation-in-part of application No. 08/752,848, filed on Nov. 21, 1996, now Pat. No. 5,851,536.
(60) Provisional application No. 60/087,179, filed on May 29, 1998.

(51) Int. Cl.$^7$ ............................... A61K 9/00; A61K 9/127

(52) U.S. Cl. ..................... 424/400; 424/450; 424/409; 514/44; 935/54

(58) Field of Search .................................. 424/400, 450, 424/443, 1.21, 9.321, 9.51, 417, 94.3; 428/357, 221; 935/54; 514/44

(56) References Cited

U.S. PATENT DOCUMENTS

| | | | |
|---|---|---|---|
| 4,871,488 | * 10/1989 | Mannino | 264/4.6 |
| 4,990,291 | * 2/1991 | Schoen | 264/4.7 |
| 5,004,566 | 4/1991 | Schnur et al. | . |
| 5,643,574 | * 7/1997 | Gould-Fogerite | 424/181.1 |
| 5,851,536 | * 12/1998 | Yager | 424/400 |

FOREIGN PATENT DOCUMENTS

WO 96/25942  8/1996  (WO) .

OTHER PUBLICATIONS

Torchilin in BBRC. 85, #3, p. 983–990, Dec. 1978.

Spargo, Barry, J. et al. "Technological development of lipid–based microcylinders: biocompatibility and controlled release" Chemical Abstract, vol. 119, No. 14 (Oct. 1993).

Archibald, Douglas Dean et al. "Structural studies of lipid fibers formed by sphingosine" Biochim. Biophys, Acta, (1993), 1166, pp. 154–162.

Itojima, Yukiko et al. "Spontaneous formation of helical structures from phospholipid–nucleoside conjugates" Biochemistry (1992), 31(20), 4757–65.

Hartgerink, Jeffrey D. et al. "Self assembling organic nanotubes" Chemical Abstracts, vol. 126, Columbus, Ohio.

(List continued on next page.)

Primary Examiner—Gollamudi S. Kishore
(74) Attorney, Agent, or Firm—Klarquist Sparkman Campbell Leigh & Whinston, LLP

(57) ABSTRACT

Therapeutic complexes comprising plural therapeutic compounds self assembled into high axial ratio microstructures are described. The therapeutic complexes satisfy the formula HARM-Th, wherein HARM is a high axial ratio forming material and Th is a therapeutic coupled to or associated with the HARM. The therapeutic complexes also can satisfy the formula HARM-S-Th, wherein S is a spacer. Release of the therapeutic by the complex generally follows either 0-order kinetics or psuedo-first order kinetics. A method for delivering therapeutics to oransims, particularly humans, also is described. The method comprises administering an effective amount of (1) a ligand, such as a therapeutic, self-assembled into a HAR microstructure, or (2) a ligand, such as a therapeutic, coupled to or associated with a material capable of thereafter self-assembling into a high axial ratio microstructure, to the mammal. Nucleic acids are an example of a ligand that can be administered effectively according to this method through noncovalent attachment to the HARM-forming materials.

71 Claims, 12 Drawing Sheets

OTHER PUBLICATIONS

Price, R. et al., "Controlled release from cylindrical microstructures" Journal of Microencapsulation, vol. 8, No. 3, Jul. 1, 1991, pp. 301–306.

Itojima, Yukiki et al., "Helical structures of nucleic acid—lipid conjugates: formation and murphology of helical structures from dimyristoyl–5'–phosphatidylribonucleosides" Nucleic Acids Symp. Ser. (1990), 22.

J.M. Schnur et al., "Development of self–assembled lipid microcylinders for controlled release applications" Pharm. News (Langhorne, PA) (1995), 2(1), 10–15.

Archibald, Douglas D. and Yager, Paul, "Microstructural Polymorphism in Bovine Brain Galactocerebroside and Its Two Major Subfractions," American Chemical Society, *Biochemistry*, vol. 31, No. 37, (1992).

Spargo, B.J. et al., "Controlled Release of Transforming Growth Factor–β from Lipid–Based Microcylinders," J. Microencapsulation, vol. 12, No. 3, 247–254 (1995).

Torchilin BBRC. 85 #3 p. 983–990, 1978.*

* cited by examiner

DRUG MOEITY

LINKER (IF REQUIRED)

CHIRAL HEADGROUP

HYDROCARBON CHAINS

THERAPEUTIC DELIVERY USING COMPOUNDS SELF-ASSEMBLED INTO HIGH AXIAL RATIO MICROSTRUCTURES

CROSS REFERENCE TO RELATED APPLICATION

This application is a continuation-in-part of U.S. patent application Ser. No. 08/752,848, filed on Nov. 21, 1996, now U.S. Pat. No. 5,851,536, and further claims priority from copending U.S. provisional patent application, Ser. No. 60/087,179, filed on May 29, 1998, both of which are incorporated herein by reference.

FIELD OF THE INVENTION

The present invention concerns compounds, compositions and methods useful for delivering therapeutics.

BACKGROUND OF THE INVENTION

Two current issues in drug delivery concern the spatial and temporal attributes of therapeutic delivery systems. Targeting the therapeutic to limit its exposure to the desired site of action is the spatial aspect. Controlling the delivery of the therapeutic over time is the temporal aspect. Continuous drug release often is preferable to periodically administering bolus doses to the entire organism. Bolus administration results in a spike of drug concentration, followed by a decrease in concentration to baseline.

Moreover, patients often fail to comply with bolus drug administration procedures, one example being outpatients who do not complete their course of antibiotics. This is a key problem in controlling emerging drug-resistant strains of tuberculosis, and is probably a factor contributing to an increase in the appearance of many other drug-resistant strains of bacteria. The cost in morbidity and mortality from inadequate frequency of dosing with insulin is known to be in the billions of dollars in the United States alone. Reach et al.'s *Can Continuous Glucose Monitoring be used for the Treatment of Diabetes,* 64:381A-386A (Analytical Chemistry, 1992). Restricting ambulatory patients to a hospital setting to insure compliance (or establishing some other system of enforced compliance) is not a practical solution. Patient noncompliance with bolus administration procedures therefore is an important impetus for developing continuous drug delivery systems.

At present there are several approaches to controlled or continuous drug delivery, some of which are still in the research phases, and some of which have been successfully used in commercial products for some time. Prevost et al.'s *New Methods of Drug Delivery,* 249:1527–1533 (Science, 1990). The delivery approaches include: (1) external delivery systems, such as external mechanical pumps and osmotic patches; (2) internal osmotic pumps; and (3) implantable or ingestible polymeric structures that can include erodible hydrogels. With pumps, continuous release can be set by the pump design or by controlling the motor. Continuous drug delivery using continuous infusion with an i.v. line (the only viable method for some chemotherapeutic drugs) is costly and restricts the patient's movement. Implanted catheters and pumps are an expensive solution, the considerable risk of which is only balanced by the importance of continuous delivery of the drug in question. Using implantable macroscopic devices for drug delivery restricts the site of delivery to one that can accommodate the object. The NORPLANT® contraceptive system, effective though it is, requires a large insertion site and must be surgically recovered after use.

With polymeric structures the rate of delivery can be controlled by the shape and permeability-erodability of the polymer. Dermal patches are very simple and relatively noninvasive. However, dermal patches have been effective only for a few drugs that are relatively permeant through the skin.

Some of the approaches discussed above work well for some classes of drugs, and are inapplicable to others. The chemically labile nature of peptide drugs, for example, results in their incompatibility with many polymeric delivery systems. Those polymers in which they can be immobilized have yet to be approved for general use. And, the common feature of all the existing delivery systems listed above is that they control diffusion or effusion by a macroscopic mechanical object. This limits their usefulness and makes using the delivery systems a nuisance and perhaps even requires invasive surgical implanting.

Drug distribution can be controlled by the microstructures into which the drug self-assembles. Liposomes are one example of a self-assembled microstructure, and encapsulating drugs in liposomes has proven useful in some circumstances. Ostro, *Liposomes: From Biophysics to Therapeutics,* Marcel Dekker, Inc. (1987). For instance, liposomes can be used to deliver drugs to skin. Yager et al's *Conjugation of Phosphatidyl-ethanolamine to poly(n-isopropylacrylamide) for Potential Use in Liposomal Drug Delivery Systems,* 33:4659–4662 (Polymer, 1992). Phosphatidylglycerols have been modified with a wide range of peptide and non-peptide drugs (in particular AZT) with the assumption that they would self-assemble into liposomes, and would be trapped by macrophages in the reticuloendothelial system after injection into the bloodstream. Wang et al.'s *Synthesis of Phospholipid-Inhibitor Conjugates by Enzymatic Transphospha-tidylations with Phospholipase D,* 115:10487–10491 (J. Am. Chem. Soc., 1993). Beyond the general assumption that liposomes would be formed, how hydrophobically modified drugs self-associate, and how the self-association affects the conformation of the drugs themselves, is largely unknown.

Lipid tubules are a recently discovered self-organizing system in which lipids crystallize into tightly packed bilayers that spontaneously form hollow cylinders less than 1 $\mu$m in diameter. The basic subunit of the tubule is a helical ribbon of lipid bilayer and, in some cases, open helical structures of the same diameter can be seen. In 1983, polymerizable diacetylenic phosphatidylcholines such as 1,2-di-(10,12-tricosadiynoyl)-sn-glycero-3-phosphocholine (referred to as $DC_{8,9}PC$) were discovered by Yager and Schoen to form novel hollow tubular microstructures. See, for instance, Yager et al.'s *Formation of Tubules by a Polymerizable Surfactant,* 106:371–381 (Mol. Cryst. Liq. Cryst., 1984). Diacetylenic lipid tubules are straight, rigid, about 0.75 $\mu$m in diameter, and can be made to range in length from a few pm to nearly 1 mm, depending on the conditions used to form the microstructure. Further, the walls of the tubules may be as thin as a single bilayer. The lumen (the open space in a tubular organ or device) is generally open, allowing free access by diffusion from the ends of the microstructures.

Kunitake et al. demonstrated that a positively charged chiral amphiphile based on glutamate forms structures similar to those formed by $DC_{8,9}PC$. Kunitake et al.'s *Helical Superstructures are Formed from Chiral Ammonium Bilayer Membranes,* 1709–1712 (Chem. Lett., 1984). Helices and tubules of much smaller diameters (~300 Å) were found by Yamada et al. to form from related synthetic two-chain amphiphiles with oligopeptides (such as 12–14-mers of glutamic and aspartic acid) as hydrophilic headgroups. Yamada et al.'s *Formation of Helical Super Structure from Single-Walled Bilayers by Amphiphiles with Oligo-L-Glutamic Acid-Head Group,* 10:1713–1716 (Chem. Lett., 1984). Yamada et al.'s *Amphiphiles with Polypeptide head Groups. 7. Relationship Between Formation of Helical Bilayer membranes and Chemical Structures of Dialkyl Amphiphiles with Polypeptide-Head Groups,* 48:327–334 (Kobunshi Ronbunshu, 1991). Recent work by Shimizu and Hato on similar lipids with polypeptide headgroups, including $(Pro)_3$-tripeptide, produced similar tubules and helices. Later studies by the Yamada group ascertained that both positive, negative and neutral amino acids could be incorporated into block copolymers as headgroups for glutamate-based lipopeptides.

However, fully charging the headgroups prevented tubule and helix formation. This is presumably because charging the polypeptide side chains increases the headgroup excluded volume to the point that close packing of the hydrocarbon chains is no longer possible in a planar bilayer. Further, there was evidence that the secondary structure of the polypeptide varied with the nature of the microstructure and that β-sheet formed between headgroup polypeptides.

It recently was determined that helical and tubular structures, as well as rod-like cochleate cylinders, can be formed quantitatively from the n-fatty acyl and α-hydroxy fatty acyl fractions of bovine brain galactocerebrosides, designated NFA-cer and HFA-cer, respectively. Yager et al.'s *Microstructural Polymorphism in Bovine Brain Galactocerebrosides and its Two Major Subfractions,* 31:9045–9055 (Biochem., 1992). Tubular and helical structures have now bee(n observed in samples of aged suspensions of saturated-chain phosphatidylcholines and as transient intermediates in the crystallization of cholesterol from mixed micellar suspensions. See, for instance, Konikoff et al.'s *Filamentous, Helical, and Tubular Microstructures During Cholesterol Crystallization from Bile,* 90:1155–1160 (J. Clin. Invest., 1992).

There appear to have been no commercialized uses for tubules to date. Lipid tubules have been "decorated" with inorganic materials, including metals [See, for instance, Schnur et al.'s U.S. Pat. No. 4,911,981, entitled Metal Clad Lipid Microstructures] and salts [Yager et al.'s *Formation of Mineral Microstructures with a High Aspect Ratio from Phospholipid Bilayer Tubules,* 11:633–636 (J. Mat. Sci. Lett., 1992), although a practical use for these materials has not yet been reported. Some preliminary work has been undertaken to use the lumen of diacetylenic lipid tubules as a reservoir for the encapsulation of drugs for delivery in wound dressings. See, for instance, Cliff et al.'s *The Use of Lipid Microcylinders as Release Vehicles; Release Rates of Growth Factors and Cytokines,* Fourth World Biomaterials Conference (1992). These procedures have yet to realize and exploit the beneficial physical characteristics of tubules.

There also are patented approaches to using cochleate cylinders as drug delivery systems. For example, Mannino et al. have used cochleates cylinders, formed by the addition of calcium ions to some negatively charged phopholipids, to encapsulate materials. See, for example, U.S. Pat. Nos. 4,663,161 and 4,871,488, and international patent application, No. PCT/US96/01704. Mannino's cochleate cylinders apparently undergo a transformation to a liposomal intermediate prior to drug release.

SUMMARY

The ligand delivery approach described herein is distinctly different, and potentially much more widely applicable, than any of the prior known methods for continuously delivering ligands, such as therapeutics. The invention provides ligand materials, which are themselves capable of forming high axial ratio microstructures, particularly tubules, cochleate cylinders, helical ribbons and twisted ribbons. Alternatively, compounds according to the formula

HARM-Lg are provided wherein "HARM" refers to molecules, e.g., lipid molecules, that are capable of self-assembling into high axial ratio microstructures. "Lg" is a ligand, such as a diagnostic or a therapeutic, coupled to or associated with the HARM. The ligand can be any agent now known or hereafter developed that does not interfere with the formation of high axial ratio (HAR) microstructures. By way of example, and without limitation, the Lg may be selected from the group consisting of peptides, nucleic acids, antigens and conventional pharmaceuticals.

Certain HARMs used for working embodiments of the invention satisfy the formula

$R_1R_2CH-X$ wherein $R_1$ and $R_2$ are alkyl, alkenyl (i.e., compounds that include at least one double bond), alkynyl (i.e., compounds that include at least one triple bond) or heteroalkyl, heteroalkenyl or heteroalkynyl chains having from about 10 to about 25 carbon atoms. Heteroalkyl, heteroalkenyl and heteroalkynyl compounds are compounds that include heteroatoms, such as, without limitation, nitrogen, oxygen and sulfur. X is a hydrophilic group. $R_1$ and $R_2$ preferably include at least one site of unsaturation, and generally are coupled to the carbon atom by functional groups that include heteroatoms, particularly but not necessarily, esters and amides. $R_1$ and $R_2$ also can be attached to a chiral carbon. Certain compounds according to this formula have been made wherein X is a polypeptide, such as polyglutamate or polyaspartate.

Moreover, spacers can be used to couple ligands to HARMs. One example, without limitation, of a class of suitable spacers are polypeptides that include enzyme cleavage sites, such as protease cleavage sites recognized by trypsin, trypsin-like enzymes and elastase.

Still another embodiment of the invention provides HARM-Lgs which generally satisfy *he formula

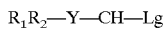

$R_1R_2-Y-CH-Lg$ wherein $R_1$ and $R_2$ are hydrophobic alkyl, alkenyl or alkynyl chains having from about 10 to about 25 carbon atoms, Y is selected from the group consisting of —CO—NH—, —NH—CO—, —O—CO—, and —CO—O—, and wherein Lg is selected from the group consisting of peptides, nucleic acids, antigens and conventional pharmaceuticals. $R_1$ and $R_2$ may both include at least one site of unsaturation.

The present invention also provides compositions useful for delivering ligands, such as therapeutic agents. The compositions comprise plural constituent molecules self-assembled into HAR microstructures. Each constituent molecule satisfies the formula

HARM-Lg as discussed above. The ligand may be coupled to the HARM using a spacer (S), i.e. HARM-S-Lg.

The compositions may self assemble so that only a portion of the plural constituent molecules have therapeutics coupled to HARMs. Moreover, the plural constituent molecules self-assembled into HAR microstructures can have plural different Ligands. The result is a microstructure having plural different ligands associated therewith.

The present invention also provides a method for delivering ligands, such as therapeutic agents, particularly in a steady, continuous manner. The method comprises administering to a person or animal effective amounts of compounds or compositions made in accordance with the present invention comprising plural constituent molecules self-assembled into HAR microstructures. The method can comprise administering effective amounts of compounds satisfying the formulas discussed above, including the use of spacers. The compounds or compositions may be administered by any number of methods including, but not limited to, topically, orally, such as in the case of vaccines, intramuscularly, intranasally, subcutaneously, intraperitoneally, intralesionally or intravenously. And, the compositions may further comprise conventional materials known in the pharmaceutical field, including materials selected from the group consisting of buffers, stabilizers, diluents and adjuvants.

Complexes comprising noncovalent association of ligands, such as nucleic acids, with HARM forming materials recently have proved important. A working embodiment comprises a complex self-assembled into high axial ratio microstructures, the complex satisfying the formula HARM-Lg. "HARM" is a high axial ratio microstructure forming material and Lg is a ligand, particularly a therapeutic, noncovalently associated with the high axial ratio microstructure forming material. The HARM is selected from the group consisting of tubules, cochleate cylinders, helical ribbons, twisted ribbons, and mixtures thereof. These complexes also can further comprise ligands covalently bonded to the high axial ratio microsrtucture forming material, ligands entrapped in the lumen of the high axial ratio micrstructure, or both.

Both nuclear and plasmid DNA have been administered in vivo using such complexes. For example, DNA vaccines have been administered to organisms. In these working embodiments, the high axial ratio microstructure forming material typically is selected from the group consisting of amino-acid based amphiphiles, phospholipid-based amphphiles, sphingosine-based amphiphiles, aldonamide-based amphiphiles, and mixtures thereof. Particular embodiments of these amphiphiles generally satisfy one of the following formulas:

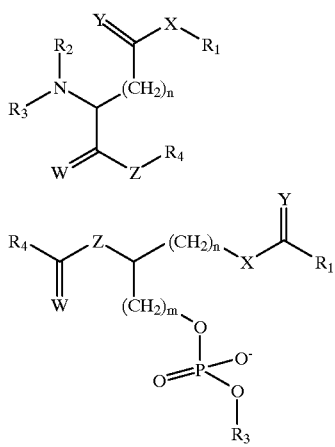

-continued

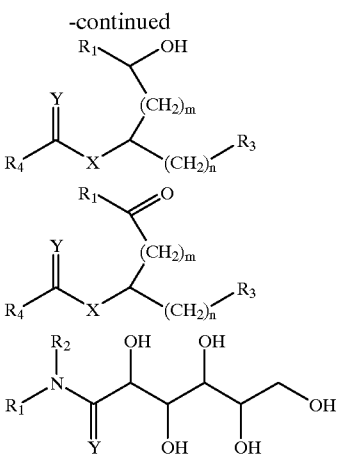

where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_2$ is H, $R_1$ or $R_4$, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, W is O or S, X is O, S, NH, $NR_1$, $NR_3$ or $NR_4$, Y is O or S, and Z is O, S, NH or $NR_1$.

A method for delivering ligands using such complexes also is provided by the present invention. A working embodiment of this method comprised first providing a complex having a high axial ratio microstructure. The complex comprised nuclear or plasmid DNA noncovalently associated with the high axial ratio microstructure forming material. An effective amount of this complex was then administered in vivo.

An object of the invention is to develop a device-free method by which ligands, such as drugs, can be released into the body, particularly in a continuous manner (0-order kinetics) through association with HARMs.

Another object of this invention is to form compounds and compositions comprising drugs or prodrugs associated with HARMs that continuously release drugs either through dissolution of the molecules from the ends of the microstructures or through enzymatic cleavage.

Still another object of the present invention concerns using a homogeneous population of HARMs to dissolve (or be enzymatically degraded) in such a manner that the rate of release of the constituent molecules (or parts thereof) is constant until the microstructures are consumed.

Still another object of the present invention is to ligate an appropriate hydrophobic anchoring moiety to water-soluble molecules and clinically significant therapeutics, such as conventional pharmaceuticals and bioactive polypeptides, and to allow such compounds to self-associate into HAR microstructures.

Still another object of the present invention is to provide compounds and compositions comprising therapeutics coupled to HARMs by spacers. A particularly suitable class of spacers are peptides or polypeptides (polypeptides are defined herein to mean an amino acid chain having at least two amino acids linked by amide bonds). Such spacers also can include enzyme recognition sites.

Still another object of the present invention is to provide materials and methods useful for oral delivery of materials to the gut, such as delivery of therapeutics and vaccines to the small intestine, wherein such materials are generally impervious to the low pH and proteolytic activity of the stomach.

DETAILED DESCRIPTION

The present invention provides ligands, and compositions comprising such ligands, particularly therapeutics, that are capable of self assembling into HAR microstructures. Alternatively, the ligand may be coupled to or associated with materials capable of forming HAR microstructures. "Coupled to or associated with" includes, but is not limited to, covalent bonding, hydrogen bonding, ionic bonding, electrostatic interactions, electron donor-acceptor interactions, etc. Nucleic acids, for example, have been electrostatically associated with HAR microstructures, including glutamic acid dialkyl amides, and these complexes have been used to deliver and protect (such as from nucleases) nuclear and plasmid DNA. The lipid structural components are generally intended to be completely metabolized into nontoxic products.

Figure 1:
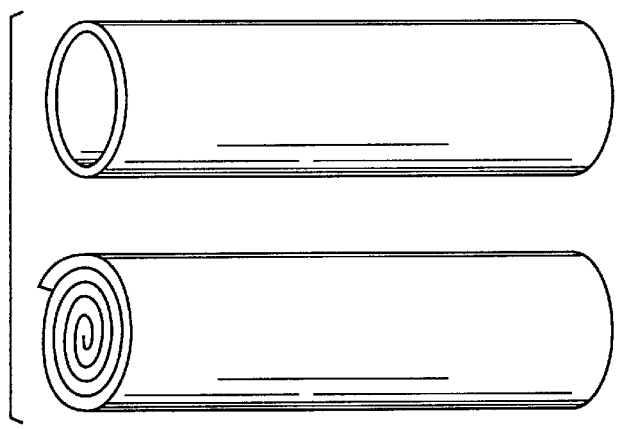
FIG. 1 is a schematic drawing illustrating non-liposomal microstructures of bilayer-forming amphiphiles.

As used herein, "HAR microstructure" refers to microstructures where the ratio of the major axes is from about 2 to 5,000, and more typically from about 2 to 1,000. For example, with an HFA-cerebroside cochleate cylinder having a diameter of about 0.1 μm, there are about 20 lipid bilayer "wraps" in the structure. This means that at the end of the cochleate cylinder there is about 3 μm of linear bilayer edge exposed. This cochleate cylinder would have an axial ratio of greater than 300 (30 μm in length divided by 0.1 μm in diameter=300). Examples, without limitation, of suitable HAR microstructures include tubules, cochleate cylinders, helical ribbons, twisted ribbons, and mixtures thereof. FIG. 1 provides a schematic representation of tubules and cochleate microstructures.

HARMs solve many continuous ligand delivery problems, and are useful for the continuous release of ligands. One reason for this is that the geometry of ligand particles affects the kinetics of ligand release. Moreover, the environment in which the compounds undergo hydrolysis or enzymatic cleavage also can effect the kinetics of the reaction. This is discussed in more detail below.

Figure 2:
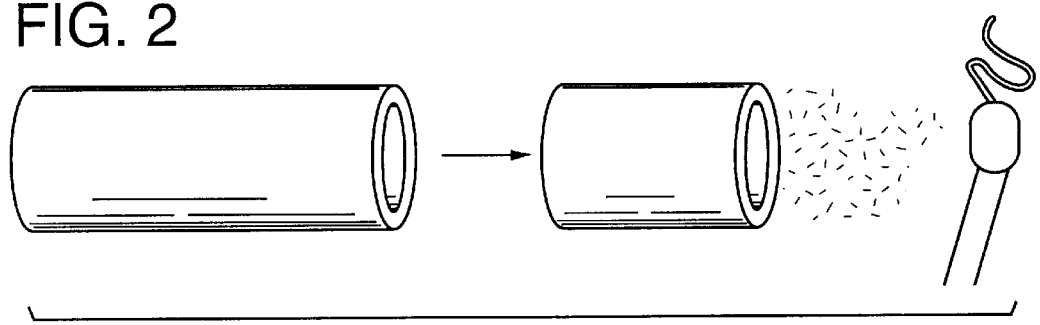
FIG. 2 is a schematic representation illustrating the dissolution of a therapeutic drug from the ends of a cylindrical microstructure.
Figure 3:
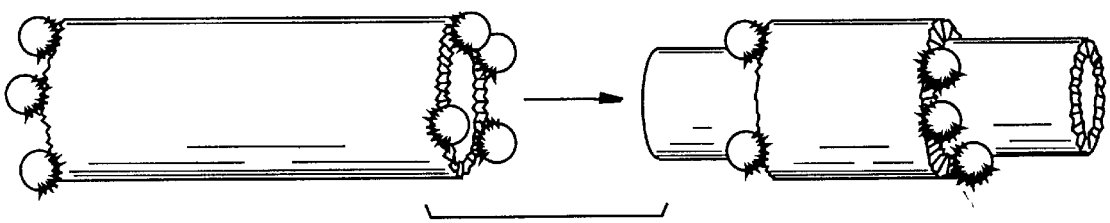
FIG. 3 is a schematic representation illustrating therapeutic release from a cylindrical microstructure under the influence of an enzyme-catalyzed hydrolysis reaction.

There are at least two methods for using HAR microstructures to produce continuous release of ligands. The first depends only on the dissolution of the ligand from the ends of HAR microstructures. This mechanism is illustrated in FIG. 2. In the second mechanism, the ligand is released from the HAR microstructure by the influence of an enzyme-catalyzed hydrolysis reaction. This is illustrated in FIG. 3. See the "Kinetics" section below for more discussion.

The present method of controlled release avoids pumps or incorporation of ligand into a macroscopic rigid matrix of a particular shape. The small diameter of HARMs allows them to be placed into cavities in the body using a needle or catheter, whereas their length immobilizes them after injection. For example, a wide range of HARM-based antitumor drugs could be injected into tumors (intralesionally) using small needles.

The following paragraphs (1) discuss the complexes, i.e., HARMs-Lg or HARMs-S-Lg, of the present invention and compositions comprising these complexes, (2) provide detail concerning how such compounds and complexes can be made, as well as the kinetics of dissolution and enzymatic cleavage and (3) describe using HARM complexes for administering therapeutics in vivo.

I. HARM-FORMING MATERIALS AND THERAPEUTICS

HARM-forming materials might themselves be useful, such as being therapeutics. Alternatively, ligands, such as therapeutics, are coupled to or associated with HARMs to produce composite compounds, also referred to herein as complexes. These composite compounds can satisfy the formulas HARM-Lg or HARM-S-Lg, where "HARM" refers to molecules that form high axial ratio microstructures, "Lg" is a ligand, such as a therapeutic, and "S" is a spacer. Complexes according to the present invention, such as HARM-Lg and HARM-S-Lg compounds, form suitable high axial ratio microstructures when subjected to microstructure-forming regimens. HARMs, therapeutics and spacers are discussed below.

A. HARMS

By way of example only and without limitation, specific materials that can be used to form high axial ratio microstructures for producing composite compounds for the delivery of therapeutics include amino-acid based amphiphiles, phospholipid-based amphiphiles, sphingosine-based amphiphiles (two types) and aldonamide-based amphiphiles. Generic structural formulas for these materials are provided below as Formulas 1–5, respectively.

Formula 1

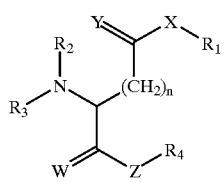

Formula 2

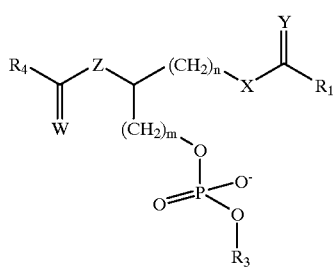

Formula 3

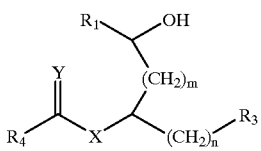

Formula 4

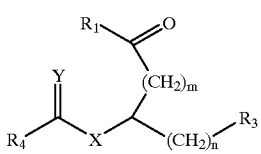

Formula 5

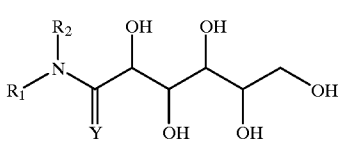

where n=1–10, preferably 1–2; m=1–10, preferably 1–2; $R_1$ is an aromatic ring or rings, typically 1–3 rings, or an aliphatic organic or heteroaliphatic organic chain having from about 1–30 atoms, 0–6 sites of unsaturation, such as double bonds, triple bonds, and combinations of double and triple bonds, and 0–6 heteroatoms, such as O, S, N, and combinations of such heteroatoms, $R_2$ is H, $R_1$ or $R_4$; $R_3$ is a functional group that allows noncovalent bonding of Lg to HARM; $R_4$ is an aromatic ring or rings, typically 1–3 rings, or an aliphatic organic or heteroaliphatic organic chain having from about 1–30 atoms, 0–6 sites of unsaturation, such as double bonds, triple bonds, and combinations of double and triple bonds, and 0–6 heteroatoms, such as O, S, N, and combinations of such heteroatoms.

Particular examples of these general materials include glutamate-based amphiphiles (Formula 6), polyglutamate-based amphiphiles (Formula 7), phosphatidylcholine with tricosadiynoyl fatty acyl chains, referred to as $DC_{8,9}PC$ (Formula 8), NFA-Galactocerebroside (NFA-Gal-cer) (Formula 9), and analogs of these compounds.

Formula 6

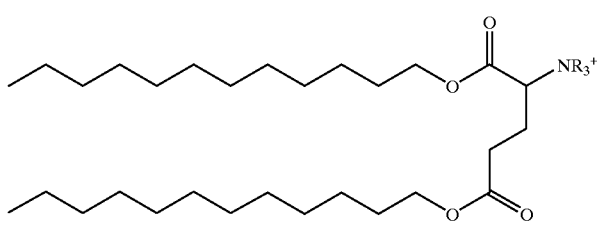

Formula 7

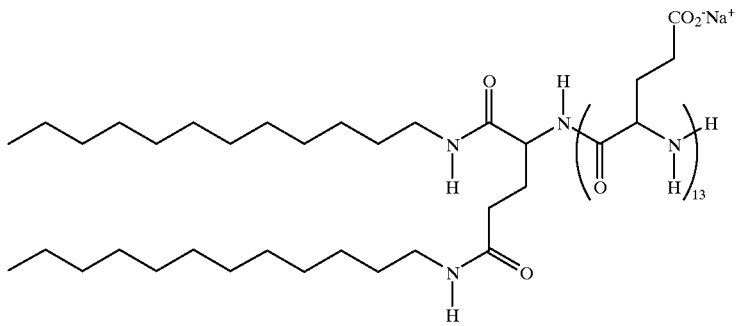

Formula 8

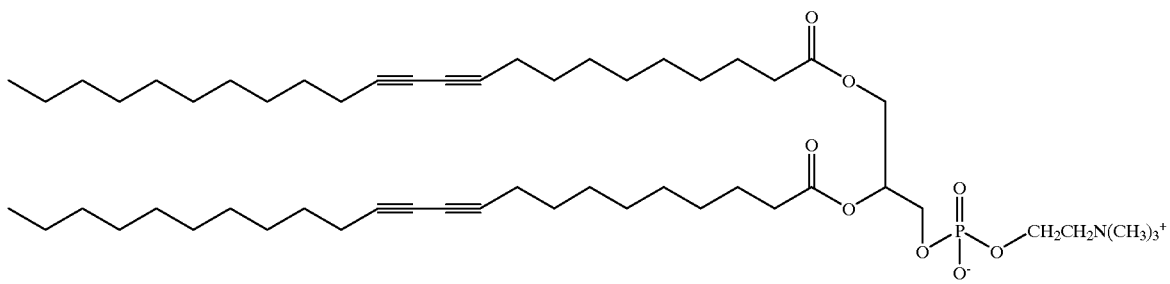

Formula 9

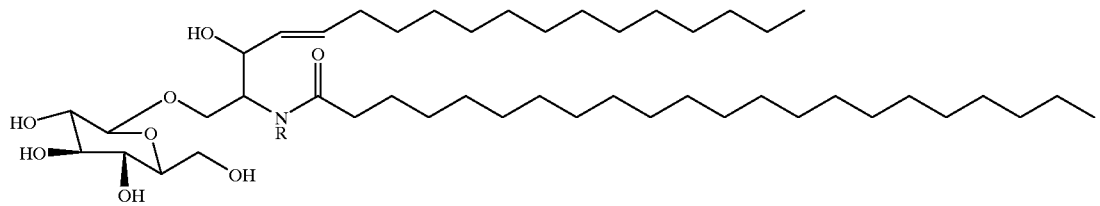

The compounds represented by Formulas 6–9 are commercially available or can be synthesized according to published procedures. More specifically, $DC_{8,9}PC$ is commercially available from Avanti Polar Lipids, Birmingham AL. NFA-Gal-cer and HFA-Gal-cer are commercially available from Sigma Chemical Company. Glutamate-based amphiphiles (represented by Formula 6) can be synthesized using procedures published by Kunitake. See, for instance, Kunitake et al.'s *Helical Superstructures are Formed from Chiral Ammonium Bilayers,* 1709–1712 (Chem. Lett., 1984). gee, also, Lee, et al., *Formation of High Axial Ratio Microstructures from Peptides Modified with Glutamic Acid Dialkyl Amides,* Biochemica et Biophysica Acta, 1371:168–184 (1998), which is incorporated herein by reference.

Compounds according to Formula 7, and derivatives thereof, can be synthesized according to the methods described by Yamada, such as in Yamada et al.'s *Formation of Helical Super Structure from Single-Walled Bilayers by Amphiphiles with Oligo-L-Glutamic Acid-Head Group,* 10:1713–1716 (Chem. Lett., 1984). Briefly, hexadecylamine was coupled to both of the free carboxyl groups of N-carbobenzoxy-L-glutamic acid with diethyl cyanophosphonate in the presence of triethylamine to form amide linkages. The carbobenzoxy protecting group was removed by hydrogenation using 10% Pd on activated carbon.

Analogs of the compounds represented by Formulas 6–9 also have proved useful for forming HARMs. For instance, the alkyl chains in each of the compounds shown in Formulas 6–9 can be changed to have different numbers of carbon atoms, as long as these modifications do not prevent such compounds from forming HARMs. The alkyl chain lengths, for example, of compounds satisfying Formula 7 have been varied to be other than C-12. The number of carbon atoms in such chains typically varies from about 8 carbon atoms to about 30 carbon atoms, typically from about 10 carbon atoms to about 20 carbon atoms, with the best results being achieved to date by compounds having from about 10 carbon atoms to about 14 carbon atoms.

Functional-group changes to compounds satisfying Formulas 6–9 also can be made to form additional analogs useful for form HARM-Th complexes. For example, NFA-Gal-cer can have an hydroxyl group α to the amide bond, which compound is referred to as HFA-GAL-Cer.

Representative HARM-forming compounds are provided below. These representative compounds form HARMs when subjected to HAR microstructure forming regimens in accordance with the present invention.

1. Glutamate-Based Analogs

TABLE 1

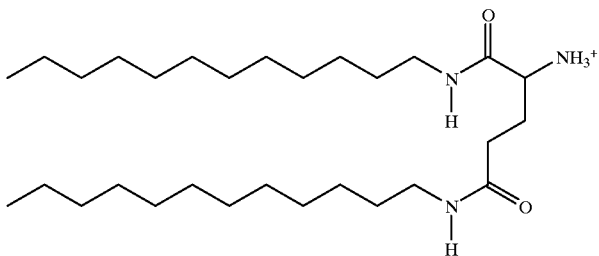

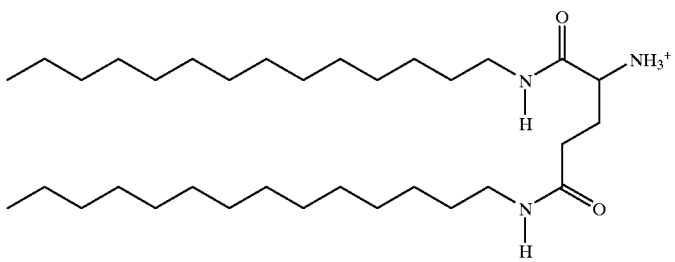

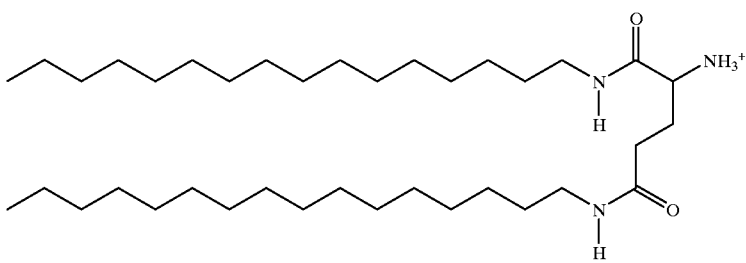

Thus, the glutamate-based compounds found useful for practicing the present invention typically satisfy general Formula 10 below

FORMULA 10

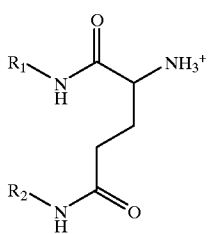

where $R_1$ and $R_2$ are independently selected from the group consisting of aliphatic carbon chains having from about 8 to about 30 carbon atoms, typically from about 10 to about 20 carbon atoms, with best results being achieved with carbon chains having from about 10 to about 14 carbon atoms. The carbon chains also can include sites of unsaturation, such as double bonds, triple bonds, and combinations of double and triple bonds. Moreover, the amide nitrogens also can have substituents other than hydrogen, such as lower alkyl groups (lower alkyl refers to carbon chains having less than about 10 carbon atoms).

2. Peptide/Aminoacid Analogs

Peptide/aminoacid analogs have been made using the core structures illustrated in Table 1, and analogs of the compounds of Table 1, by attaching various amino acids, polypeptides, or proteins to the amine nitrogen. Certain of these compounds are illustrated below. Compounds having plural amino acids, such as three proline groups, form cylindrical microstructures facilely.

Peptide/aminoacid analogs generally were made according to the procedure of Shimizu et al. See, for example, *Biochemica et Biophysica Acta.*, 1147: 50–58 (1993). And, compounds having polypeptides attached thereto were synthesized to include trypsin cleavage sites. The synthesis of compounds having peptides attached thereto also is described in Examples 2 and 3.

TABLE 2
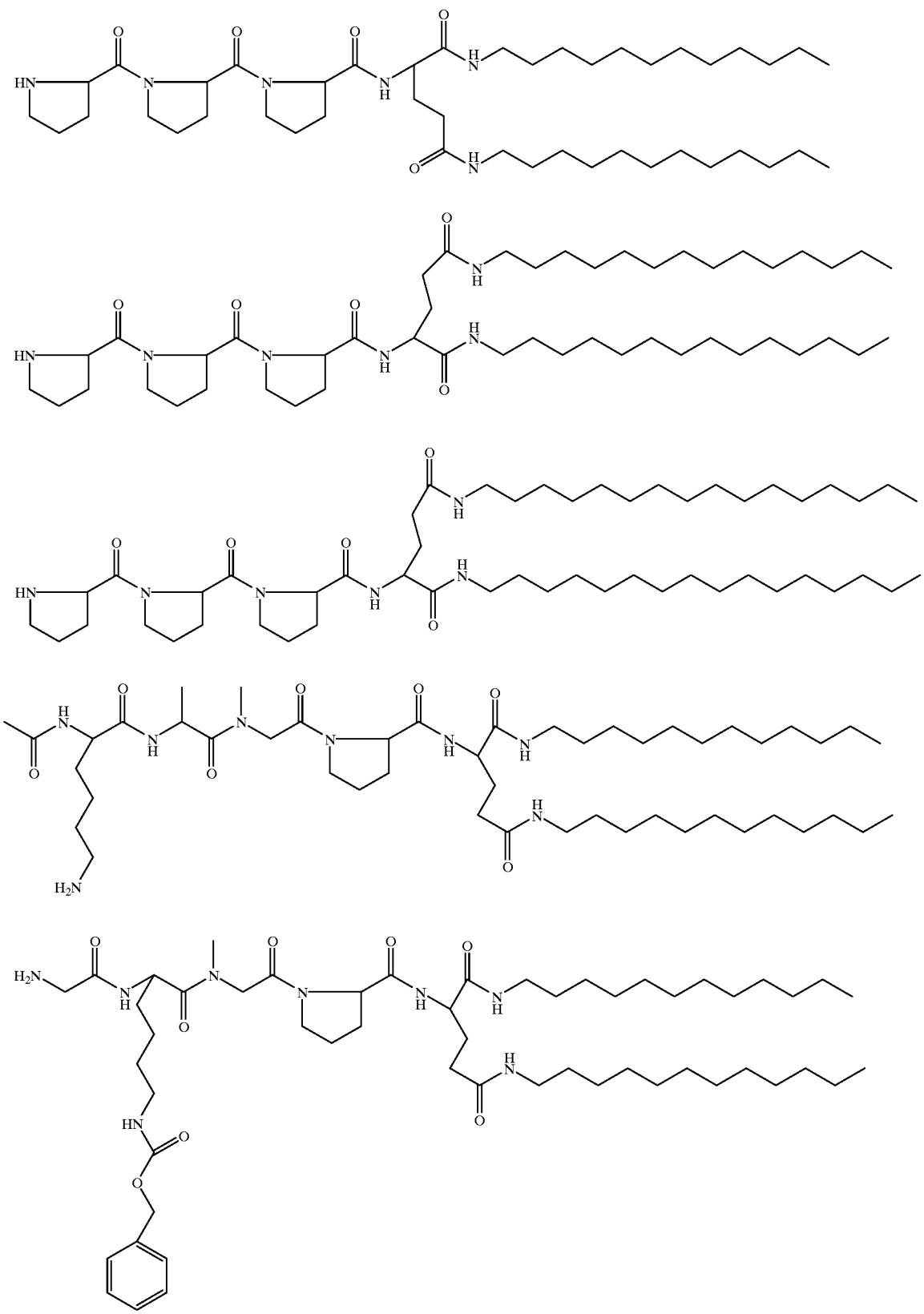

TABLE 2-continued

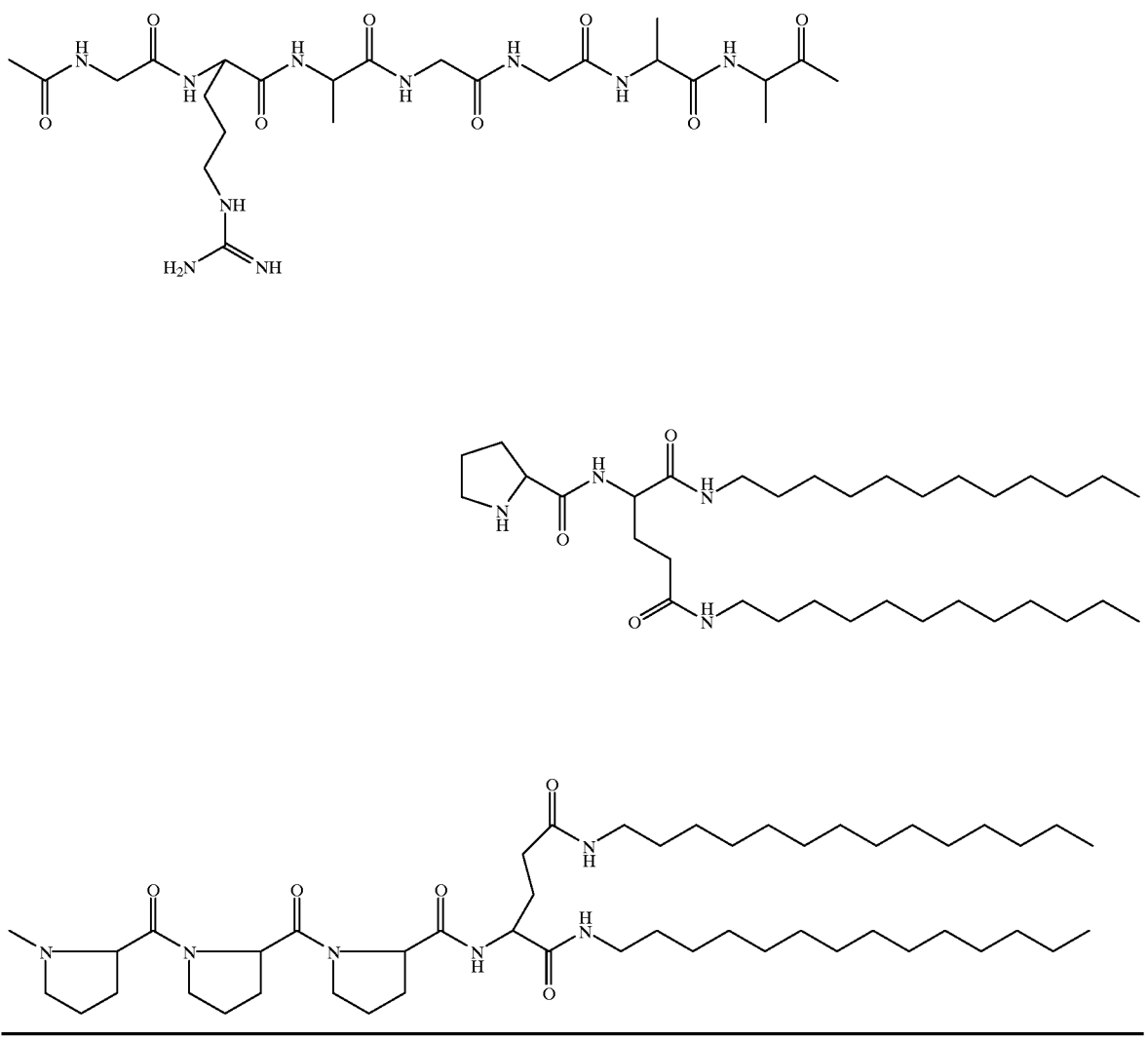

Numerous novel ceramide-type compounds have been synthesized and formed into HARMs using microstructure-forming regimens. The ceramides comprise sphingosine acylated with fatty acids. Good results have been obtained using nervonic acid, or fatty acids similar thereto, coupled to sphingosine, or derivatives thereof, to provide N-nervonoyl-type ceramides. The structural formula for N-Nervonoyl ceramide is provided below. formula for N-Nervonoyl Ceramide

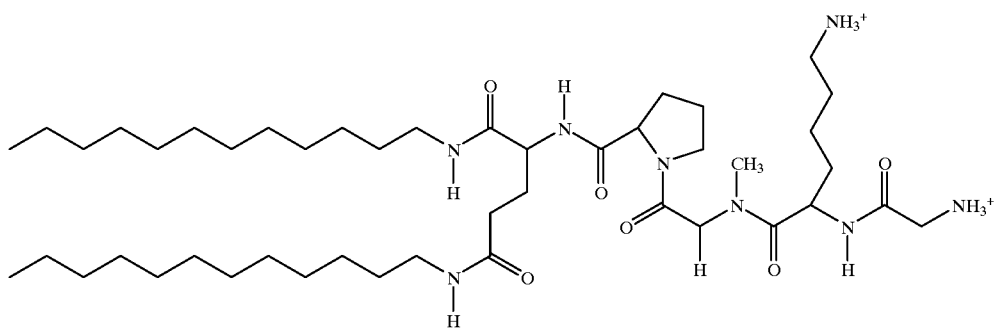

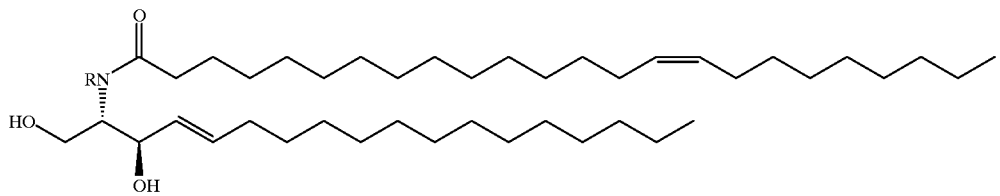

N-Nervonoyl Ceramide

Nervonic acid was chosen for several reasons. First, it is present naturally in the body, and therefore is not toxic. Second, it includes a site of unsaturation, i.e., a double bond, which favors formation of HARMs relative to compounds which do not include sites of unsaturation. Various HARMs also can be made by selectively coupling compounds to the 1° hydroxyl group of sphingosine.

Certain of the ceramide analogs synthesized to date are shown below. The synthesis of these ceramide analogs is further discussed in Example 5. The compounds shown below can include various atoms and alkyl groups for R, such as hydrogen, lower alkyl groups, and carbonyl-containing groups, such as acyl groups.

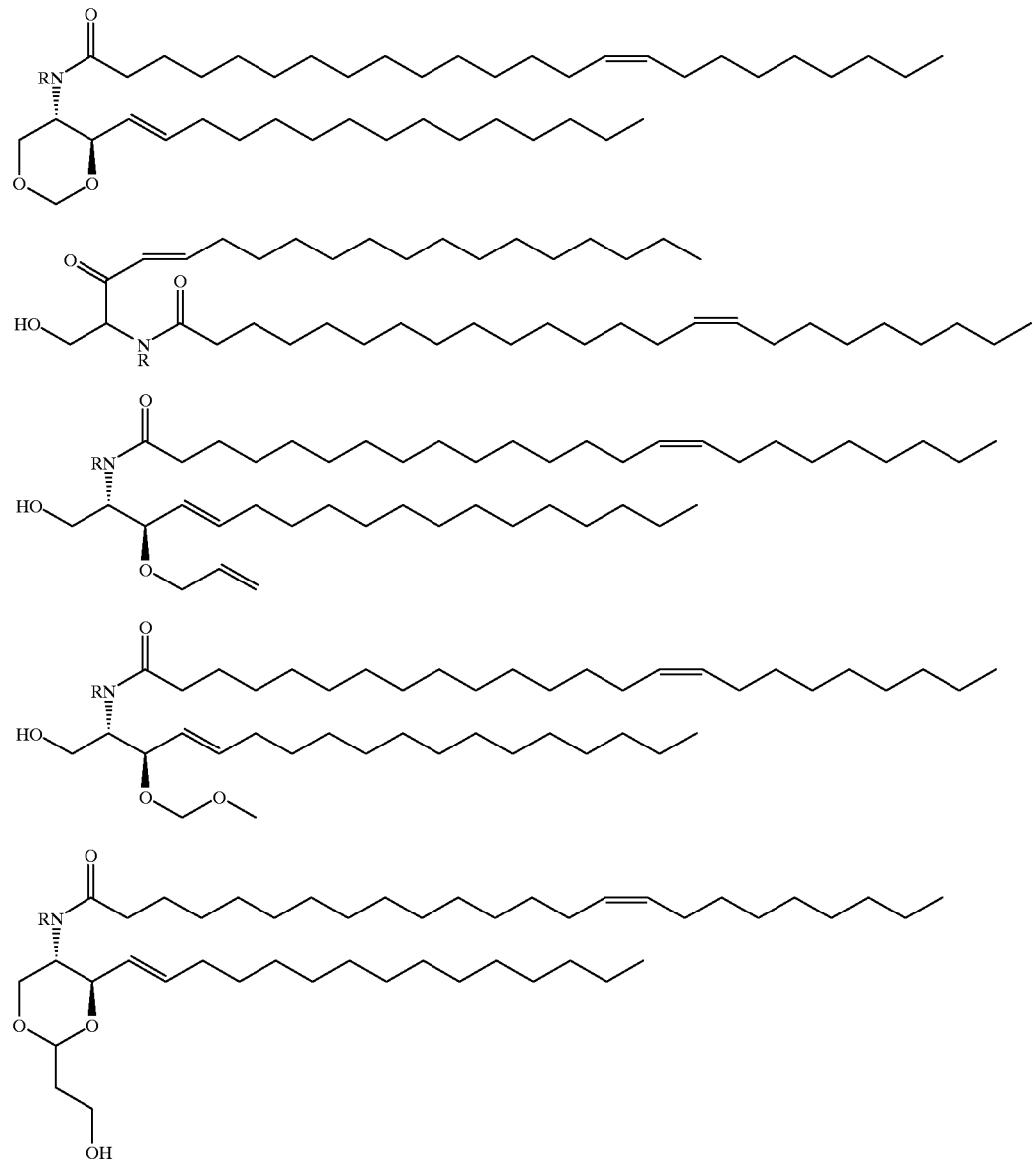

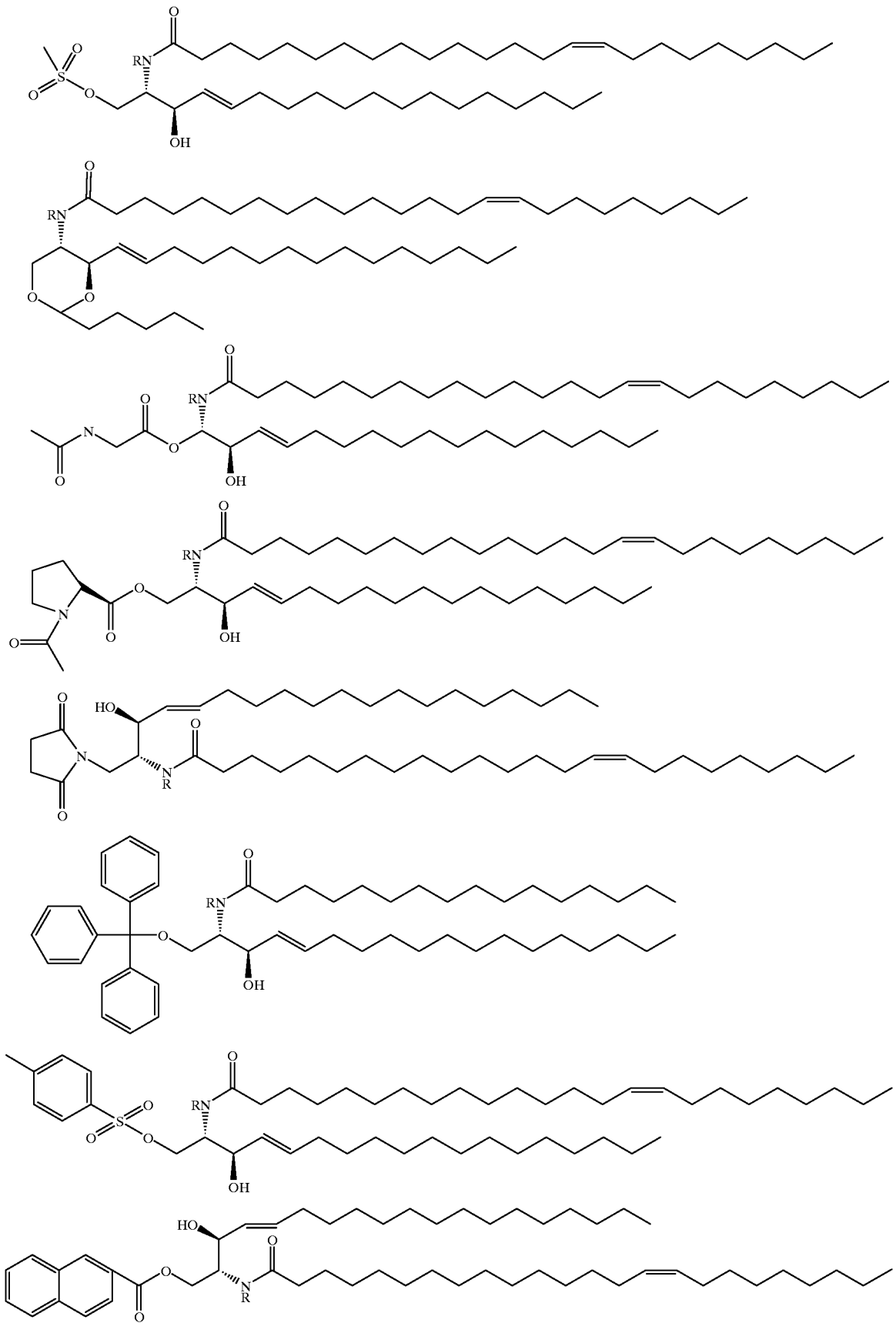

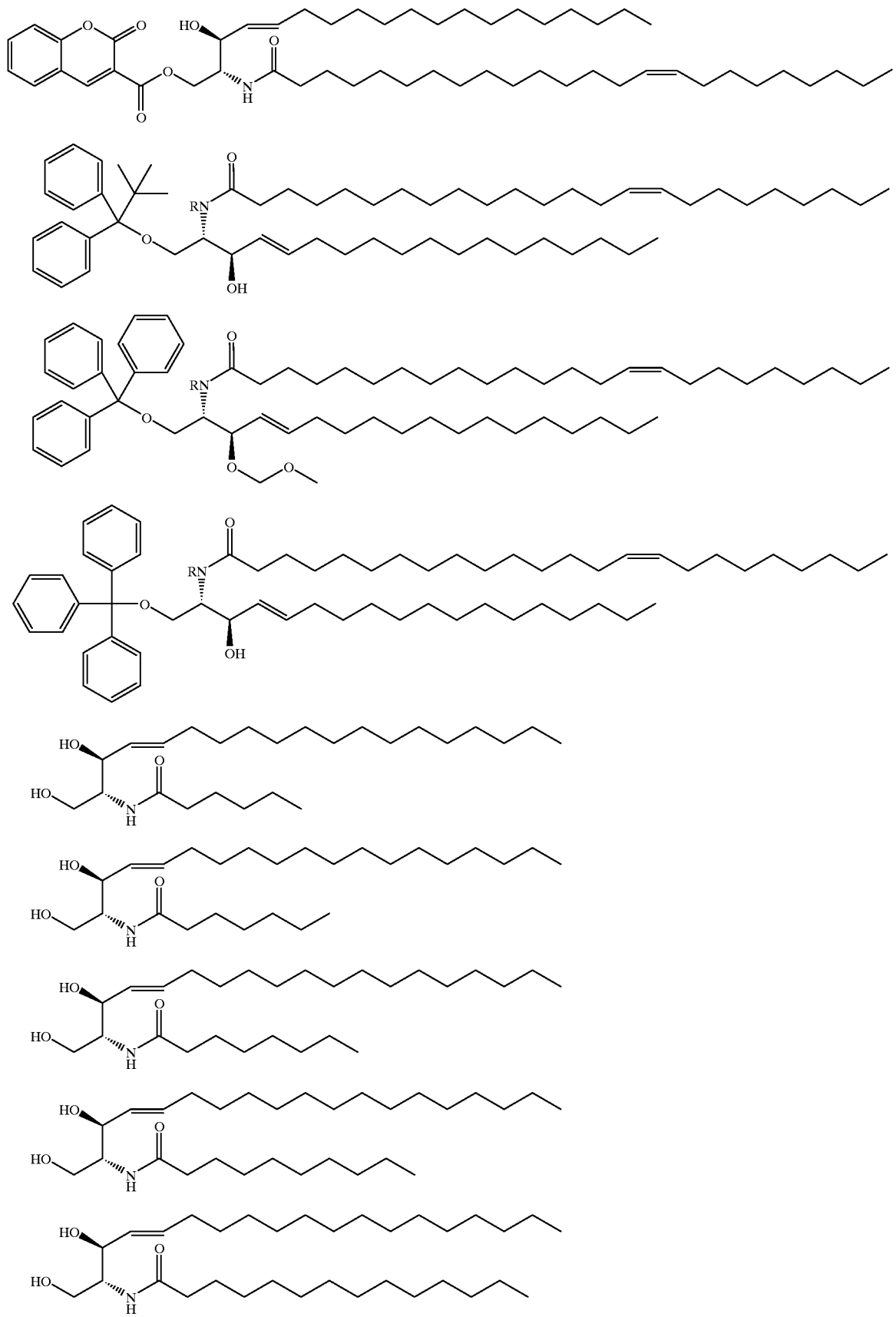

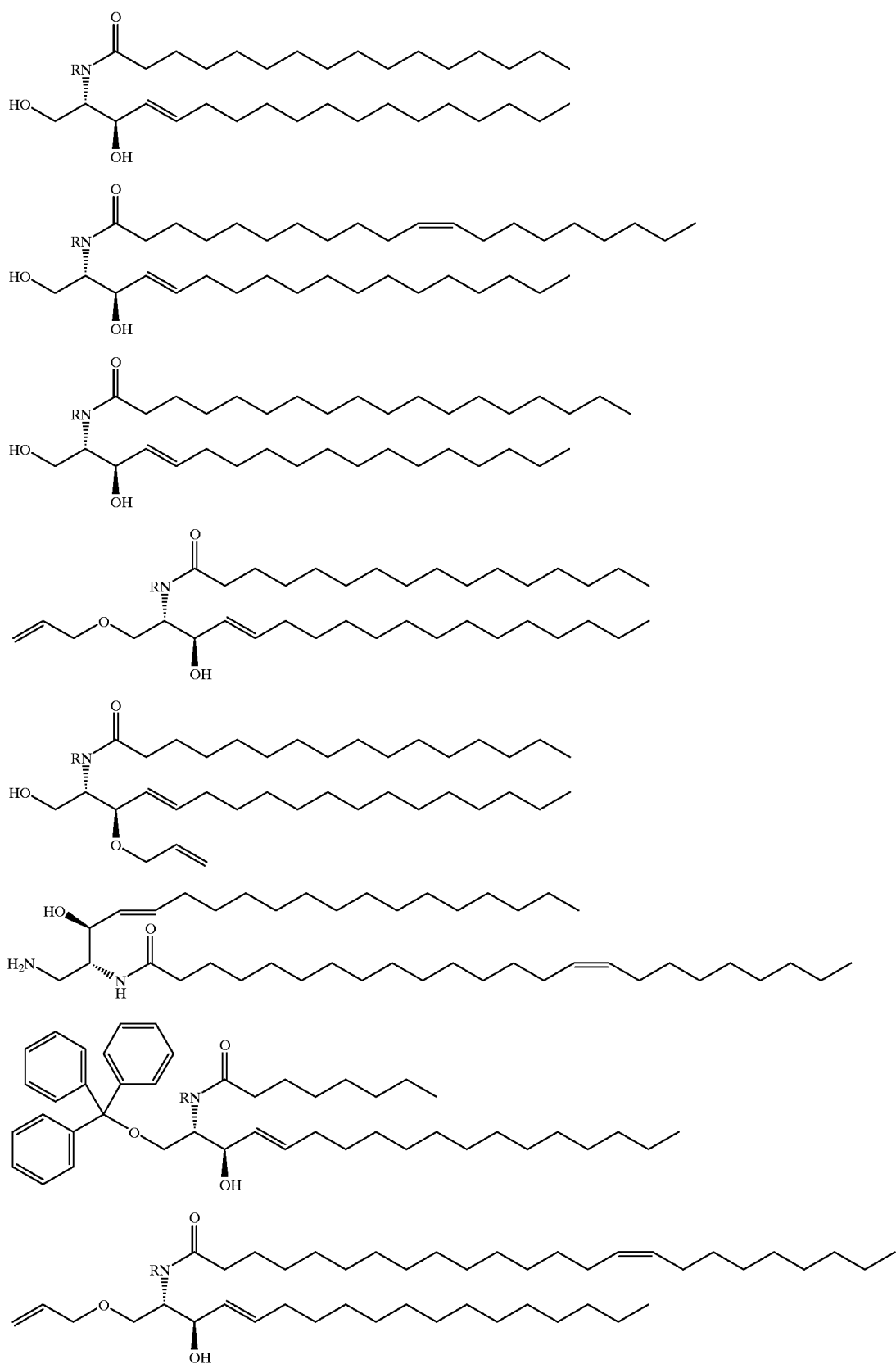

4. Cerebroside Analogs
A number of cerebroside analogs also have been made, and representative compounds are provided below.
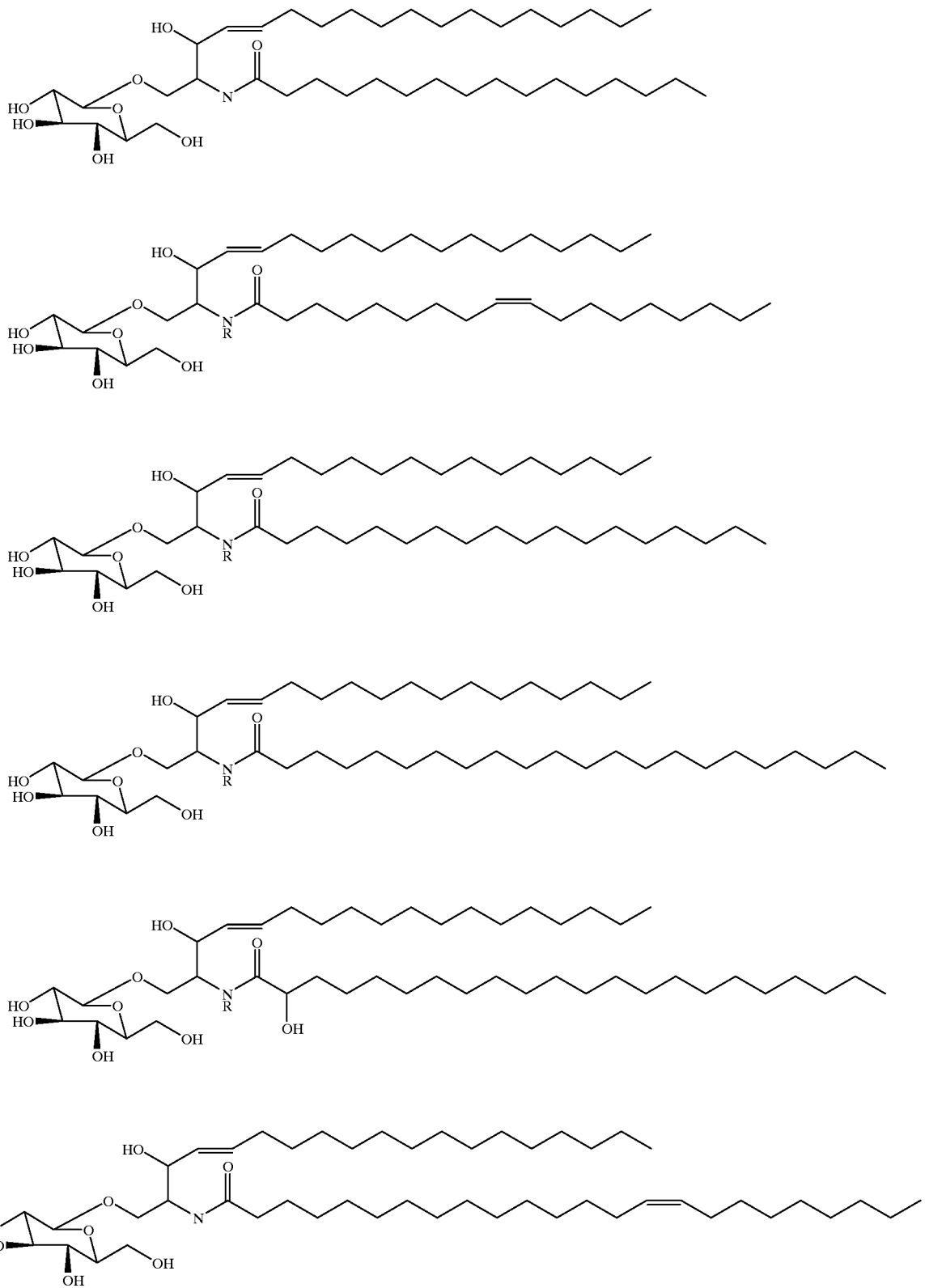

5. Miscellaneous HARM-Forming Materials

Other miscellaneous materials also have been used to form HARMs. One example of such a compound is psychosine, the structural formula for which is provided below.

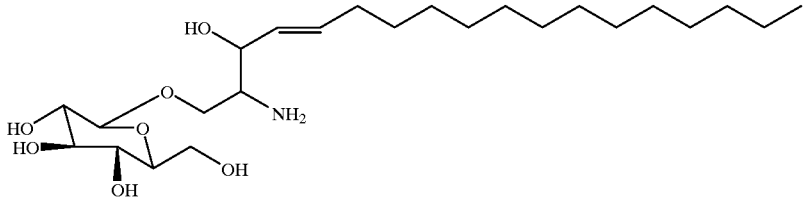

Based on the above, compounds found suitable in working embodiments for forming high axial ratio microstructures are selected from the group consisting of $DC_{8,9}PC$, NFA-Galactocerebroside, HFA-Galactocerebroside, $NH_2$-Glu-(NH—$C_{12}H_{25}$)$_2$/Pro-Glu-(NH-$C_{12}H_{25}$) $_2$, $NH_2$-Gly-Lys-Sar-Pro-Glu-(NH—$C_{12}H_{25}$)$_2$, NAcPro-ceramide, $NH_2$-Glu-(NH—$C_{14}H_{29}$)$_2$ (I), N-hexanoyl ceramide, N-heptanoyl ceramide, N-octanoyl ceramide, psychosine, N-decanoyl ceramide, N-myristoyl ceramide, N-palmitoyl ceramide, N-oleoyl ceramide, N-stearoyl ceramide, N-palmitoyl-1-O-allyl ceramide, N-palmitoyl-3-O-allyl-ceramide, $NH_2$-Glu-(NH–$C_{16}H_{33}$)$_2$, N-nervonoyl ceramide, N-nervonoyl-(1,3-formyl acetal) ceramide, N-nervonoyl-3-oxo ceramide, N-nervonoyl-1-amino ceramide, N-octanoyl-1-O-triphenylmethyl ceramide, N-nervonoyl-1-O-allyl ceramide, N-nervonoyl-3-O-allyl ceramide, N-nervonoyl-3-O-methoxymethyl ceramide, N-palmitoyl galactocerebroside, N-nervonoyl-(1,3-(3-hydroxy)-propyl acetal) ceramide, N-oleoyl galactocerbroside, N-nervonoyl-1-O-mesyl ceramide, N-stearoyl galactocerebroside, N-nervonoyl-(1,3-hexyl acetal) ceramide, NAcGly-ceramide, N-nervonoyl-1-phthalimido ceramide, Pro-Pro-Pro-Glu-(NHC$_{12}$H$_{25}$)$_2$1, N-palmitoyl-1-O-triphenylmethyl ceramide, N-nervonoyl-1-O-tosyl ceramide, N-nervonoyl-1-(2-napthoic acid)-ceramide, N-nervonoyl galactocerebroside, Pro-Pro-Pro-Glu-(NHC$_{14}$H$_{29}$)$_2$, N-nervonoyl-1-(coumarin-3-CO$_2$H) ceramide, N-nervonoyl-1-O-tertbutyldiphenylsilyl ceramide, Pro-Pro-Pro-Glu-(NHC$_{16}$H$_{33}$)$_2$, Lys-Ala-Sar-Pro Glu-(NHC$_{12}$H$_{25}$)$_2$, N-nervonoyl-1-O-triphenylmethyl-3-methoxymethyl-ceramide, N-nervonoyl-1-O-trityl ceramide, Gly-Lys-(e-Z)-Sar-Pro-Glu-(NHC$_{12}$H$_{25}$)$_2$, Ac-GRAGGAAPPP-E-(NHC$_{14}$H$_{29}$)$_2$ and mixtures thereof. The present invention is not limited to using a compound or compounds from this list.

B. LIGANDS

Once an appropriate HARM-forming material is selected, a ligand must be selected. It will be appreciated that a number of different classes of ligands can be used, including diagnostics, biocidal materials, and therapeutics. Although all such ligands can be used to practice the present invention, therapeutics currently are the most likely class of materials to be bonded to or associated with the high axial ratio microstructures.

The therapeutic compound (Th) is coupled to or associated with individual HARMs to form composite compounds. The therapeutic compounds can be conventional pharmaceuticals, peptides, proteins (enzymes, antigens, etc.), nucleic acids (such as DNA and RNA), cells, etc. By way of example only, and without limitation, the following is a partial list of therapeutics that can be coupled to materials to form complexes having high axial ratio microstructures.

1. Peptides

A number of peptides currently are used for treating a variety of conditions and maladies. For instance, candidate peptides for practicing the present invention include insulin, vasopressin, growth hormone, and any other natural or synthetic peptide ligand now known or hereafter discovered or synthesized for endogenous receptors. Peptides also can be used to form vaccines, such as orally administered vaccines. "Vaccine" generally refers to systems that deliver an antigen, generally a peptide, protein, or nucleic acid that codes for a peptide or protein, in a controlled manner to elicit an immune response.

2. Steroids

Another example of a class of compounds commonly used as therapeutics are steroids. Examples of candidate steroids for forming high axial ratio microstructure complexes include estrogen, progesterone and testosterone. Synthetic and/or semi-synthetic derivatives (eg estrone or methyl-testosterone) also can be used. Combinations of these steroids also may be used, such as are used in birth control formulations, and methylprednisolone, which is used as an anti-inflammatory corticosteroid.

3. Conventional Pharmaceuticals

Another class of candidate agents for forming hixh axial ratio microstructure complexes are the conventional organic pharmaceuticals. Examples of such compounds, without limitation, include:

(1) antihypertensives, e.g., calcium channel blockers such as nifedipine and verapamil.

(2) vasodilators, such as nitroglycerin.

(3) diuretics, such as lasix and hydrochlorothiazide.

(4) psychotropics (benzodiazepines), such as diazepam.

(5) stimulants, such as methylphenidate. (6) antidepressants, such as doxepin or serotonin specific re-uptake inhibitors including Prozac.

(7) antipsychotics, such as lithium and haloperidol.

(8) antiemetics, such as chlorpromazine or scopolamine.

(9) analgesics, such as acetaminophen and acetylsalicylic acid.

(10) non-steroidal anti-inflammatory drugs (NSAIDs), such as indomethacin or naproxen.

(11) histamine antagonists, such as cimetidine, ranitidine and diphenhydramine.

(12) narcotics, such as morphine and demerol.

4. Nucleic Acids

Nucleic acids encoding biologically-active peptides and proteins are being used more often as potential therapeutics and vaccination tools. Nucleic acids useful in the practice of the present invention comprise isolated nucleic acids. An "isolated" nucleic acid has been substantially separated or purified away from other nucleic acid sequences in the cell of the organism from which it naturally occurs, i.e., other chromosomal and extrachromosomal DNA and RNA. The term thus encompasses nucleic acids purified by standard nucleic acid purification means. It also embraces nucleic acids prepared by recombinant expression in a host cell and chemically synthesized nucleic acids. Also included are nucleic acids that are substantially similar to such nucleic acids. Methods for chemical synthesis of nucleic acids are discussed, for example, in Beaucage and Carruthers, Tetra. Letts. 22:1859–1862, 1981, and Matteucci et al., J. Am. Chem. Soc. 103:31835, 1981. Chemical synthesis of nucleic acids may be performed, for example, on commercial automated oligonucleotide synthesizers.

Without an adequate delivery system, nucleic acids cannot be used as therapeutics due to their low permeability through cell membranes, excretion and enzymatic degradation. Glutamic acid dialkylamide-based HARMs have been used both as a depot vehicle as well as a material for internalizing DNA. Glutamic acid dialkylamides (GADs) are positively charged under physiological conditions. Phase transition temperatures and solubilities of GAD-based HARMs can be varied by altering the hydrocarbon chain length and head group structure of the constituent glutamic acid derivatives, allowing their physical properties to be tailored for a particular purpose.

DNA-HARM complexes slowly release DNA into the interstitial space of tissues due to dissolution of a HARM-forming GAD. This provides a sustained source of naked DNA.

HARMs formed from GADs with a chain melting temperature close to physiological temperature enhances fusion with cell membranes because of their own membrane rearrangements upon injection. Such fusion transfers HARM-incorporated DNA through the membranes. Additionally, fine tuned HARM-based DNA delivery systems can be constructed employing GADs with peptide head groups with specific properties such as affinity to certain type of cells, peptides facilitating lipid membranes fusion, etc.

C. SPACERS

Figure 4:
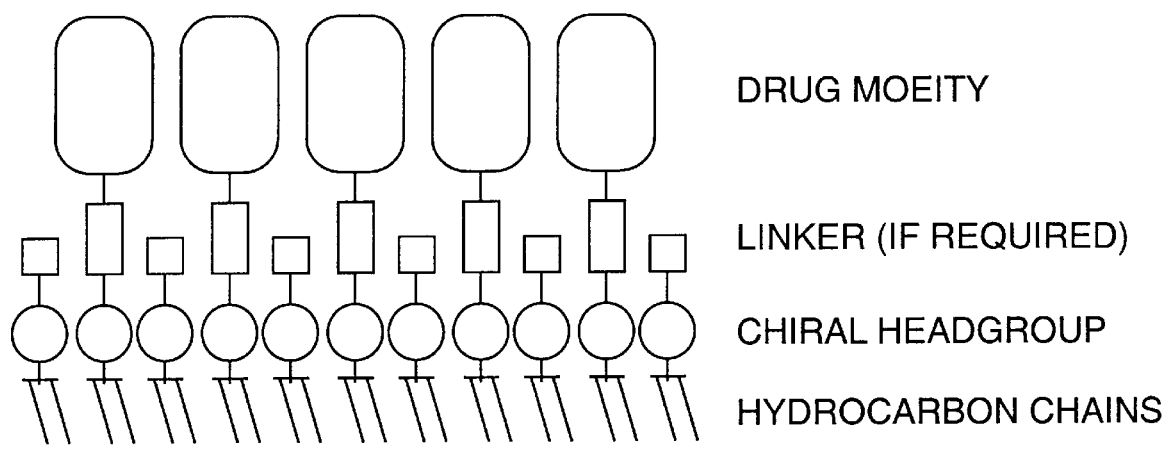
FIG. 4 is a schematic representation illustrating the use of spacers for coupling therapeutics to cylindrical microstructures.
Figure 5:
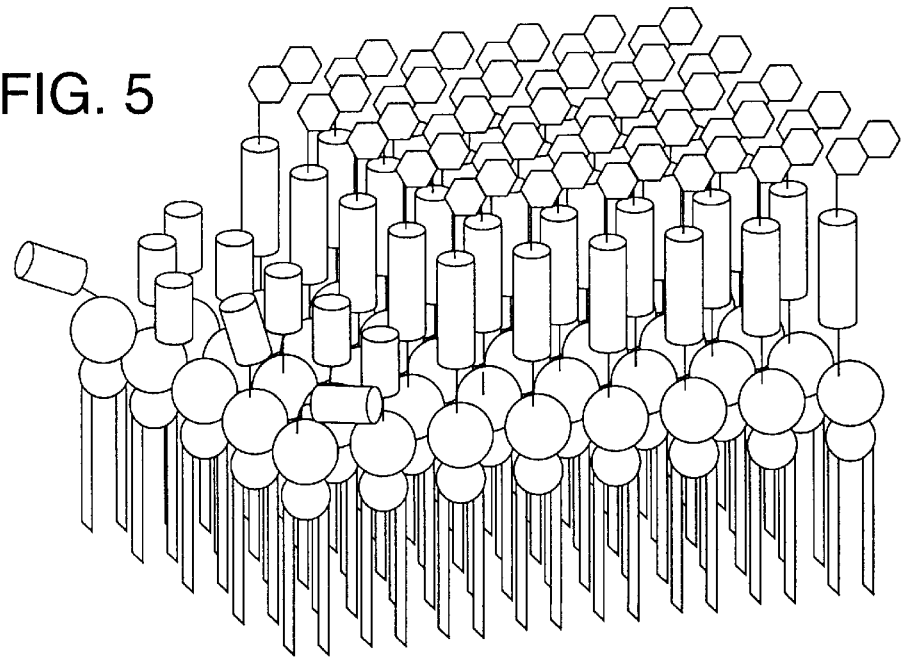
FIG. 5 is a schematic representation of a monolayer array of lipids at the edge of a tubule representing the enzymatic cleavage of a spacer.

Ligands can be directly coupled to HA?Ms or materials that when coupled to the ligands can still form the high axial ratio microstructures. Alternatively, the ligand can be coupled to the HARM, or material used to form the HARM, using a spacer (spacers also are referred to as tethers and linkers), i.e., HARM-S-Lg. Spacers uncouple the steric interactions of the agents from the packing of the HAR-forming lipids. The spacer also can provide a cleavage site recognized by an enzyme that is either dispensed in combination with the HARMs-Lgs compounds, or is endogenous to the environment in which the HARMs-Lgs are administered. See FIG. 4, which provides a schematic representation illustrating the use of spacers for coupling ligands to HAR microstructures.

Polypeptides are an example of a class of spacers. Such polypeptides generally will include a sequence known to be susceptible to attack by a protease, such as, without limitation, trypsin and trypsin-like enzymes (trypsin cleaves on the carboxyl side of lysine and arginine residues) and elastase (which recognizes Ala-Ala-Ala sequences) at the site of use. For instance, compounds similar to that shown in Formula 6 have been made which include trypsin cleavage sites at different positions along the chain. Packing of the drugs at the surface of the microstructure generally is tight enough to prevent access by a protease. Only at the disordered ends of the HAR microstructures is there access to the cleavage site for enzyme activity. As a result, drug release is controlled by the constant number of intact spacers exposed at the advancing front.

Polypeptides are not the only compounds potentially useful as spacers for the purpose of separating the steric interaction between the HARM and ligands. Alternatively, the spacer might include a functional group of limited stability against cleavage at the site of use. For example, the spacer might simply comprise alkyl, alkenyl or alkynyl carbon chains having a functionality that is readily cleaved in the environment in which the composite compounds are administered. Such compounds might be esters, as long as the ester functionality is sufficiently labile in the environment in which the composite compounds are administered to release Lg upon hydrolysis. Alternatively, the spacers might comprise carbohydrates or polyoxyalkylenes, particularly polyoxymethylene and polyoxyethylene.

II. Forming Complexes Comprising HARM-Lg and HARM-S-Lg

The following paragraphs discuss bonding or associating particular classes of compounds to HARMs to form the composite HARM-Lg or HARM-S-Lg. Specific guidance as to the means for bonding or associating Lg to a particular HARM depends upon several factors, including the nature of the HARM, the Lg, and on the environment in which the composite compounds will be administered. For covalent, electrostatic or hydrogen bonding, the head group of the HARMs described herein include nucleophilic and/or polar groups, such as amine and hydroxyl groups. For covalent bonding, these nucleophilic groups can be reacted with electrophilic species to couple the agents to the HARMs.

A. PEPTIDES

Peptides, such as insulin and enkephalins, are an important class of compounds that can be delivered using HARMs. Peptides of any desired sequence can be synthesized using standard synthetic techniques, such as solid-phase synthesis using Applied Biosystems Peptide Synthesizers or other available devices. In order to couple the peptide to the α-amino group of dialkylated glutamine compounds or glutamic acid lipids, the peptide is prepared with its N-terminus and all of its reactive side chains in protected form. Moreover, the peptide includes a free C-terminal carboxyl group. This is accomplished using a special peptide synthesis resin called super acid-sensitive resin, known as SASRIN, which is available from Bachem, Inc. The fully protected peptide is cleaved from the resin with mild acid, such as 1% trifluoroacetic acid in methylene chloride. This leaves the side chain and N-terminus protecting groups intact.

Peptide synthesis is accomplished with the a-amino groups of the amino acids protected, such as with a fluorenylmethyloxycarbonyl (FMOC) protecting group, and bearing standard side-chain protecting groups that are removed with strong acid (i.e., trityl, t-butyl, etc.). After the N-terminal amino acid is attached to the polypeptide, the FMOC group can be left on and removed along with the side chain protecting groups after the peptide is coupled to the lipid. Alternatively, the FMOC protecting group can be removed while the peptide is still bound to the resin. This allows modifications of the N-terminus, such as by modifying the N-terminus with probes. Probes containing an N-hydroxylsuccinimide ester or an isothiocyanate can be used for attachment to the peptide N-terminus.

After the polypeptide is cleaved from the SASRIN resin, it is then coupled to the a-amino group of dialkylated glutamine compounds or glutamic acid lipids using either dicyclohexylcarbodiimide or diethyl phosphorylcyanate in a solvent such as DMF or methylene chloride. Coupling is monitored by observing the loss of the lipid $NH_2$ group using the Kaiser test. Kaiser et al.'s *Color Test for Detection of Free Terminal Amino Groups in the Solid-Phase Synthesis of Peptides,* 34:595–598 (Anal. Biochem., 1970). After coupling, the crude material is treated with neat trifluoroacetic acid containing the appropriate scavengers (thioanisole, 1,2-dithioethane, etc., depending on the structure of the side-chain protecting groups). The crude Lipidic-peptides are purified by HPLC on a reverse-phase column.

B. NUCLEIC ACIDS

Desired nucleic acid compounds can be attached to the HARMs by a variety of methods. However, by way of example only and without limitation, nucleic acids can be covalently coupled to HARMs using the 5'-hydroxyl group. This hydroxyl group can be used to link nucleic acids to the HAR-forming lipids via an ester functionality. Because a number of the HAR-forming lipids used for the present invention have amines at the head group (See, for instance, the compounds of Table 1), an additional group containing a free carboxyl group must be used to couple the nucleic acids to the HARM-forming lipids. For example, peptide spacers comprising amino acids having a side-chain carboxyl group can be used to couple nucleic acids to the HARMs. Aspartic and glutamic acid are examples of amino acids having a carboxyl functionality that could be included in the peptide spacer to link nucleic acids to the HARM-forming molecules.

It also has been demonstrated that nucleic acids can be associated noncovalently with materials to form complexes having high axial ratio microstructures. These complexes have been used to deliver DNA in vivo. Furthermore, the complexes protect the DNA from enzymatic degradation. See, Examples 19–25 below.

C. CONVENTIONAL PHARMACEUTICALS

Conventional pharmaceuticals also can be attached to the HARMs. The method for attachment depends on the particular HARM and therapeutic selected. However, solely by way of example, the following provides a discussion concerning the attachment of particular classes of conventional therapeutics to HARMs.

1. Steroids

Steroids generally have a hydroxyl group in the A ring (the first 6-membered ring). This hydroxyl group can be used to link steroids to the HAR-forming lipids via an ester functionality as discussed above for nucleic acids. Because a number of the HAR-forming lipids used for the present invention have amines at the head group (See, for instance, the compounds of Table 1), an additional group containing a free carboxyl group must be used to couple the steroid to the HAR-forming lipids. Amino acids having a carboxyl group in a side chain could be included in peptide spacers to link steroids to the HAR-forming molecules.

2. Acetylsalicylic Acid

Acetylsalicylic acid (aspirin) is an additional example of a conventional therapeutic that could be delivered using HAR-forming lipids. Acetyl-salicylic acid includes a carboxyl group that could be used to form an amide with an amine or an ester with a hydroxyl group. As stated above, a number of the HTR-forming lipids have amines at the head group of the lipid. The amine could be used to form an amide with the carboxyl group of acetylsalicylic acid.

HAR-forming lipids that include hydroxyl groups could be directly attached to acetylsalicylic acid via an ester. HAR-forming lipids that have amines at the head group generally will be coupled to compounds such as acetylsalicylic acid using spacers. For example, polypeptide spacers could be used for this purpose wherein at least one of the amino acids in the polypeptide includes a side chain having an hydroxyl group, such as serine. The side-chain hydroxyl group could be coupled to the carboxyl group of acetylsalicylic acid via an ester functionality.

III. HAR-Forming Regimens and Microstructure Morphology

Therapeutics can be coupled to or associated with compounds self assembled into HARMs. Alternatively, the HARMs and Ths are first coupled to or associated with each other, and then subjected to HAR-forming regimens. The conditions required to form the desired microstructures may differ from compound to compound, although all the surfactants synthesized form aggregates in water because of their hydrophobic tails. The following procedures have proved most useful for inducing the HAR microstructures in the compounds tested to date.

(1) heating a suspension of lipids in water to a temperature above $T_m$ (lipid hydrocarbon chain melting temperature), followed by slow cooling through $T_m$;

(2) heating a suspension of lipids in water to a temperature above the $T_m$, sonicating to form small unilamellar vesicles (SUVs), cooling to a temperature well below $T_m$ until extended multilamellar sheets are formed, heating slowly to above $T_m$ and then cooling slowly to a temperature below $T_m$;

(3) at $T<T_m$, completely dissolving lipid in a water-miscible solvent, such as an alcohol, and adding an appropriate ratio of a non-solvent, such as water, until HAR microstructures precipitate directly from the mixture (Georger et al.);

(4) at $T>T_m$, completely dissolving lipids in a water-miscible solvent, adding a nonsolvent such as water and lowering the temperature slowly to below $T_m$ (Jerome Lando et al.);

(5) suspend lipid at $T<T_m$ in a water/glycol mixture, heating to $T>T_m$, cool to a $T<<T_m$, and repeating at least one more time (this method was developed by Archibald and Yager for forming tubules from NFA-cer and cochleates from HFA-cer);

(6) dispersing and/or sonicating lipids above $T_m$, and cooling to below $T_m$ and waiting for the microstructures to form (this method is generally applicable to materials having a high CMC);

(7) precipitation upon dilution of concentrated methanol solution of peptide lipids with aqueous media;

(8) thermal cycling, plural times, peptide lipid suspensions in pure aqueous buffer;

(9) thermal cycling, plural times, of peptide lipid suspensions in mixtures of aqueous buffers and alcohols; and

(10) dissolving lipids in a solution of a detergent, such as octyl glucoside, at a concentration greater than the CMC of the detergent, followed by dialysis of the mixture to remove the detergent.

(11) addition of GAD solution in absolute EtOH, vortexing, and incubation at room temperature overnight followed by incubation of the suspension at 55° C. for a period of time and then slowly cooled to room temperature.

(12) overnight incubation of a HARM forming GAD in octyl glucoside in HBS at room temperature.

Each of these methods also may involve varying certain steps to maximize the formation of cylindrical microstructures. For instance, the pH may have to be adjusted to account for different association tendencies for particular compounds.

Certain tubule- and cochleate-forming techniques also are described in detail in the following references, each of which is incorporated herein by reference. Yager et al.'s *Formation of Tubules by a Polymerizable Surfactant*, 106:371–381 (Mol. Cryst. Liq. Cryst., 1984); Yager et al.'s *Two Mechanisms for Forming Novel Tubular Microstructures from Polymerizable Lipids*, 49:320 (Biophys. J., 1986); Yager et al.'s *Helical and Tubular Microstructures Formed by Polymerizable Phosphatidylcholines*, 109:6169–6175 (J. Am. Chem. Soc., 1987); Yager et al.'s *Microstructural Polymorphism in Bovine Brain Galactocerebrosides and its Two Major Subfractions*, 31:9045–9055 (Biochemistry, 1992); Yager et al.'s *A Model for Crystalline Order Within Helical and Tubular Structures of Chiral Bilayers*, 58:253–258 (Chemistry and Physics of Lipids, 1991); Yager et al.'s U.S. Pat. No. 4,911,981, entitled Process for Fabrication of Lipid Microstructures; Yager et al.'s U.S. Pat. No. 4,990,291, entitled Method of Making Lipid Tubules by a Cooling Process; and Yager et al.'s Method of Making Lipid Tubules by a Cooling Process, D.o.t.N.G., Inc., Editor (1991).

The microstructures formed in accordance with the general procedures outlined above, and as described in more detail in the examples, can be confirmed using a light microscope for lipid microstructures having dimensions larger than about 1 μm. A Zeiss ICM-405 inverted microscope has been equipped for epifluorescence illumination, brightfield, and phase contrast imaging; attachments include a 63 x 1.40 NA Planapochromat, a 35 mm camera, and a Peltier effect microscope stage for sample temperature control (−20 to +100° C., +/−0.1° C.). A Dage 66 SIT video camera (with S-VHS VCR and monitor) allows video imaging through the microscope in all imaging modes. Image processing and printing from live or stored video is possible using a Data Translation QuickCapture frame grabber board in a Macintosh II. This system allows imaging of HAR microstructures at video rates.

Certain microstructures are too small to be visualized using an optical microscope. For imaging microstructures too narrow to be resolved by optical microscopy, such as those expected from some of the surfactants with polypeptide headgroups, transmission electron microscopy (TEM) can be used, such as the TEM of the University of Washington's Medical school Imaging Center. Imaging can be either direct or with a phosphotungstic acid negative stain. Freeze fracture replicas also can be made using a Balzers 360 belonging to the Imaging Center. Additional techniques can be used to characterize the compounds formed, including circular dichroism (CD) and Raman spectroscopy.

Examples 6–13 below illustrate certain methods for forming HAR microstructures, and the morphologies of the structures made.

IV. Stability of HARMs at Physiological Conditions

The stability of the compounds made in accordance with the present invention also has been investigated. HARMs formed as described above were subjected to tests to determine the thermal stability of the compounds at physiological temperatures and physiological pH. Examples 14–15 provide more detail concerning how thermal and physiological-fluid tests were conducted. In general, HAR therapeutics formed in accordance with the present invention were stable at physiological pH and physiological temperatures, particularly those materials having $T_{M_s}$ greater than physiolgoical temperature.

V. Kinetics of Dissolution and Enzymatic Cleavage

There at least two mechanisms for dissolution and enzymatic cleavage of HAR therapeutic agents made in accordance with the present invention. In the first scenario, the HARM comprises an HAR-forming surfactant with a therapeutic coupled to or associated with its headgroup. The surfactant would be a lipidated drug if it were active in its intact form. However, if the therapeutic is released or activated by cleavage, such as enzymatic cleavage, after entering the target cell, then the compounds of the present invention function as lipidated prodrugs. The constant rate of Cylinder dissolution appears to be controlled largely by the solubility of the lipidated drug in the surrounding medium. The greater the ratio of head-group area to hydrocarbon chain surface area, the more rapid will be the dissolution and delivery.

In the second approach, the drug moiety is attached to the HAR-forming surfactant via a cleavable spacer (sometimes referred to as a tether). In general, spacers might be a polypeptide with a sequence known to be susceptible to attack by a protease at the site of use, or a functional group of limited stability against cleavage when exposed to the solution at the site of use. The drugs are packed tightly enough at the surface of the HARM microstructure too prevent access by a protease. Only at the disordered ends of the HARMs would there be access for the enzyme to interact with the HAR microstructures so that the release of the drug would be controlled by the constant number of intact spacers exposed at the advancing front of spacer cleavage. While this approach seems more complex, it allows using a single HARM and spacer for coupling to a wide range of water-soluble molecules, including biomolecules such as polypeptides and nucleic acids.

HARMs, particularly tubules and cochleate structures, generally are crystalline materials and tend to dissolve only from the surfaces and ends thereof, or perhaps from regions of imperfection in the HAR microstructure. The end-dominated dissolution model and lysis was evaluated both theoretically and empirically.

A. Theoretical Evaluation

Theoretical dissolution rates of three structures—a solid sphere, an infinitely long solid cylinder, and a slab were used to model the kinetics for dissolution at HAR microstructures, particularly tubule and cochleate ends. In all cases the dissolution rate is proportional to the exposed surface area. The three are drastically different when considering one particle or a homogeneous population of particles. However, heterogeneity in particle size softens the distinction between the models.

Figure 6:
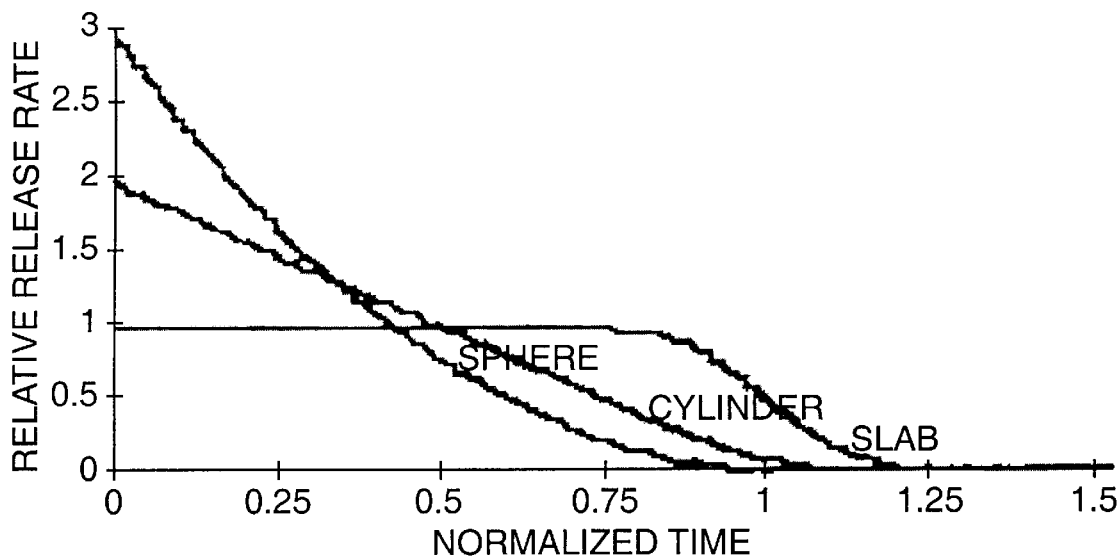
FIG. 6 is a graph that compares the kinetics of dissolution of spheres, infinitely long solid cylinders (no diffusion from the ends) and flat slabs (for modeling dissolution from the ends of tubules).
Figure 7:
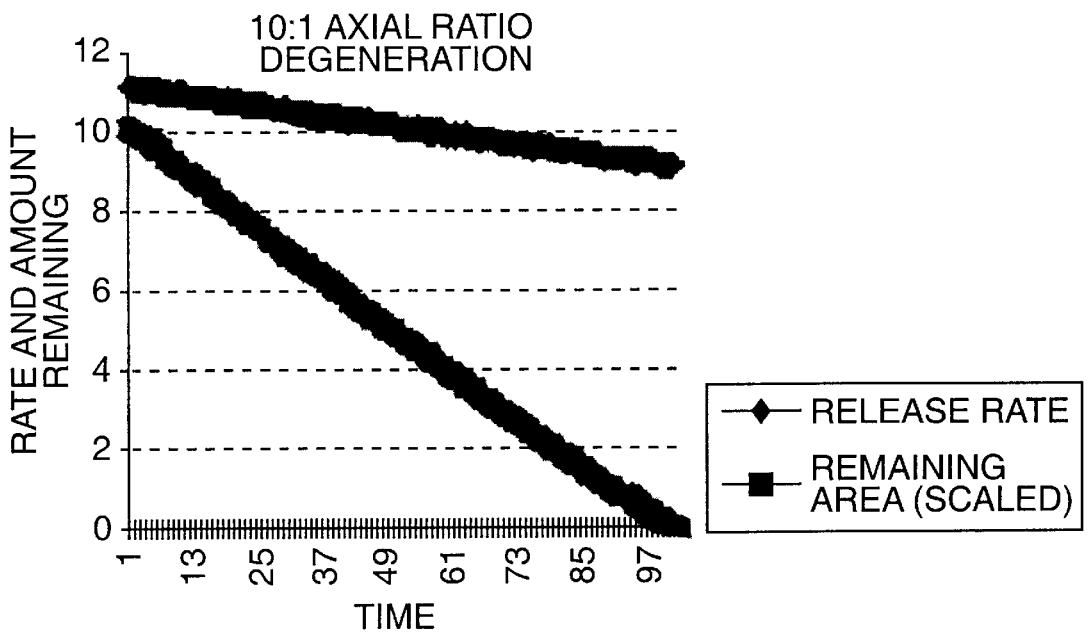
FIG. 7 is a graph illustrating the calculated degradation of a flat sheet having a 10:1 axial ratio that is degrading from its edges at a rate proportional to the length of its edges as a model of the degradation of cochleate cylinders.

As shown in FIG. 6, the nature of the dissolution can be distinguished by the number and position of inflection points in the delivery rate curve. FIG. 6 shows that the relative release rate depends upon the morphology of the system. Both the sphere and the infinitely long solid cylinder exhibited dissolution rates that varied from relative rates of 2 or greater to 0 over the time period tested. On the other hand, the solid slab, which was used to model dissolution from tubules and cochleate structures, had a relative dissolution rate of about 1 over virtually the entire period tested.

The rate of appearance of dissolved surfactant or surfactant breakdown products from tubules appears to remain substantially constant until the number of tubules (and ends)

declines. The rate of drug release to the tissue is limited by the rate of release from the ends of tubules, so that drug release rate generally is constant (0-order), as opposed to the more conventional first-order kinetics found with a wide range of other geometries.

Cochleate cylinders consist of one or more bilayers that have wrapped in a helical manner to form the cochleate microstructure. Cochleate cylinders therefore have two types of "free edges"; those at the microstructure ends, and one or two bilayer edges along the length of the microstructure. As a result, an appropriate model for the dissolution or enzymatic degradation of cochleate cylinders is the unrolled flat sheet that comprises the microstructure. In this model, very long and very short cochleate cylinders both can degrade with kinetics similar to those of the lipid tubules. If the sheet that wraps to form the cochleate cylinder has an axial ratio of about 10:1, there is only an 180 decrease in the hydrolysis or degradation rate before the microstructure is completely hydrolyzed or degraded (if the ratio is greater than 10:1, then the decrease in the hydrolysis rate or degradation rate is concomitantly decreased). As stated above, the cochleate cylinder formed by wrapping such a sheet has an axial ratio of greater than 300 (30 µm in length divided by 0.1 µm in diameter=300). However, if the sheet is nearly square then the rate of hydrolysis or degradation will decrease linearly until the cochleate microstructure is completely hydrolyzed or degraded.

The rate of drug release generally will only be constant to the extent that the HAR microstructure population is homogeneous in length. While it is possible to form HAR microstructures with unimodal length distributions using particular crystallization methods [See, for instance, the crystallization protocol discussed in Yager et al.'s *Helical and Tubular Microstructures Formed by Polymerizable Phosphatidylcholines,* 109:6169–6175 (J. Am. Chem. Soc., 1987)] there is always a distribution of lengths about the mean. Storing the HAR microstructures often results in the smaller HAR microstructures converting to longer ones. It is possible to remove the extremes of the length distribution using filtration and sedimentation.

B. Empirical Studies

1. Proof-of-Principle Experiment

A proof-of-principle experiment was performed on $DC_{8,9}$ PC which is commercially available (Avanti Polar Lipids, Birmingham Ala.). The experiment was performed to prove that tubules could be enzymatically cleaved (and release fatty acid) at a constant rate. The enzyme phospholipase $A_2$ ($PLA_2$) is known to hydrolyze the fatty acid at the 2 position of the glycerol backbone of phospholipids. It is also known that $PLA_2$ only binds tightly to bilayers in the presence of negatively charged lipids such as fatty acids; once some hydrolysis has occurred, the proportion of membrane-bound enzyme increases. $PLA_2$ is known to hydrolyze the well-studied dipalmitoyl phosphatidylcholine (DPPC) below its $T_m$. An experiment was designed to determine whether $PLA_2$ can work on $DC_{8,9}PC$ below its $T_M$ in tubule form.

Figure 8:
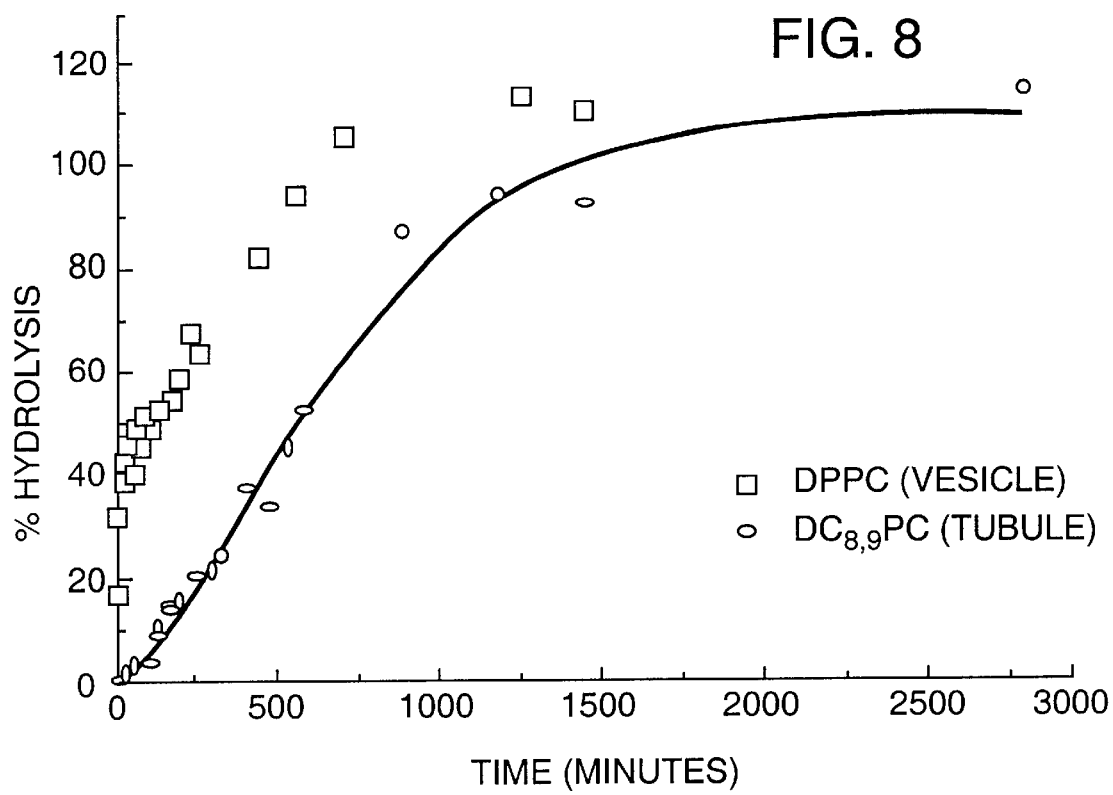
FIG. 8 is a graph of time versus % hydrolysis for suspensions of $DC_{8,9}PC$ tubules and DPPC liposomes by 160 nM cobra venom $PLA_2$.

Small unilamellar vesicles (SUVs) were prepared from 1,2-dipalmitoyl-sn-glycero-3-phosphocholine (DPPC). The $T_M$ of DPPC at 41.3° C. is similar to that of $DC_{8,8}PC$, and is only slightly depressed in SUVs. Because they have identical head groups, comparison of hydrolysis of DPPC vesicles and $DC_{8,9}PC$ tubules allows isolation of those effects unique to a tubular microstructure. FIG. 8 shows the progress curves for the hydrolysis of 0.5 mM dispersion of DPPC SUVs and of multi lamellar $DC_{8,9}PC$ tubules at 30° C. by 2.24 µg/ml $PLA_2$ as determined by the production of free fatty acid. The hydrolysis progress curve for the control SUV dispersion of DPFC was biphasic, as expected. An initial rapid hydrolysis stage, which ends after roughly 50% of the total lipid has been hydrolyzed, is followed by a period of slower, nearly constant hydrolysis. In a unilamellar liposome, only the outermost layer is initially accessible to enzyme. The rapid initial hydrolysis rate of 0.88 $s^{-1}$ reflects the hydrolysis of lipids in the other monolayer. The onset of the subsequent slower hydrolysis stage is caused by substrate depletion in the outer monolayer. Hydrolysis proceeds to completion at about 0.044 $s^{-1}$, limited by access to new substrate either from the bursting of partially hydrolyzed vesicles or from slow phospholipid flip-flop between the inner and outer vesicle monolayers.

The progress of tubule hydrolysis is markedly different. After a 120 minute lag, the hydrolysis proceeds with a slow, nearly constant rate of 0.041 $s^{-1}$ for most of the reaction. The rate of hydrolysis of tubules after the initial lag is 20 times slower that for the outermost DPPC vesicle monolayer, and, in contrast to all other reported $PLA_2$ reaction profiles, it remains constant after the initial lag until nearly 100% hydrolysis. This constant hydrolysis rate is consistent with end-dominated tubule hydrolysis.

However, the microstructures observed by TEM reflect a more complex process. Shortly after addition of enzyme, helical ribbons emerging from what appear to be fractured tubules are visible. Even though a few intact tubules are still present at the 50% hydrolysis point, the types of microstructures present include small filaments, helical ribbons, and elongated sheets. Tubules appear to remain intact until certain fraction of reaction products is reached within a local region of the tubule bilayer. The point when product accumulation can no longer support the specific asymmetric curvature required to form a one micrometer diameter tubule, the product regions fracture and unwrap to form smaller helices, filaments and flat sheets.

Moreover, fluorescent dye studies have been completed, wherein the cationic fluorescent dye 1,1,3,3,3',3'-hexamethyl-indocarbocyanine iodide was added to visualize the region of negative charge accumulation. Early in the reaction, fluorescent regions appear at several points along intact tubules. Hydrolysis, therefore is not limited to tubule ends. Instead, local defects in molecular packing within the bilayer appear to function as initiation sites for hydrolysis.

Fluorescent $PLA_2$ also has been used to track reaction progress. 5-carboxyfluorescein-tagged $PLA_2$ was used. Immediately after addition, enzyme appears to distribute uniformly over the tubule surface. By the completion of hydrolysis, the product microstructures show strong fluorescence, which implies enhanced $PLA_2$ binding to product-risk microstructures.

Although enzyme reaction with tubules is not limited to reaction at the end of tubules, the reaction progress nevertheless is still more constant and slower than that of SUVs. This makes the tubules attractive drug delivery agents.

2. Detergent Dissolution Kinetics Bile salts occuring naturally in humans act similarly to detergents. Thus, the kinetics of HAR microstructure dissolution in detergents is; a good model for the oral administration of therapeutics and vaccines for delivery to the gastrointestinal tract. The kinetics of dissolution in detergent solutions has been investigated. The commercially-available tubule-forming phospholipid 1,2-bis(10,12-tricosadiynoyl)-sn-glycero-3-phosphocholine ($DC_{8,9}PC$) and the non-ionic detergent octyl β-D-glucoside (OG) were used as the model system. Upon precipitation from ethanol, $DC_{8,9}PC$ forms multi-lamellar tubules with an average diameter of 0.75 µm, a length distribution ranging from 30–50 µm, and a melting temperature ($T_m$) of 43.8° C. The tubule morphology is composed of helically-wrapped lipid bilayers that close to form straight, hollow, rigid tubes. Tubules can appear, however, in the presence of minority structures such as open helical ribbons. If given time to anneal, the lipids form closed and uniform tubules. Presumably, the tight crystalline packing of the tubule wall will hinder release of monomeric lipid from the microstructure and insertion of detergent into the tubule except at regions of defects in the crystalline packing such as must occur at tubule ends c)r at "helical" defects.

Figure 9:
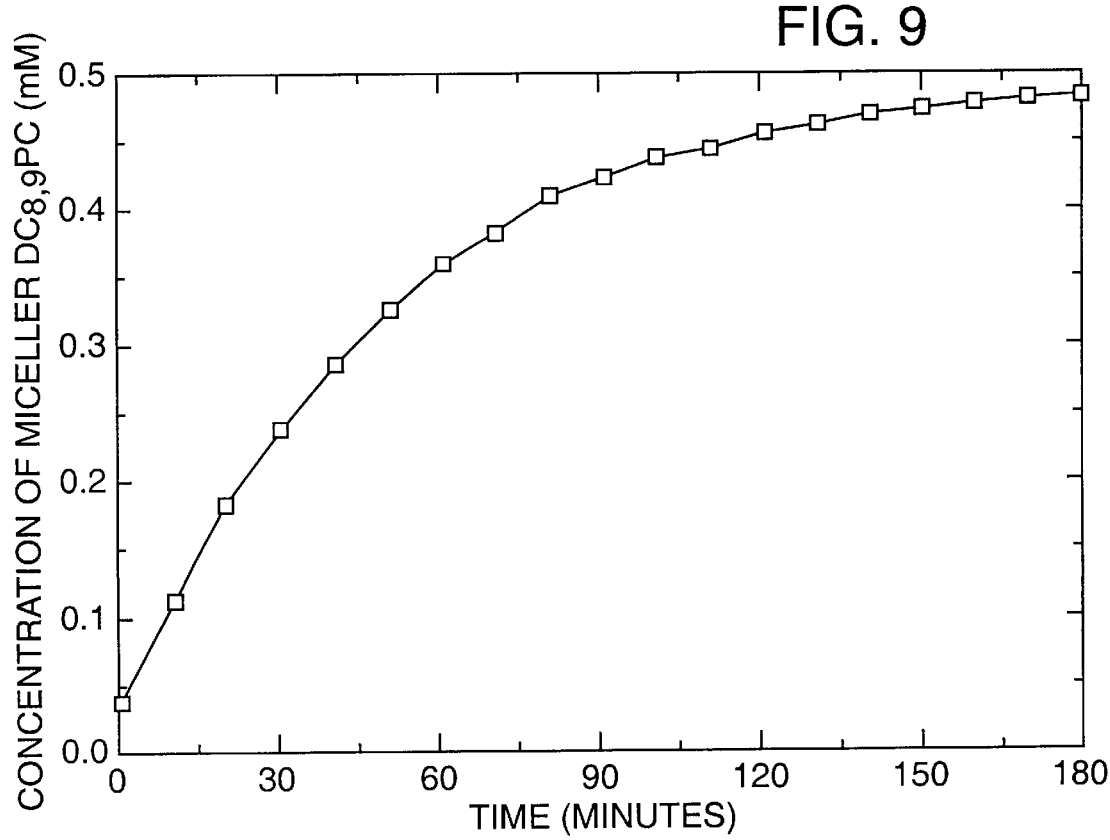
FIG. 9 is a graph of time versus concentration of micellar $DC_{8,9}PC$ illustrating the time course for the solubilization of a 0.5 mM suspension of $DC_{8,9}PC$ lipid tubules in the presence of 50 mM OG.
Figure 10:
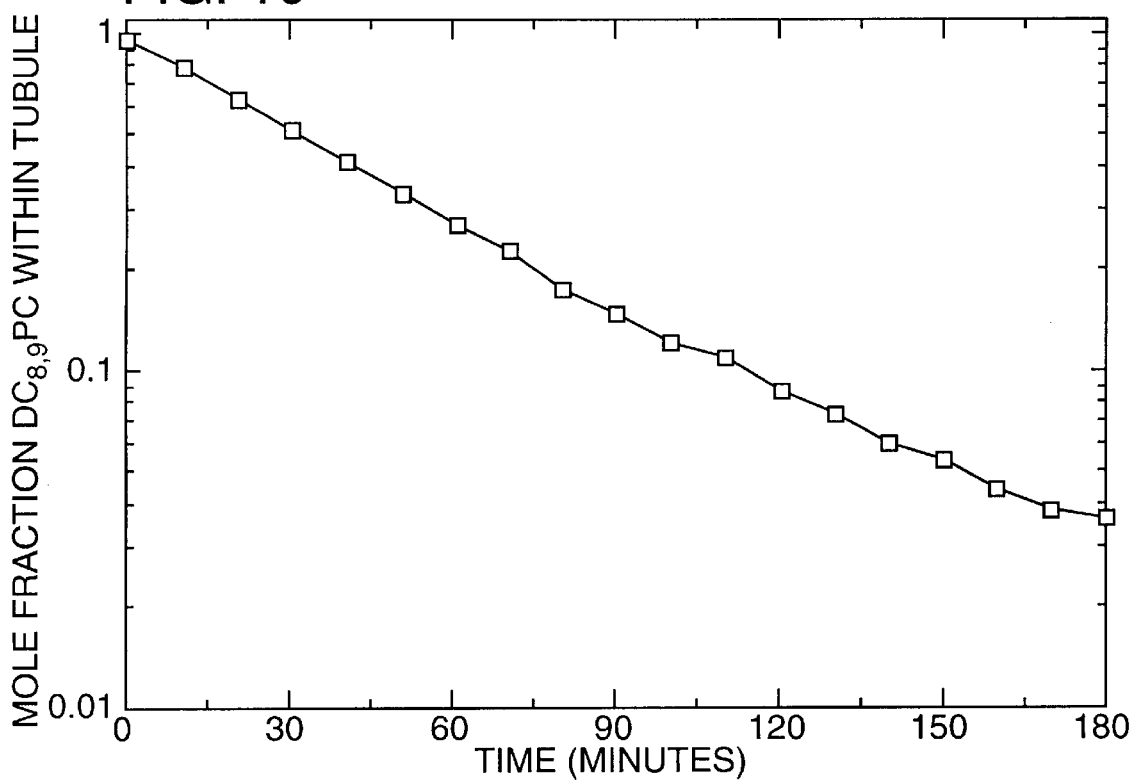
FIG. 10 is a graph of time versus the mole fraction of $DC_{8,9}PC$ remaining in tubule microstructures as a function of time.

FIG. 9 shows the concentration of $DC_{8,9}PC$ solubilized into OG detergent micelles as a function of time. To start solubilization, an aqueous suspension of $DC_{8,9}PC$ tubules was added to an aqueous suspension of OG detergent micelles to create a final solution having a 0.5 mM concentration of $DC_{8,9}PC$ and a 50 mM concentration of OG. The reaction vessel was at room temperature (approximately 21° C.). Tubule microstructures were much larger than detergent micelles so a 0.2 µm filter was used to separate the two phases prior to analysis. $DC_{8,9}PC$ absorbs strongly from 190 to 254 nm because of the diacetylene groups present in the hydrocarbon tails. The amount of micellar $DC_{8,9}PC$ was determined with a UV-Vis spectrometer by calculating the second derivative of the optical density with respect to wavelength at 250 nm, which was a mathematical step that reduced errors introduced from scattering artifacts. The concentration could be determined by comparing this value to those obtained from a calibration curve. Throughout the course of solubilization, aliquots of the suspension were removed, passed through a 0.2 µm filter, and assayed for the amount of solubilized $DC_{8,9}PC$. FIG. 10 shows the mole fraction of $DC_{8,9}PC$ remaining within a tubule as a function of time and depicts the nature of the solubilization process. The logarithm of the $DC_{8,9}PC$ tubule concentration depends linearly with time, which suggests that tubule disintegration is a first order process. Furthermore, changes in solution turbidity, as determined by measuring the optical density at 400 nm, correlates well (e.g. linearly) with the amount of $DC_{8,9}PC$ within the tubule.

Figure 11:
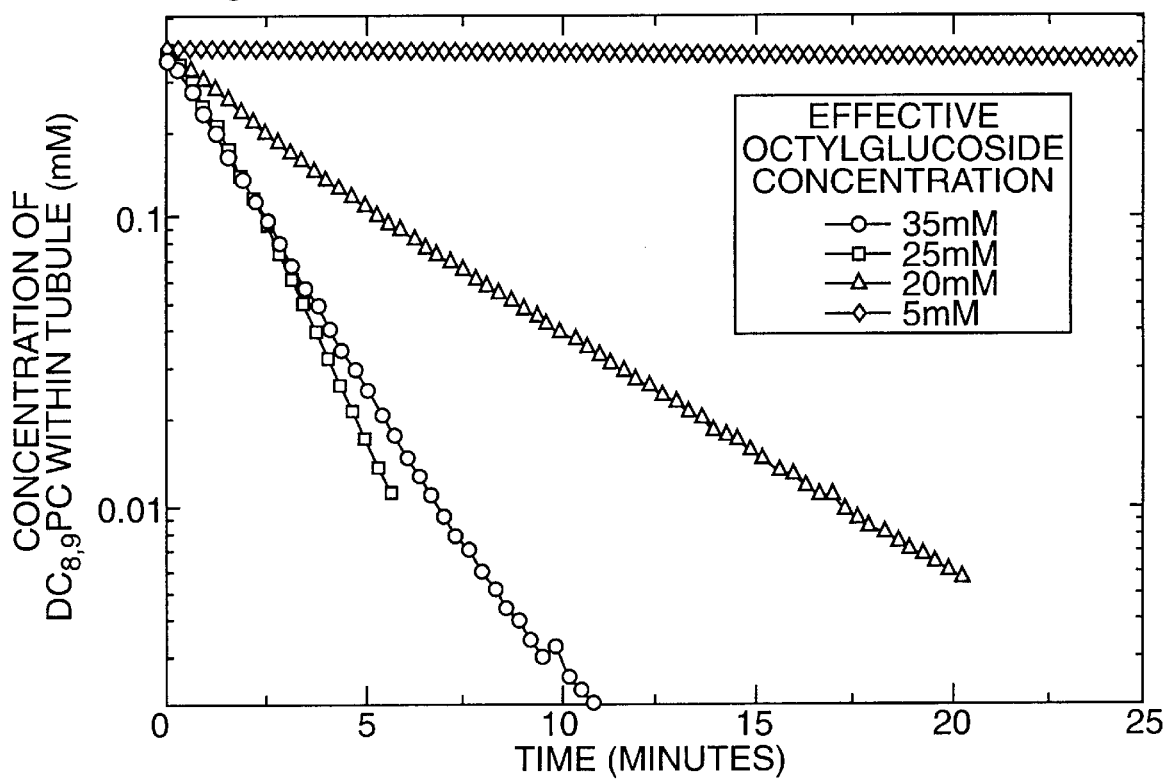
FIG. 11 is a graph of time versus concentration of $DC_{8,9}PC$ within tubules (mM) for various concentrations of solubilizng detergent.

Multilamellar PC tubules, L, interact with detergent, OG, to form mixed micelles, M. If, however, the effective concentration of detergent that is available for solubilization does not change throughout the course of the reaction (e.g. detergent is not consumed by the reaction, mixed micelles can contain many phospholipids, etc.), then the kinetics can be described as a first order process. If this view is correct, then the effective rate constant, $k_1$, should depend linearly on the concentration of detergent (e.g. $k_1 = k_2$ [OG]). FIG. 11 shows the time course of solubilization as a function of OG concentration. An estimate for the value for the second order rate constant, $k_2$, can be determined from the slope of the line created when the measured first-order rate constant $k_1$, is plotted against detergent concentration.

$$k_2 = 0.124 \pm 0.012 \text{ mol}^{-1}\text{s}^{-1}$$

Figure 12:
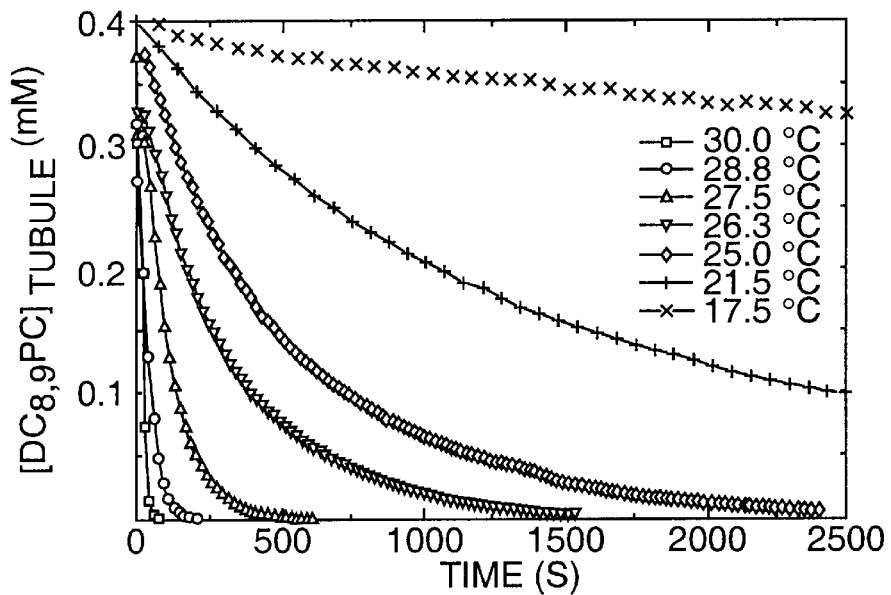
FIG. 12 is a graph of time versus concentration of $DC_{8,9}PC$ within tubules (mM) illustrating the temperature dependence on the concentration of $DC_{8,9}PC$ within tubule microstructures.
Figure 13:
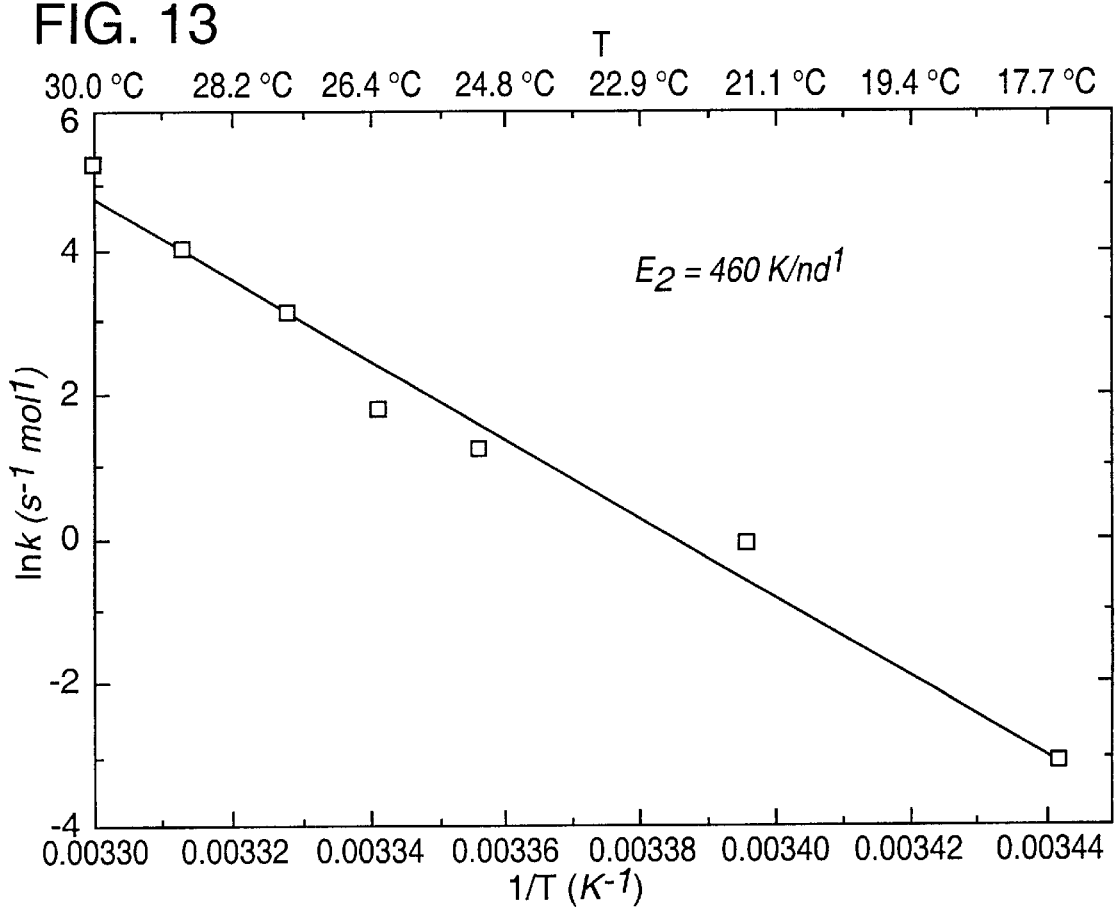
FIG. 13 is an Ahhrenius plot of the solubiliztion rate versus inverse temperature.
Figure 15:
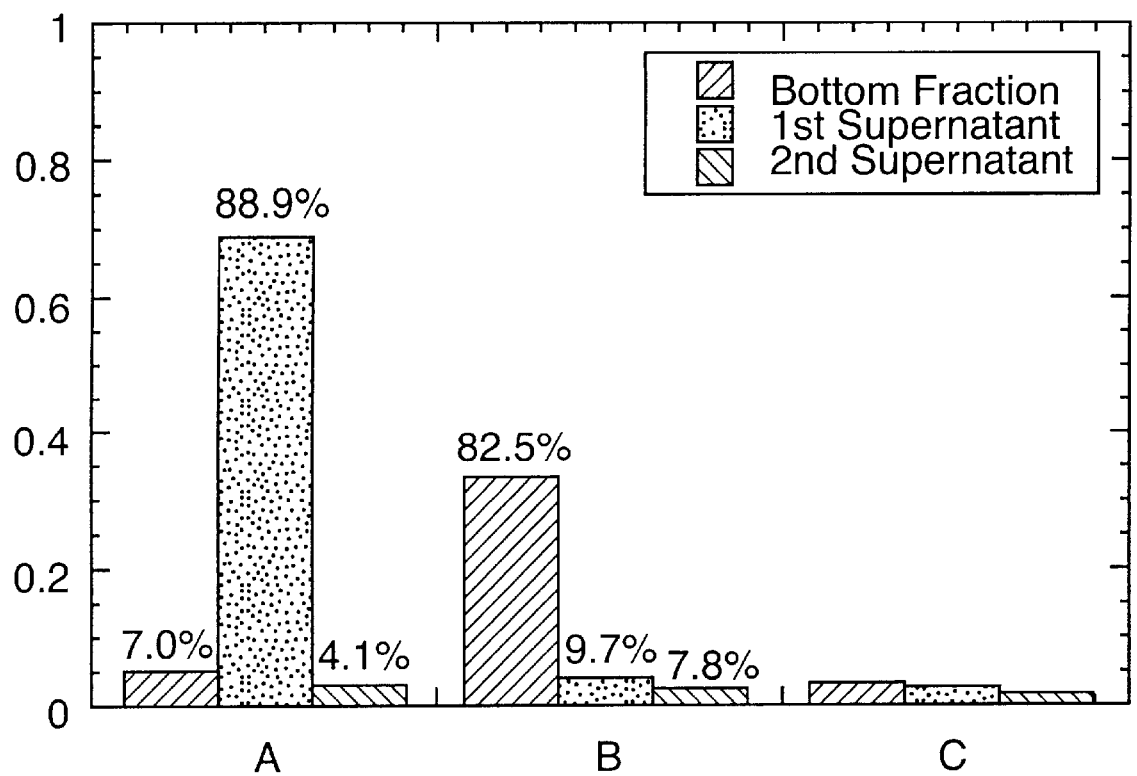
FIG. 15 is a graph of DNA absorbance at 260 nm for the bottom fraction, and first and second supernatant samples produced by centrifuging A) 200 μg/ml DNA, no lipopeptide, B) 200 μg/ml DNA, 0.4 mM $(Pro)_3$-Glu $(NHC_{16}H_{33})_2$, and C) 0.4 mM $(Pro)_3$-Glu$(NHC_{16}H_{33})$

Temperature strongly affects the rate of HAR solubilization. FIG. 12 shows the concentration of $DC_{8,9}PC$ within a tubule as a function of time as determined from measuring the O.D. at 400 nm. A solution containing a 100-fold molar excess of OG (40 mM) was added to a stirred quartz cuvette and placed in a temperature-controlled UV-Vis spectrometer. Once the detergent suspension had reached thermal equilibrium, an aqueous suspension of $DC_{89}PC$ tubules (0.4 mM) was quickly added. The temperature dependence of the rate of tubule solubilization was determined by measuring the decrease in turbidity (e.g. changes in O.D.) with time. As shown in FIG. 15, the kinetics of solubilization were strongly temperature dependent and first order. FIG. 13 is an Ahhrenius plot of the solubilization rate constant that shows the energy barrier to solubilization is high, $E_{act}$=460 kJ mole$^{-1}$.

The microstructural form into which phospholipids self-assembly does not appear to influence the kinetics of detergent solubilization. Egg PC vesices also show first order kinetics (Mimms, et al., 1981). The rates are very sensitive to the aggregation "state" of the phospholipid, and under these circumstances the right crystalline packing in tubules may be advantageous for slow solubilization of the drug by bile salts and other biological detergents.

VI. Administering the Composite Compounds

HAR microstructures are used for the continuous administration of ligands to organisms, including both plants and animals, particularly mammals such as humans. HAR microstructure-based continuous release can be used for administering therapeutics, for example and without limitation, topically, orally, intramuscularly, intranasally, subcutaneously, intraperitoneally, intralesionally, intravenously, or any other administration means now known or hereafter developed that allows for the compounds to remain in HAR microstructures. Moreover, the safety and comfort of the patient also must be considered. Larger diameter HAR microstructues (about 1 µm diameter) may be too large for injecting into the circulatory system because of the potential to clog capillaries. All other internal and external sites of drug delivery are possible, however, for those HAR microstructures having diameters greater than about 1 µm. And, for HAR microstructures having diameters less than about 1 µm, injection into the circulatory system can be used to administer the therapeutic/HARM complexes.

Moreover, most of the tubule mass is :n the wall. This means that there is a large "wasted" central lumen in the tubules, which reduces the possible drug loading. Multi-bilayer tubules or cochleate cylinders thus are well suited for circumstances where high drug loading is necessary. Smaller and more flexible tubules and cochleate cylinders have less wasted space and also may be small enough to pass through the capillary beds. HAR-microstructure-based therapeutic delivery systems can provide controlled release in topical or subcutaneous applications. The relatively long length of some of the microstructures immobilizes them without using a rigid polymeric matrix. HAR microstructures also can be used in mucosal and oral delivery. The tight packing of the lipid molecules in the HAR microstructure could afford protection of certain drugs such as peptides from the premature enzymatic hydrolysis that now plagues peptide delivery systems as has been shown for calcium-induced cochleate cylinders. While there are often ample concentrations of proteolytic and lipolytic enzymes present in the interstitial fluid in vivo, these enzymes are often inhibited to prevent uncontrolled cell damage. To ensure that the therapeutic will be enzymatically released from the HAR microstructures in an extracorporeal site, such as in topical applications or in vitro, HAR microstructures can be co-suspended with hydrolytic enzymes.

While there is nothing inherently antigenic about a lipid HAR microstructure, subcutaneous injection of some drug-coated HAR microstructures might be used to induce an inflammatory response, as demonstrated by the adherence of some cells to $DC_{8,9}PC$ cylinders. The cellular environment in the presence of such a response provides ample proteolytic enzymes to cleave prodrugs from the HAR microstructure surfaces, which could be an advantage. Some vaccination protocols require repeated dosing with vaccines because a single bolus dose does not raise an adequate immune response. HAR microstructures placed in subcutaneous sites could act as long-acting vaccines that deliver antigen long enough to create a strong immune response. Because the rate of degradation of lipidated drugs depends on whether the surfactant morphologies are HAR microstructures or liposomes, raising the local temperature above $T_m$, which converts the HAR microstructures to liposomes, provides a method for greatly increasing the delivery rate from implanted microstructures on demand.

Even if in vivo use of HAR microstructures is restricted for some reason, continuous therapeutic release using HAR microstructure is still important in such in vitro applications where delivery of some chemical is required over a long period of time at a constant rate. A biotechnologically important example is the delivery of growth factors or antibiotics to cells being cultured in containers too small to merit continuous infusion of such factors.

In order to provide steady, continuous therapeutic release, the rate of dissolution or enzymatic cleavage of the therapeutic from the HAR microstructures must be relatively constant. This steady, continuous therapeutic release has been confirmed using a variety of methods.

VII. Dosage-range Studies in Animals

Dose ranges for drug delivery complexes made in accordance with the present invention also have been conducted. Male Balb C mice, 18–22 grams, 3–12 months, were used for the study. Balb C mice were selected because they (1) historically have been used for such test, and (2) are a reliable indicator for assessing potential drug toxicity.

One compound tested was $Pro_3$-glutamic acid didodecylamide [$(Pro)_3$-Glu $(NHC_{16}H_{33})_2$=$(Pro)_3$-Glu] $Pro_3$-glu was administered to test animals in an aqueous solution comprising 120 nM NaCl at a pH of 7.2. Controls also were used for these and similar studies. The control for this particular study was 120 mM NaCl at a pH of 7.2.

13 mice were used, divided into three groups (1 group of three animals, and 2 groups of 5 animals). The rear flanks of the animals were shaved prior to receiving injections. The group 1 animals received a single 250 $\mu$l injection of the control, and were euthanised at 15 days. The group two and three animals received a single 250 $\mu$l control injection at a first site, and a 250 $\mu$l injection, 100 $\mu$g of the test material, at a second site. The group two animals were euthanised at eight days, and the group three animals were euthanised at 15 days. The health of the animals was monitored daily.

Histology analysis was performed on tissue collected from the injection sites and preserved in 10% neutral buffered formalin solution. Cross sections from skin injection sites and surrounding tissue were procesed by normal paraffin embedding and staining by Hematoxylin and Eosin.

The health of the 13 animals in the study were normal throughout the study, and there were no consistent changes in body weight throughout the study. Histopatholigcal evaluation showed mild incidence of dermatitis, folliculitis and perifolliculitis. However, these effects likely were the result of trauma caused by shaving or injection, and not some negatives reaction to the injected materials. The study indicated that there was no gross toxicity associated with the tested material.

VIII. Transfection Studies in Animals

Protein encoding plasmids, such as the green fluorescent protein encoding plasmid pEGFP—N1 and the breast cancer endocing plasmid pcDNA3HumHer2 Neu(pCXI), can be incorporated into HARMs such as $(Pro)_3$-Glu$(NHC_{16}H_{33})_2$ and $(Pro)_3$-Glu $(NHC_{12}H_{25})_2$ HARMs. These plasmid-HARMs have been used to transfect cells in different organs and tissues. None of the mice treated with these DNA plasmid-HARMs have died from the treatment. For example, of 15 mice injected with pEGFP-N1/$(Pro)_3$-Glu $(NHC_{16}H_{33})_2$ complex (50 $\mu$g of DNA, 250 $\mu$g of lipopeptide in 100 $\mu$l of HBS) none died before the sample collection time, which was up to two weeks post injection. This demonstrates the absence of acute toxicity of the DNA-HARM complexes. Specific data from animal transfection studies are reported below in Examples 23 and 25.

IX. EXAMPLES

The following examples are provided to illustrate particular features of the present invention. The examples should not be construed to limit the scope of the invention to the specific aspects described.

EXAMPLE 1

This example describes the synthesis of glutamine-based amphiphiles using hexadecylamine to form dihexadecyl glutamides. The synthesis described can gnerally be used for the synthesis of a variety of compounds wherein the length of the side chains is varied.

In general, the following methods were followed in the synthesis of compounds in accordance with the present invention. All chemicals and solvents from commercial sources were reagent grade. Al reactions were carried out under an inert atmosphere, such as an argon atmosphere, with the exception of the acetylation which was done in a manual solid peptide synthesis vessel. All amino acids used were of L-configuration. Thin layer chromatography (TLC) was done using silica gel6O $F_{254}$ from EM Science. The spots were visualized using 0-tolidine, ninhydrin, or both. Flash chromatography was done using silica gel6O (230–400 mesh) also from EM Science. The reported yields represent actual amounts recovered after purification. $H^1$ NMR spectra were recorded on Brucker 300 mHz NMR-spectrometers. HPLC were done on Rainin Dynamax solvent delivery system or Perkin-Elmer Series 400. Mass spectra(ES-MS) were taken on Kratos Profile HV-4 with electrospray ionization source, at the University of Washington mass spectrometer lab. Samples were mixed with 1:1 methanol and water containing 1k acetic acid.

The first step in the synthesis of dihexadecyl glutamides involved forming an activated ester from glutamic acid with the amino group protected with a CBZ protecting group. This allows the activated ester to be coupled with hexadecylamine. In the present example, N-hydroxysuccinimide was used to activate thee ester.

5.0 grams of glutamic acid protected with a CBZ protecting group (referred to as Z-glutamic acid) was dissolved in 100 ml of dry THF. 4.64 grams of N-hydroxysuccinimide (1.1 equivalents; 2.2 molar equivalents) were added to the solution, which was then cooled to about 0C using an ice/methanol bath. 7.69 grams of 1,3-dicyclohexylcarbodiimide (DCC; 1.05 equivalents) were added, followed by stirring at about 0C for 2 hours. The solution was then allowed to warm up slowly with stirring overnight. DCU (dicylohexylurea, which forms as a byproduct of the reaction) was then removed by filtration tc give an oily solid. 150 milliliters of ethyl acetate were added to precipitate more DCU, which was then removed by filtration. 50 milliliters of ethyl acetate were then added, and the solution was washed with saturated $NaHCO_3$. brine and water, followed by drying over sodium sulfate. The mixture was then filtered, and concentrated in vacuo. The concentrated product was then tritiated with ethyl ether to provide a white powder corresponding to the di-N-hydroxysuccinimide ester. 300 mHz H$^1$ NMR showed that the product was substantially pure (all structures of the products made according to the present invention were confirmed by 300 MHz $^1$H NMR).

The di-N-hydroxysuccinimide-Z-glutamic acid ester was then ready for coupling with an amine. 1.0 (0.10 mmoles) gram of the di-N-hydroxysuccinimide-Z-glutamic acid ester was dissolved in 25 ml of chloroform. 1.1 equivalents of hexadecylamine (available commercially) were added to the solution with stirring for about twenty fours. The resulting solution was washed with saturated sodium bicarbonate, brine, and dried over sodium sulfate. Diethyl ether was added to precipitate a solid. The solid was resuspended in ethyl acetate, and the semi-solid product was filtered, washed (3×) with ether, and dried. The product was purified using a silica gel column, the eluting solution comprising chloroform-5% methanol. This provided compounds comprising the hexadecylamine side chains coupled to the glutamic acid core, but with the CBZ protecting group still intact.

25 grams of the CBZ-protected compound were then dissolved in 2 ml of trifluoroacetic acid (TFA). 3 ml of 30% HBr were added, and the solution was stirred at room temperature for two hours. The solution was filtered and washed with acetic acid. The resulting product was resuspended in ethyl ether and filtered, and then dried in vacuo to produce the bromide salt. The free amine was produced by first dissolving the product in chloroform, adding saturated sodium bicarbonate, followed by filtration and drying in vacuo.

In a manner similar to that described above, related compounds have been synthesized by varying the length of the amine side chains. For instance, the same protocol can be used to synthesize the compounds shown above in Table 1 by substituting, for example, dodecyl amine and tetradecylamine for hexadecylamine.

EXAMPLE 2

This example describes coupling a tetrapeptide to a glutamine-based lipid, which can be produced as discussed above in Example 1. A tetrapeptide (boc-gly-lys-ε-CBZ-sar-pro) was purchased from Anapec of St. Jose, Calif. The tetrapeptide was purified using a silica gel column and a chloroform:methanol:acetic acid (9:1:0.2) elutant system. The product was collected and then extracted with methylene chloride. 70 mg of the tetrapeptide (1.05 equivalents) were dissolved in 200 µl of dry N,N-dimethylforriamide (DMF). 1.0 equivalent of C-12 glutamine lipid shown in Table 2, synthesized as stated above, was dissolved in 2.0 ml of DMF and added to the solution containing the tetrapeptide. The resulting solution was cooled to about 0C. 1.1 equivalents of diethyl phosphorylcyanate were dissolved in about 200 microlitters of DMF and then added to the solution, followed by about 1.1 equivalents of triethylamine. The solution was stirred at about 0° C. for about 2 hours, followed by stirring at room temperature for about 48 hours. 75 ml of chloroform were then added to the solution, followed by washing with 10% citric acid, 5% sodium bicarbonate, brine and water. The solution was filtered, and concentrated in vacuo. The product was purified using a silica gel column, eluting with chloroform-2.5% methanol. 60 mg of the protected tetrapeptide-lipid were then dissolved in 800 µl of methylene chloride. The solution was then cooled to about 0° C. 2 ml of HCl,'dioxane (4 molar) were added to the solution. The solution was kept at 0° C. for about 2 hours. The solution was then concentrated in vacuo. A fraction of the product was purified using an analytical C-4 HPLC column, using acetonitrile/water/0.6% TFA. The product produced was the salt of the amine.

The free amine was liberated by dissolving 45 mg of the tetrapeptide-lipid in 1 ml methylene chloride, 9 ml 30% HBr/acetic acid, followed by stirring at room temperature for 2 hours. The product was then concentrated, followed by lyophilization from water. A fraction of the product was purified using an analytical C-4 HPLC column with acetonitrile/water/0.6% TFA.

In a manner similar to that described in Example 2, additional peptides and single amino acids derivatives, such as proline derivatives, also have been made. For instance, proline with an FMOC protecting group has been coupled to the C-12 glutamine lipid shown in Table 1 using EDC, the water-soluble derivative of DCC).

EXAMPLE 3

This example concerns the synthesis of cylinder forming molecules having peptide spacers coupled thereto, wherein the spacer incudes an enzyme cleavage site.

Nα-Glycyl-Nv-(2,2,5,7,8-pentamethylchromane-6-sulfonyl)-arginyl-alanyl-glycyl-glycyl-alanyl-alanyl-prolyl-prolyl-prolyl-2-chlorotrityl resin was purchased as a custom order from the University of Washington immunology biopolymer facility.

Nα-Glycyl-Nω-(2,2,5,7,8-pentamethylchromane-6-sulfonyl)-arginyl-alanyl-glycyl-glycyl-alanyl-alanyl-prolyl-prolyl-prolyl-2-chlorotrityl resin (200 mg) was washed with CH$_2$CL$_2$ and reacted with acetic anhydride (41.5 µl, 0.44 mmol) and diisopropylethylamine (95.8 µl, 0.55 mmol) in CH$_2$CL$_2$ for 2 hrs. in a manual solid phase peptide synthesis vessel on a rocker for 2 hrs. The peptide resin was washed with CH$_2$CL$_2$ three times and dried in vacuo to produce Nu-Acetyl-glycyl-Nω-(2,2,5,7,8-pentamethylchromane-6-sulfonyl)-arginyl-alanyl-glycyl-glycyl-alanyl-alanyl-prolyl-prolyl-prolyl-2-chlorotrityl resin. The Kaiser test was negative.

Nα-Acetyl-glycyl-Nω-(2,2,5,7,8-pentamethylchromane-6-sulfonyl)-arginyl-alanyl-glycyl-glycyl-alanyl-alanyl-prolyl-prolyl-prolyl-2-chlorotrityl resin (80 mg) was treated with 1:1:8 acetic acid:trifluoroethanol:CH$_2$CL$_2$ (2 ml) at room temperature for 30 min. After filtration of the cleaved peptide, the resin was retreated with the same cleavage mixture for 30 min. The combined filtrates were evaporated, dissolved in H$_2$C, and dried in Speed-Vac. The residue was purified by Vydac 218TP1010 column using 35% isocratic acetonitrile:H$_2$C containing 0.06% TFA and 4 ml/min. flow. The product, Na-Acetyl-glycyl-Nu-(2,2,5,7,8-pentamethyl-chromane-6—sulfonyl)-arginyl-alanyl-glycyl-glycyl-alanyl-alanyl-prolyl-prolyl-proline, eluted at 30 min yielded 2:2.8 mg after lyophylization. TLC$_{butanol:acetic\ acid:H2O\ (4:2:2)}$: Rf 0.49. ES-MS: [M+H]$^+$ 1159.0 calcd 1159.35, [M+Na]$^+$ 1181.1 calcd 1181.34, [M+H+K+]$^{2+}$ 599.3 calcd 599.05.

α,γ-ditetradecyl glutamide, synthesized as stated above, in CHCL$_3$ (500 µl) was added to a solution comprising DMF (400 µl) and Nα-acetyl-glycyl-Nω-(2,2,5,7,8-pentamethylchromane-6-sulfonyl)-arginyl-alanyl-glycyl-alanyl-alanyl-prolyl-prolyl-proline (10 mg, 8.63 µmol). The resulting mixture was cooled to 0° C. Diethylphosphorocyanidate (1.55 mg, 9.50 µmol) in DMF (15 µl) followed by triethylamine (1.32 µl, 9.50 µmol) in DMF (15 µl) were added and the mixture stirred at 0° C. and allowed to warm up to room temperature slowly. 48 hours later, the reaction mixture was diluted with CHCL$_3$ and washed with saturated NH$_4$CL, H$_2$O, saturated NaHCO$_3$, H$_2$O, brine, dried under Na$_2$SO$_4$, filtered, evaporated, and dried in vacuo. The product, α,γ-ditetradecyl Nα-acetyl-glycyl-Nω-(2,2,5,7,8-pentamethylchromane-6-sulfonyl) -arginyl-alanyl-glycyl-glycylalanyl-alanyl-prolyl-prolyl-prolyl-glutamide, was further purified by silica gel flash chromatography with CHCL$_3$:MeOH (14–20%) to give 57%. TLC$_{CHCL3:MeOH\ (85:15)}$: Rf 0.29.

α,γ-Ditetradecyl Nα-acetyl-glycyl-Nω-(2,2,5,7,8-pentamethylchromane-6-sulfonyl)-arginyl-alany-glycyl-glycyl-alanyl-alanyl-prolyl-prolyl-prolyl-(glutamide (7.80 mg, 4.65 μmol) was stirred with 95:1 TFA:H$_2$O (1 ml) for 2 hours at room temperature, the solvent evaporated, and dried in vacuo. Ethyl ether was added to the residue and the product was triturated to give white solid. The solid was isolated by decantation, washed with ether several times, and further purified by reverse phase HPLC column Vydac 214TP1010 using methanol:H$_2$O containing 0.06% and 0.07% TFT, respectively, with 80% to 100% methanol gradient in 30 min. The product (α,γ-Ditetradecyl Nω-acetyl-glycyl-arginyl-alanyl-glycyl-gylcyl-alanyl-alanyl-prolyl-prolyl-prolyl-glutamide trifluoroacetate), eluting at 92% methanol, was lyophilized from H$_2$O to give 3.8 mg, 54%. TLC$_{butanol:acetic\ acid:H2O\ (4:1:1)}$: Rf 0.27 ES-MS: [M+H]$^+$ 1412.6 calcd 1412.89, [M+2H]$^{+2}$ 706.9.

EXAMPLE 4

This example describes the synthesis of radiolabelled materials, particularly α,γ-Dihexadecyl [5-$^3$H] prolyl-prolyl-prolyl-glutamide hydrochloride. To a solution of [5-$^3$H]proline in 1 mM HCL (1 mCi, specific activity of 15 Ci/mmol), proline (11.50 mg) was added followed by dioxane and NaOH (4.0 mg, 99.9 μmol). The mixture was cooled to 0° C., di-tert-butyl di carbonate (24.0 mg, 109.9 μmol) was added and stirred at room temperature overnight. The reaction mixture was diluted with H$_2$O, washed with hexane, CH$_2$CL$_2$ added at 0° C., acidified to pH 1 to 2 with 1N HCL, extracted with CH$_2$CL$_2$, washed with H$_2$O, dried under Na$_2$SO$_4$, filtered, evaporated, and dried in vacuo to give a 65% yield of Nα-tert-butoxycarbonyl-[5-$^3$H] proline. TLC$_{CHCL3:MeOH\ (9:1)}$: Rf 0.25.

To a solution of α,γ-dihexadecyl prolyl-prolyl-glutamide hydrochloride (48.8 mg, 59.14 μmol) in CHCL$_3$ (30 ml), Nα-tert-butoxycarbonyl-[5-$^3$H]proline (14.0 mg, 65.06 μmol) was added followed by hydroxybenzotriazole (8.8 mg, 65.06 μmol). The mixture was cooled to 0° C. and 1-(3-dimethylaminopropyl) -3-ethylcarbodiimide hydrochloride (12.47 mg, 65.06 μmol) followed by diisopropyl-ethylamine were added, and stirred for 45 minutes at 0° C. before allowing it to warm up to room temperature overnight. The reaction mixture was diluted with CHCL$_3$ and washed with saturated NH$_4$CL, H$_2$O, saturated NaHCO$_3$, H$_2$O, brine, dried over Na$_2$SO, filtered, evaporated, and further purified by silica gel flash chromatography with CHCL$_3$ :MeOH (97.5:2.5): to give a 93% yield of α,γ-Dihexadecyl Nα-tert-butoxycarbonyl-[5-$^3$H] prolyl-prolyl-prolyl-glutamide. TLC$_{CHCL3:MeOH\ (9:1)}$: Rf 0.49.

α,γ-Dihexadecyl Nα-tert-butoxycarbonyl-[5-$^3$H]prolyl-prolyl-prolyl-glutamide was deprotected by dissolving in dichloromethane, followed by addition of 4M HCl/dioxane. The mixture was stirred for 2 hours, the solvent evaporated and the product purified to provide 100% yield of α,γ-dihexadecyl [5-$^3$H]prolyl-prolyl-prolyl-glutamide hydrochloride. TLC$_{butanol:acetic\ acid:H2O\ (4:1:1)}$: Rf 0.43. Cospotting, this material with the unlabeled compound on TLC plate showed a single co-migrating spot.

Fluorophores and tritiated acetyl groups can be coupled to the terminal amino group of polypeptides bound to molecules capable of forming cylindrical lipid microstructures. This allows the detection of therapeutics, such as polypeptides, once they have been released from the cylindrical microstructure.

One example of a suitable fluorophore is O-aminobenzoic acid. The O-aminobenzoic acid first was protected with a BOC protecting group using known chemistry to produce BOC-aminobenzoic acid. This protected fluorophore was then coupled to the tetrapeptide derivative as produced in Example 2 using EDC. Likewise, a tritiated acetyl derivative can be made by reacting the terminal amino group of the tetrapeptide with tritiated acetic anhydride.

EXAMPLE 5

This example describes the synthesis of ceramide derivatives made from sphingosine. The following chemicals were purchased from Sigma and/or Aldrich and used as received: N-hydroxy succinimide, triphenylmethyl chloride, N,N-dimethyl-4-aminopyridine, benzoyl chloride, anhydrous dimethylformamide, anhydrous acetonitrile, imidazole, t-butylchlorodiphenylsilane, ethylenediaminetetraacetic acid, lithium aluminum hydride, calcium hydride and 1.0 M n-butylammonium fluoride in THF, acetic anhydride, ceramides type III: from bovine brain, galactocerebrosides: type I from bovine brain, galactocerebrosides: type II from bovine brain, N-stearoyl cerebroside, N-palmitoyl cerebroside, N-oleoyl cerebroside, N-nervonoyl cerebroside, psychosine, N-hexanoyl-D-sphingosine, N-palmitoyl-D-sphingosine, N-stearoyl-D-sphingosine, and N-oleoyl-D-sphingosine, N-acetyl-L-glycine, N-t-butylcarbamate-L-proline, nervonic acid.

Dicyclohexylcarbodiimide was purchased from Fluka Chemical and used as received.

The following chemicals were purchased from JT Baker and used as received: p-toluenesulfonic acid monohydrate, phosphorous pentoxide, triethylamine, and potassium hydroxide.

$^1$H NMR spectra were obtained in CDCl$_3$ using a Bruker 200 (200 MHz), 300 (300 MHz), or 499 (499 MHz) NMR spectrometer with tetramethylsilane as an internal standard. Tetrahydrofuran was distilled over lithium aluminum hydride prior to use. Ethyl acetate was distilled over calcium hydride. Methylene chloride was distilled over phosphorous pentoxide. Pyridine was distilled over potassium hydroxide. Silica gel (EM Science Silica Gel 60, 230–400 Mesh) was used for all flash chromatography. Phase contrast optical micrographs were taken using a Zeiss ICM 405 (Carl Zeiss, Inc., Thornwood, N.Y.) with 40× (NA 0.75) or 63× (NA 1.4, oil) phase contrast lenses. Sonication was performed using a bath sonicator (Laboratory Supplies & Co., Inc., Hicksville, N.Y., output 80 KC).

Sphingosine

Mixed N-acyl ceramide (0.250 g) was refluxed for 24 hours in 45 ml concentrated KOH/MeOH and 5 ml H$_2$O. The reaction mixture was cooled to room temp and extracted with 6×25 ml Et$_2$O. Flash chromatography (1:0:0–90:10:1 CHCl$_3$:MeOH:NH$_4$OH) yielded sphingosine as a white solid. The purified residue was dissolved in 50 ml Et$_2$O and washed with 15 ml 20 mM pH 9.5 EDTA(aq) and with 3×15 ml H$_2$O and then dried under vacuum (0.068 g, 54%): R$_f$(MeOH) 0.15; $^1$H NMR (300 MHz) 5.77 (m, 1H, C-5), 5.48 (dd, 1H, C-4, J=7.2, 15.4), 4.05 (t, 1H, C-3, J=6.1), 3.65 (octet, 2H, C-1), 2.88 (m, 1H, C-2), 2.06 (q, 2H, C-6), 0.88 (t, 3H, C-18).

N-hydroxy succinimide ester of nervonic acid

Nervonic acid (0.558 g, 1.52 mmol) and N-hydroxy succinimide (0.175 g, 1.52 mmol) in 60 ml anhydrous ethyl acetate was stirred overnight with dicyclohexylcarbodiimide (0.314 g, 1.52 mmol). The white precipitate was removed and the supernatant evaporated in vacuo. The residue was recrystallized from EtOH to provide N-hydroxy succinimide ester of nervonic acid as fine white needles (0.539 g, 76%): mp 58–60° C.; Rf (CHCl$_3$) 0.24; $^1$H NMR (499 MHz) 5.35 (t, 2H, C-15, C-16, J=5.0 Hz), 2.81 (d, 4H, succinimide, J=4.5 Hz), 2.60 (t, 2H, C-2, J=7.6 Hz), 2.01 (m, 4H, C-14, C-17), 1.74 (t, 3H, C-3, J=5.55 Hz), 0.88 (t, 3H, C-24, J=7.0 Hz).

N-nervonoyl ceramide

N-hydroxy succinimide ester of nervonic acid (0.092 g, 198.4 μmol) and sphingosine (0.062 g, 2D7.0 μmol) were dissolved in 10 ml anhydrous THF and ;stirred overnight under argon. Flash chromatography (1:0:0–90:10:1 CHCl$_3$:MeOH:NH$_4$OH) provided N-nervonoyl ceramide as a white solid (0.118 g, 91%): R$_f$(9:1 CHCl$_3$:MeOh) 0.47; $^1$H NMR (300 MHz) 6.20 (1H, NH), 5.73 (m, 1H, C-5), 5.49 (dd, 1H, C-4, J=6.3, 15.4 Hz), 5.33 (t, 2H, C-15', C-16', J=4.6 Hz), 4.30 (t, 1H, C-3), 3.91 (m, 2H, C-2, C-1), 3.69 (dd, 1H, C-1, J=3.1, 11.0 Hz), 2.21 (t, 2H, C-2', J=7.4 Hz), 2.00 (m, 6H, C-6, C-14', C-17'), 1.60 (t, 2H, C-3', J=7.8 Hz), 0.88 (t, 6H, C-18, C-24', J=6.3 Hz).

N-nervonoyl-1-O-triphenylmethyl ceramide

N-nervonoyl ceramide (0.018 g, 27.8 μmol), triphenylmethyl chloride (0.015 g, 55.5 μmol) and N,N-dimethyl-4-aminopyridine (0.007 g, 55.5 μmol) in 20 ml anhydrous toluene were refluxed for 16 hours under argon. The solvent was removed by rotary evaporation and the residue purified by flash chromatography (9:1–1:1 Hexane:EtOAc) to provide N-nervonoyl-1-O-triphenylmethyl ceramide as a white solid (0.018 g, 72%): R$_f$(3:1 Hexane:EtOAc) 0.21; $^1$H NMR (300 MHz) 7.42–7.22 (15H), 6.06 (d, 1H, NH, J=7.9 Hz), 5.63 (m, 1H, C-5), 5.35 (t, 2H, C-15', C-16', J=5.2 Hz), 5.25 (dd, 1H, C-4, J=6.2, 15.5 Hz), 4.18 (m, 1H, C-2), 3.69 (dd, 1H, C-3, J=3.9, 7.8 Hz), 3.32 (m, 2H, C-1), 2.20 (t, 2H, C-2', J=8.1 Hz), 2.00 (m, 4H, C-14', C-17'), 1.91 (m, 2H, C-6), 1.6(m, \4 2H, C-3'), 0.88 (t, 6H, C-18, C-24', J=6.5 Hz).

N-nervonoyl-1-o-triphenylmethyl-3-O-[diphenyl-t-[butylsilyl] ceramide

N-nervonoyl-1-O-triphenylmethyl ceramide (0.108 g, 0.12 mmol), imidazole (0.066 g, 0.97 mmol). and t-butylchlorodiphenylsilane (0.79 ml, 3.03 mmol) were stirred 19.5 hours in 25 ml anhydrous DMF under argon. 25 ml of H$_2$O were added and extracted with 3×15 ml Et$_2$O. The ether layer was washed with 10 ml H$_2$O and 10 ml saturated NaCl (aq). Flash chromatography (15:1–2:1 Hexane:EtOAc and 1 ml triethylamine/100 ml of solvent) provided N-nervonoyl-1-O-triphenylmethyl-3-O-[diphenyl-t-butylsilyl] ceramide as a white solid (0.090 g, 66%): R$_f$(3:1 Hexane:EtOAc 0.66; $^1$H NMR (300 MHz) 7.70–7.23 (m, 25H), 5.36–5.25 (m, 5H, NH, C-4, C-5, C-15', C-16'), 4.39 (t, 1H, C-3, J=5.4 Hz), 4.18 (m, 1H, C-2), 3.94 (dd, 1H, C-1, J=5.1, 10.4 Hz), 3.70 (dd, 1H, C-1, J=5.1, 10.4 Hz), 2.00 (m, 4H, C-14', C-17'), 1.86 (m, 2H, C-2'), 1.72 (m, 2H, C-6), 1.44 (m, 2H, C-3'), 1.04 (s, 9H, t-Bu), 0.88 (t, 6H, C-18, C-24', J=7.3 Hz).

N-nervonoyl-3-O-[diphenyl-t-butylsilyl] ceramide

N-nervonoyl-1-O-triphenylmethyl-3-O-[(diphenyl-t-butylsilyl] ceramide (0.093 g, 82.4 μmol) was stirred for 4 hours with p-toluenesulfonic acid monohydrate (0.010 g, 49.4 μmol) in 20 ml 1:1 MeOH:CH$_2$Cl$_2$. Et$_2$O was added (40 ml) and the solution was washed with 10 ml 5% NaHCO$_3$ (aq) and 10 ml H$_2$O. Flash chromatography (6:1–0:1 Hexane:EtOAc) provided N-nervonoyl-3-O-[diphenyl-t-butylsilyl] ceramide as a white solid (0.0:34 g, 47%): Rf(3:1 Hexane:EtOAc) 0.15; $^1$H NMR (499 MHz) 7.67–7.30 (m, 10H), 5.93 (d, 1H, NH, J=7.1 Hz), 5.42–5.3:3 (m, 4H, C-4, C-5, C-15', C-16'), 4.34 (t, 1H, C-3, J=4.5 Hz), 3.97–3.82 (m, 2H, C-1, C-2), 3.60 (m, 1H, C-1), 3.14 (m, 1H, OH), 1.98 (m, 6H, C-2', C-14', C-17'), 1.8f, (m, 2H, C-6), 1.55 (m, 2H, C-3'), 1.07 (s, 9H, t-Bu), 0.88 (t, 6H, C-18, C-24', J=7.0 Hz).

N-nervonoyl-1-O-(N-acetyl-glycine)-3-O-[diphenyl-t-butylsilyl] Ceramide

N-nervonoyl-3-O-[diphenyl-t-butylsilyh] ceramide (0.021 g, 23.7 μmol), N-acetyl-glycine (0.006 g, 47.4 μmol), and N,N-dimethyl-4-aminopyridine (0.06 g, 47.4 μmol) in 21 ml 2:5 CH$_3$CN:CH$_2$Cl$_2$ (anhydrous) were stirred for 2 hours under argon. Thereafter, dicyclohexylcarbodiimide (0.010 g, 47.4 μmol) was added and the reaction stirred for 24 hours under argon. The solvent was removed in vacuo. Flash chromatography (5:1–0:1 Hexane:EtOAc) of the residue provided N-nervonoyl-1O-(N-acetyl-glycine)-3-O-[diphenyl-t-butylsilyl] ceramide as a white solid (0.016 g, 70%): R$_f$(1:1 Hexane:EtOAc) 0.23; $^1$H NMR (300 MHz) 7.67–7.57 (dd, 4H), 7.46–7.33 (m, 6H), 6.09 (bs, 1H, NH), 5.51–5.29 (m, 4H, C-4, C-5, C-15', C-16'), 4.40 (dd, 1H, C-3, J=2.9, 10.8 Hz), 4.26 (bs, 2H, C-1), 4.12 (m, 1H, C-2), 3.93 (t, 2H, glycine, J=11.3 Hz), 2.00 (s, 3H, NAc), 1.05 (s, 9H, t-Bu), 0.88 (t, 6H, C-18, C-24', J=6.4 Hz)

N-nervonoyl-1-O-(N-acetyl-L-proline)-3-O-[diphenyl-t-butylsilyl] Ceramide

N-nervonoyl-3-O-[diphenyl-t-butylsilyl] ceramide (0.034 g, 38.4 μmol), N-acetyl-L-proline (0.010 g, 63.6 μmol), and N,N-dimethyl-4-aminopyridine (0.011 g, 90.0 μmol) in 15 ml 1:2 CH$_3$CN:CH$_2$Cl$_2$ (anhydrous) were stirred for 30 min under argon. Dicyclohexylcarbodiimide (0.012 g, 57.5 μmol) was added and the reaction stirred for 24 hours under argon. The white precipitate was removed by vacuum filtration and the solvent evaporated in vacuo. Flash chromatography (6:1–0:1 Hexane:EtOAc) of the residue provided N-nervonoyl-1-O-(N-acetyl-L-proline)-3-O-[diphenyl-t-butylsilyl] ceramide as a white solid (0.029 g, 74%): R$_f$(1:1 Hexane:EtOAc) 0.29; $^1$H NMR (300 MHz) 7.68–7.59 (dd, 4H), 7.43–7.26 (m, 6H): 6.14 (d, 1H, NH, J=8.8 Hz), 5.41–5.29 (m, 3H, C-4, C-15', C-16'), 5.14 (dt, 1H, C-5, J=4.0, 8.8 Hz), 4.69 (d, 1H, a, J=7.7 Hz), 4.39 (dd, 1H, C-3, J=3.6, 8.1 Hz), 4.27 (d, 2H, C-1, J=12.4 Hz), 4.02 (t, 1H, C-2, J=7.3 Hz), 3.44 (t, 2H, d, J=6.4 Hz), 2.16 (m, 2H, b), 2.02–1.91 (m, 13H, C-6, C-2', C-14', C-17', c, NAc), 1.49 (m, 2H, C-3'), 1.03 (s, 9H, t-Bu), 0.88 (t, 6H, C-18, C-24', J—6.6 Hz).

N-nervonoyl-1-O-(N-t-butylcarbamate-L-proline)-3-O-[diphenyl-t-butylsilyl] Ceramide N-nervonoyl-3-O-[diphenyl-t-butylsilyl] ceramide (0.041 g, 46.2 μmol), N-t-butylcarbamate-L-proline (0.011 g, 50.9 μmol) and N,N-dimethyl-4-aminopyridine (0.006 g, 50.9 μmol) were stirred for 4 hours under argon in 7 ml anhydrous Ch$_3$CN and 17 mL anhydrous CH$_2$Cl$_2$. Dicyclohexylcarbodiimide (0.010 g, 50.9 μmol) was added and the reaction stirred for 24 hours under argon. The white precipitate was removed by vacuum filtration and the solvent evaporated in vacuo. Flash chromatography (7:1–0:1 Hexane:EtOAc) of the residue provided N-nervonoyl-1-O-(N-t-butylcarbamate-L-proline)-3-O-[diphenyl-t-butylsilyl] ceramide as a white solid (0.014 g, 28%): Rf(3:1 Hexane:EtOAc) 0.44; $^1$H NMR (300 MHz) 7.67–7.60 (m, 4H), 7.44–7.26 (m, 6H), 6.02 (d, 1H, NH, J=9.3 Hz), 5.40–5.24 (m, 3H, C-4, C-15', C-16'), 5.06 (dt, 1H, C-5, J=4.0, 8.8 Hz), 4.62 (dd, 1H, a, J=3.7, 6.7 Hz), 4.41–4.10 (m, 4H, C-1, C-2, C-3), 3.46 (m, 2H, d), 1.41 (s, 9H, Ot-Bu), 1.03 (s, 9H, Sit-Bu), 0.88 (t, 6H, C-18, C-24', J=6.2 Hz).

1-O-(N-acetyl-glycine)-nervonoyl ceramide

N-nervonoyl-1-O-(N-acetyl-glycine)-3-O-[diphenyl-t-butyl-silyl] ceramide (0.009 g, 9.1 $\mu$mol) in 10 mL anhydrous THF and 0.01 ml 1.0 M n-butylammonium fluoride (in THF) were stirred for 1 hour under argon. The solvent was removed by rotary evaporation and the residue purified by flash chromatography (2:1–0:1 Hexane:EtOAc) to provide 1-O-(N-acetyl-glycine)-nervonoyl-ceramide as a white solid (0.002 g, 29%): $R_f$(EtOAc) 0.25; $^1$H NMR (499 MHz) 6.11 (bs, 1H, NH), 6.01 (bs, 1H, NH), 5.76 (dt, 1H, C-5, J=6.7, 15.5), 5.48 (dd, 1H, C-4, J=6.2, 15.5 Hz), 5.33 (t, 2H, C-15', C-16', J=5.0 Hz), 4.33 (d, 2H, gly), 4.15 (m, 2H, C-2, C-3), 4.00 (m, 2H, C-1), 2.17 (t, 2H, C-2', J=4.4 Hz), 2.03 (s, 3H, NAc), 0.86 (t, 6H, C-18, C-24', J=6.6 Hz).

1-O-(N-acetyl-L-proline)-nervonoyl Ceramide

N-nervonoyl-1-O-(N-acetyl-L-proline)-3-O-[diphenyl-t-butyl-silyl] ceramide (0.021 g, 20.5 $\mu$mol) in 12 ml anhyd THF and 0.01 ml 1.0 M n-butylammonium fluoride (in THF) was stirred for 2 hours under argon. The solvent was removed by rotary evaporation and the residue purified by flash chromatography (3:1–0:1 Hexane:EtOAc) to provide 1-O-(N-acetyl-L-proline)-ceramide as a white solid (0.011 g, 69%): $R_f$(EtOAc) 0.31; $^1$H NMR (499 MHz) 6.66 (d, 1H, NH, J=7.7 Hz), 5.70 (dt, 1H, C-5, J=6.7, 15.5), 5.47 (dd, 1H, C-4, J=6.2, 15.5 Hz), 5.32 (t, 2H, C-15', C-16', J=4.6 Hz), 4.47–4.26 (m, 4H, a, C-2, C-3), 4.06 (bs, 2H, C-1), 3.64–3.50 (dm, 2H, d), 3.30 (bs, 1H OH), 2.18 (m, 2H, b), 2.07 (s, 3H, NAc), 1.99 (m, 10H, C-6, C-2', C-14', C-17', c), 1.59 (m, 2H, C-3'), 0.86 (t, 6H, C-18, C-24', J=7.0 Hz).

EXAMPLE 6

This example describes a general HAR microstructure forming regimen. Amphiphile (0.1 mg) was dissolved in anhydrous DMF so that the concentration was 1.0 mM. Water was added in ≈10 $\mu$L increments until the solution became cloudy. The test tube was then covered and allowed to sit at 20° C. for 2–24 hours undisturbed. For larger amounts of amphiphile, water was added with vortex mixing (≈3 sec) between additions.

EXAMPLE 7

This example describes a general HAR microstructure forming regimen. Amphiphile (0.1 mg) was dissolved in pyridine so that the concentration was 1.0 mM. Water was added in ≈10 $\mu$l increments until the solution became cloudy. The test tube was allowed to sit at 20° C. so that the solvent could evaporate over time.

EXAMPLE 8

This example describes a general HAR microstructure forming regimen. Amphiphile (0.1 mg) was placed in 1 ml buffered water (10 mM $KH_2PO_4$, 100 mM NaCl, 1.5 mM $NaN_3$, pH=6.6). The solution was thrice incubated for 3 min at 90° C., vortexed for 20 sec and then sonicated for 20 sec. Next, the solution was frozen for 2 min in i-PrOH/$CO_2$(s), thawed rapidly (≈20 sec) and then vortexed 20 sec. The freeze-thaw procedure was repeated three times except that after the last freeze the material was allowed to slowly warm to room temperature over ≈1.5 hours.

EXAMPLE 9

This example describes a general HAR microstructure forming regimen. Amphiphile was placed in ethylene glycol:water (either 19:1 or 1:1 v/v) for EL final concentration of 1 mg/ml. The solution was thrice incubated for 10 min at 990 C and sonicated at 50° C. (12×30 sec pulses with 30 sec pauses). After the final sonication the solution was allowed to cool from 99° C. to room temperature over ≈2.5 hours.

EXAMPLE 10

This example describes a particular HAR microstructure forming regimen. Samples of 0.2 mg of $NH_2$-Gly-Lys-Sar-Pro-Glu(NH—$C_{12}H_{25}$)$_2$ or (Pro)$_3$—Glu(NH—$C_{12}H_{25}$)$_2$ were dissolved in 40 $\mu$l of MeOH were added to 400 $\mu$l of HEPES buffered saline at pH 7.4 while vortexing and incubated for 2 hours at room temperature. In the case of Ac-Gly-Arg-Ala-Gly-Gly-(Ala)$_2$-(Pro)$_3$-Glu(NH-$C_{14}H_{29}$)$_2$ (peptide 2), 150 $\mu$l of a 1 mg/ml MeOH solution of the peptide lipid was mixed with 350 $\mu$l of HEPES buffered saline (HBS), and incubated overnight. Before microscopy the obtained peptide-2 particles; were transferred to HBS using centrifugal-driven filtration. To do this, particles were centrifuged on filters with 30,000 Da nominal molecular weight limit (Millipore) for 15 min at 3000× g at room temperature. After substitution of the filtrate with 1 ml of fresh HBS, centrifugation was repeated. The particles, retained on the filter were resuspended in another 200 $\mu$l portion of HBS. Optical microscopy of the particles obtained shows that upon dilution of MeOH solution, $NH_2$-Gly-Lys-Sar-Pro-Glu(NH—$C_{12}H_{25}$)$_2$, (Pro)$_3$-Glu(NH-$C_{12}H_{25}$)$_2$, and peptide-2 efficiently form particles with high axial ratios and uniform diameters.

EXAMPLE 11

This example describes how to make HAIM's from Ac-NH-Lys-Ala-Sar-Pro-Glu(NH—$C_{12}H_{25}$)$_2$ and $NH_2$Gly-Lys-Sar-Pro-Glu(NH—$C_{12}H_{25}$)$_2$ by heating and cooling in HBS/EtOH mixtures. 0.2 mg of Ac-NH-Lys-Ala-Sar-Pro—Glu(NH—$C_{12}H_{25}$)$_2$ and $NH_2$Gly-Lys-Sar-Pro-Glu(NH—$C_{12}H_{25}$)$_2$ were dissolved in 50 $\mu$l of EtOH. The minimum fraction of HBS that induces precipitation of the peptide lipids was found by addition of HBS in 10 ml portions while vortexing, with 5 min incubations after each addition. These compounds formed cylinders. For Ac-NH-Lys-Ala-Sar-Pro-Glu(NH—$C_{12}H_{25}$)$_2$ the concentration of EtOH in the mixture allowing for precipitation was about 46 percent, by volume, and about 42 percent for $NH_2$Gly-Lys-Sar-Pro-Glu (NH—$C_{12}H_{25}$) 2

EXAMPLE 12

This example describes forming HARMs by heating and cooling in HBS/MeOH mixtures. 0.1 mg samples of (Pro)$_3$-Glu-(NH—$C_{14}H_{29}$)$_2$ or (Pro)$_3$-Glu-(NH—$C_{14}H_{29}$)$_2$ dissolved in 20 $\mu$l of MeOH each were added to 200 $\mu$l of HBS at pH 7.4 while vortexing. Concentrations of MeOH in the samples were adjusted to be between 20 and 50 percent, by volume. Sealed samples were then heated to 65° C., and slowly (within about 4 hours) cooled to room temperature. The obtained particles were separated from MeOH/HBS mixtures by centrifugation at 3000× g for 15 min at room temperature. The obtained pellets were reconstituted in 1 ml of HBS. After overnight incubation the particles were filtered on centrifugal-driven filtration units and reconstituted in 150 μl of HBS each. The slow cooling technique resulted in close to 100% conversion of the peptide lipids to particles having high axial ratios.

EXAMPLE 13

This example describes a stability study to determine the stability of the cylinders at. physiological temperatures. Tubules of $(Pro)_3$-Glu(NH—$C_{12}H_{25})_2$ were formed by dilution of MeOH solutions as described above in Example 12. Tubules of $(Pro)_3$-Glu(NH—$C_{16}H_{33})_2$ were formed by heating and cooling in HBS/MeOH mixtures as described above in Example 12. These tubules were then incubated in HBS for 1 hour at 38° C. The results indicate that the stability of the tubules correlates with the $T_M$, i.e., if the $T_M$ is greater than the temperature of the environment, then the tubules are stable. For example, the $T_M$ of $(Pro)_3$-Glu(NH—$C_{16}H_{33})_2$ is about 59° C., and the incubation of these tubules did not convert the tubules to different microstructures. The $T_M$ of tubules of $(Pro)_3$-Glu(NH—$C_{12}H_{25})_2$ is about 29.9° C., and incubation of such tubules at physiological temperature converted the tubules into semi-clear micellar solutions.

EXAMPLE 14

This example describes a stability study of tubules at physiological pH. $(Pro)_3$-Glu (NH—$C_{16}H_{33})_2$ tubules formed by heating and cooling in HBS/MeOH mixtures as described above. Such tubules were then incubated for 45 hours at 40° C. in the presence of fetal calf serum (FCS) or sonicated dioleyoyl-phosphatidylcholine (DOPC) liposomes in HBS at pH 7.4. Incubation in HBS, which was used as a control, nor the biological fluids tested, did not destroy the tubules. This demonstrates that the presence of lipid membranes and components of blood plasma at physiological temperature are not, by themselves, sufficient to destroy the tubule microstructure. This means that injection of such materials into mammals the morphology of the tubules will not be changed dramatically, and that the tubules will provide natural release in a manner that is characteristic for their shape.

EXAMPLE 15

This example describes the cleavage of a peptide coupled to ditetradecyl glutamide, namely α, γ-ditetradecyl Nα-acetyl-glycyl-arginyl-alanyl-glycyl-gylcyl-alanyl-alanyl-prolyl-prolyl-prolyl-qlutamide trifluoroacetate (substrate). A mixture comprising 5.46 nmoles of the substrate in 0.25 Molar Na-borate buffer and 1 μl (0.4 μg) trypsin in trypsin buffer was formed. The mixture was then incubated at 37° C. The course of the reaction was followed by TLC (4:1:1 butanol/acetic acid/water; visualized with O-toluidine). TLC analysis indicated about 80–90% cleavage of the peptide by tripsin.

EXAMPLE 16

This example concerns the enzymatic cleavage of constituent molecules self-assembled into cylinders. A relatively homogeneous population of tubules of $DC_{8,9}PC$ was formed using the techniques stated in *Helical and Tubular Microstructures Formed by Polymerizable Phosphatidylcholines,* 109:6169–6175, J. Am. Chem. Soc. (1987), which is incorporated herein by reference. Tubules were precipitated by drop-wise addition of water to a 5 mM solution of the lipid in ethanol until the volume fraction of water reached 70%. The tubules were washed 7 times in distilled/deionized water by repeated centrifugation to remove traces of ethanol. The final pellet of tubules was resuspended in 150 μM NaCl, 50 mM Tris-HCl (pH 8.0) in the presence of 10 mM $CaCl_2$. The tubules were then incubated at 30° C. in Tris-HCl buffer at pH 8.0 at a lipid concentration of 0.5 mM in the presence of 10 mM $Ca^{++}$. At $t_0$, 4 units (2.24 μg/ml) of Naja naja venom $PLA_2$ (Sigma Chemicals) were added to the tubules. At periodic intervals thereafter 100 Al aliquots were removed and quenched with 25 mM EDTA, which scavenges $Ca^{++}$ and stops the $PLA_2$ reaction. The samples were briefly heated to above $T_m$ in a 10-fold excess of TX100 to disperse all tubules, and added to a fluorescence cuvette containing 2.0 ml of 0.2 μM of ADIFAB in calcium-free Tris-HCl buffer. Concentrations of "free" fatty acid were determined from the ratio of intensities and a calibration curve.

Figure 14:
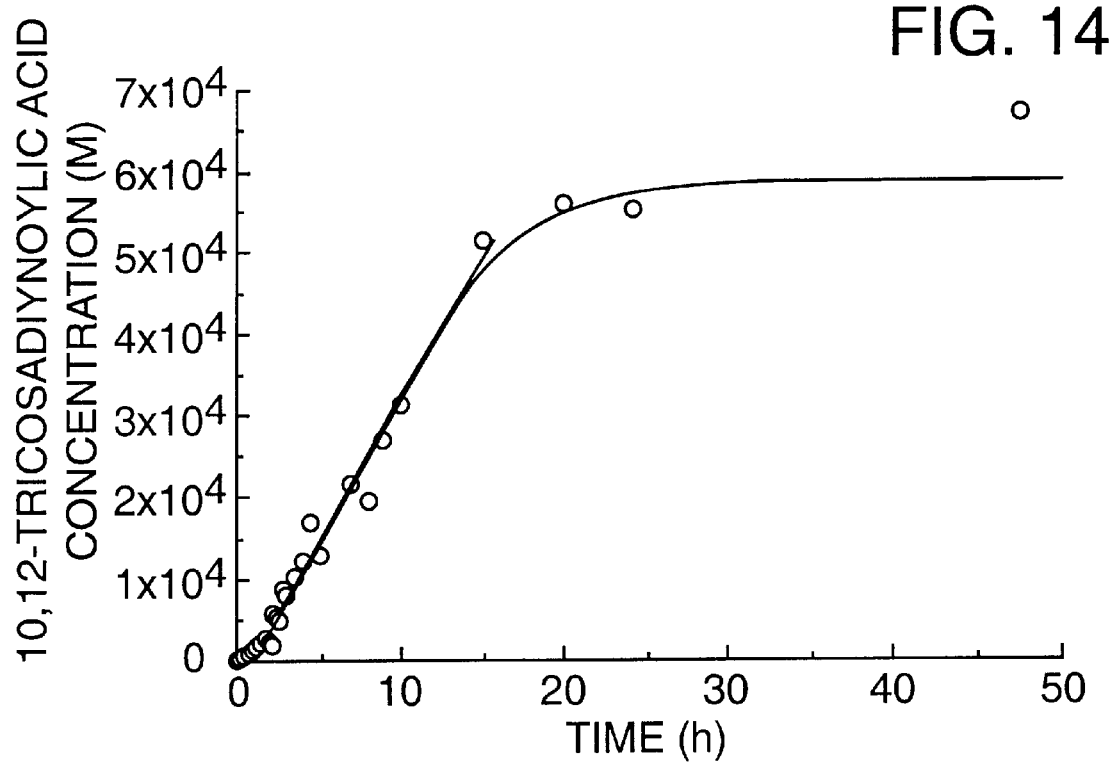
FIG. 14 is a graph showing the total concentration of 10,12-tricosadiynolic acid ($DC_{8,9}PC$) over time following the action of $PLA_2$ on a suspension of $DC_{8,9PC}$.

The results of cleavage by $PLA_2$ are illustrated in FIG. 14. FIG. 14 shows that the hydrolysis rate is substantially constant over the time period tested. The constant rate of hydrolysis continues until nearly all of the substrate is consumed.

EXAMPLE 17

This example concerns the synthesis of HARMs from glutamic acid dihexadecyl amide [Glu(NHC$_{16}H_{33})_2$; GADH]. All chemicals and solvents from commercial sources were reagent grade. L-glutamic acid (Sigma Chemical, St. Louis, Mo.) was used. GADH (Table I, comp. #3, example 1) as described above). Kyujin, et. al., also describes preparation of $(Pro)_3$-Glu(NHC$_{16}H_{33})_2$ see p. 81, *Formation of High Axial Ratio Microstructures from Peptides Modified with Glutamic Acid Dialklyl Amides,* Biochimica et Biophysica Acta 1371:168–184 (1998), incorporated herein by reference. The structure of the product synthesized was confirmed by $^1$HNMR (Brucker, 300 Mhz)

To form HARMS, one of the nine buffers, listed in Table 3 or Table 4 was added to 1 mg/ml GADH solution in absolute EtOH while vortexing to final EtOH concentration of 80%.

TABLE 3

| Buffer | pH 4.0 (20 mM Na-Citrate) | pH 7.4 (20 mM HEPES) | pH 9.5 (20 mM Na-Borate) |
|---|---|---|---|
| No NaCl | Crystals | HARMs | HARMs |
| 120 mM NaCl | Crystals | HARMs | HARMs |
| 1 M NaCl | Amorphous aggregate | Crystals | HARMs, some crystals |

TABLE 4

| Buffer | pH 4.0 (20 mM Na-Citrate) | pH 7.4 (20 mM HEPES) | pH 9.5 (20 mM Na-Borate) |
|---|---|---|---|
| No NaCl | Crystals | Very short, aggregated HARMS | HARMs |
| 120 mM NaCl | Crystals | Crystals, with some indication of tubular structures | HARMs |
| 1 M NaCl | Amorphous aggregate | Crystals | Crystals, short HARMs |

The resulting mixtures were incubated overnight at room temperature. The suspensions obtained were incubated at 55° C. for 15 min, then cooled to room temperature either at 0.2° C./min using an RTE-110P programmable water bath (Neslab Instruments, Newington, N.H.; results; in Table 3), or by allowing to sit at ambient temperature (approximately 4° C./min, "rapid" cooling; results in Table 4).

The HARMs formed were transferred to aqueous buffers using centrifugal-driven filtration. 0.5-ml aliquots of the suspensions were centrifuged in Ultrafree®-CL Centrifugal Filters with a 30,000 Da nominal molecular weight limit (Millipore Co., Bedford, Mass.) for 15 min at 3000× g at room temperature, washed twice with 1 ml of the appropriate buffer under the same conditions, and resuspended in 0.5 ml of the same buffer.

The morphology of the particles obtained was studied using a phase contrast microscope ° Carl Zeiss, Thornwood, N.Y.) equipped with a ccd video camera (SBIG, Inc., Santa Barbara, Calif.). The images obtained were processed using image processing software, NIH Image 1.61.

EXAMPLE 18

This example concerns the synthesis of glutamic acid dihexadecyl amide [Glu(NHC$_{16}$H$_{33}$)$_2$; GADH]-calf-thymus DNA HARM complexes. GADH was synthesized and converted to (Pro)$_3$-Glu(NHC$_{16}$H$_{33}$)$_2$ as described above.

An 0.72 mg/ml (0.8 mM) (Pro)$_2$-Glu (NHC$_{16}$H$_{33}$)$_2$ micellar solution in 40 mM octylglucoside (OG) in HEBS at pH 7.4 was formed. 1 ml aliquouts of this solution were added to 1 ml aliquots of 400 µg/ml, 200 µg/ml, 100 µg/ml, or 50 µg/ml solutions of calf thymus DNA (Sigma Chemical, St. Louis, Mo.) in 40 mM OG in HBS. These mixtures were then incubated overnight at room temperature. Optical microscopy revealed HARMs with approximately the same morphology after overnight co-incubation of DNA and (Pro)3-Glu(NHC$_{16}$H$_{33}$)2 in the presence of 40 mM OG regardless of the lipopeptide/DNA ratio. No particles were detected in the samples that lacked either lipopeptide or DNA. Observed differences in the appearance of samples with and without DNA suggests that DNA interacts with the (Pro)$_3$-Glu (NHC$_{16}$H$_{33}$)$_2$, which results in the precipitation of a DNA/(Pro)$_3$-Glu (NHC$_{16}$H$_{33}$)$_2$ complex.

The samples containing 0.4 mM (Pro)$_3$-Glu (NHC$_{16}$H$_{33}$)$_2$ and either 200 µg/ml or 25 µg/ml DNA, 0.4 µM (Pro)$_3$-Glu (NHC$_{16}$H$_{33}$)$_2$ containing no DNA, and 200 µg/ml DNA containing no lipopeptide were dialyzed against HBS to remove OG. OG removal does not change the morphology of DNA/(Pro)$_3$-Glu (NHC$_{16}$H$_{33}$)$_2$ complexes, but does induce formation of amorphous aggregates in the sample containing (Pro)$_3$-Glu (NHC$_1$6H$_{33}$)$_2$ without DNA. The difference in appearances of these two samples confirms formation of DNA/(Pro)$_3$-Glu (NHC$_1$6H$_{33}$)$_2$ complexes. No particles were found in the sample containing DNA but not the lipopeptide after OG removal.

To estimate efficiency of DNA incorporation, 0.5 ml aliquots of the dialyzed samples that originally contained 0.4 mM (Pro)$_3$-Glu (NHC$_{16}$H$_{33}$)$_2$ and 200 µg/ml DNA were sedimented by centrifugation for 30 minutes at 3000× g at room temperature, resuspended in 0.5 ml of HBS and sedimented again. Aliquots of the same volumes containing 200 µg/ml DNA with no lipopeptide, or 0.4 mM of (Pro)$_3$-Glu (NHC$_{16}$H$_{33}$)$_2$ containing no DNA, were used as controls. The volumes of the pellets and the supernatants obtained were adjusted to 0.5 ml. Aliquots of 1.5 ml of 2% Na-dodecyl sulfate (SDS) ir HBS were added to each fraction. Concentrations of DNA were estimated by optical density at 260 nm (A$_{260}$).

FIG. 15 shows the distribution of A$_{260}$ between fractions. With reference to FIG. 15, the samples were as follows: sample "A" was 200 µg/ml DNA, no lipopeptide; sample "B" was 200 µg/ml DNA, 0.4 mM (Pro$_3$)-Glu(C$_{16}$H$_{33}$)$_2$; and sample "C" was 0.4 mM (Pro$_3$)-Glu(C$_{16}$H$_{33}$)$_2$. Most of the DNA from the sample containing both DNA and the lipopeptide sediments upon centrifugation. Apparent sedimentation of the control DNA was very low and determined to be non-specific adsorption on the test tube walls. A$_{260}$ values of all fractions obtained from the (Pro)$_3$-Glu (NHC$_{16}$H$_{33}$)$_2$ or lipopeptide (1) sample containing no DNA were negligible, demonstrating that the presence of (Pro)$_3$-Glu (NHC$_{16}$H$_{33}$)$_2$ or lipopeptide (1) does not interfere with estimation of DNA concentrations. The data obtained once again confirm formation of DNA/Pro-GADH complexes. The efficiency of DNA incorporation (defined as the percentage of incorporated DNA vs. total DNA) was about 83%.

EXAMPLE 19

This example describes the treatment of HARM complexes comprising (1) and DNA with DNase to demonstrate that (1) DNAase does not interfere with HARM formation, and (2) incorporating DNA into HARMs reduces enzymatic degration of the DNA. Aliquots of 10 µl of 250 mM MgCl$_2$ in HBS and 2.5 Al of 5000 Kunitz units/ml DNase I in HBS were successively added to 0.5 ml DNA/lipopeptide (200 µg/ml, 0.4 mM) or DNA (200 µg/ml) samples obtained after dialysis as described above. The mixtures were incubated with stirring at room temperature for 30 minutes. The concentrations of intact DNA were estimated by A$_{260}$ in the washed samples obtained after centrifugation; SDS micellorisation proceeded as in similar samples not treated with DNase I.

To check DNase I activity, 40 µl of 250 mM MgCl$_2$ and 10 µl of 5000 Kunitz units/ml DNase I in HBS were succesively added to 2 ml of 40 µg/ml DNA in HBS. The mixture obtained was incubated at room temperature with stirring. DNA degradation was monitored by A$_{260}$ increase.

Figure 16:
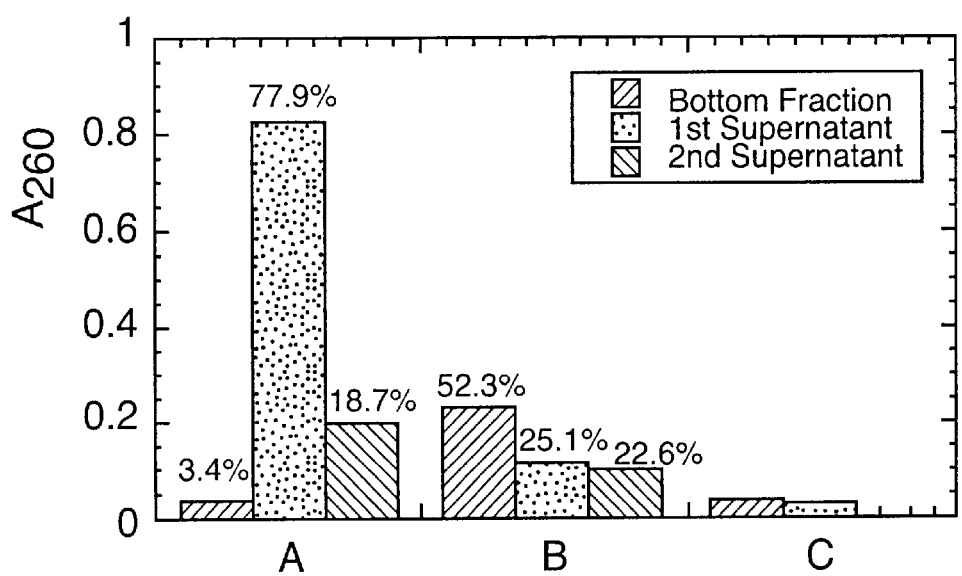
FIG. 16 is a graph of DNA absorbance at 260 nm for the bottom fraction, and first and second supernatant samples produced by centrifuging A) 200 μg/ml DNA, no lipopeptide, B) 200 μg/ml DNA, 0.4 mM $(Pro)_3$-Glu $(NHC_{16}H_{33})_2$, and C) 0.4 mM $(Pro)_3$-GLu$(NHC_{16}H_{33})_2$ after co-incubation of these samples with DNase.
Figure 17:
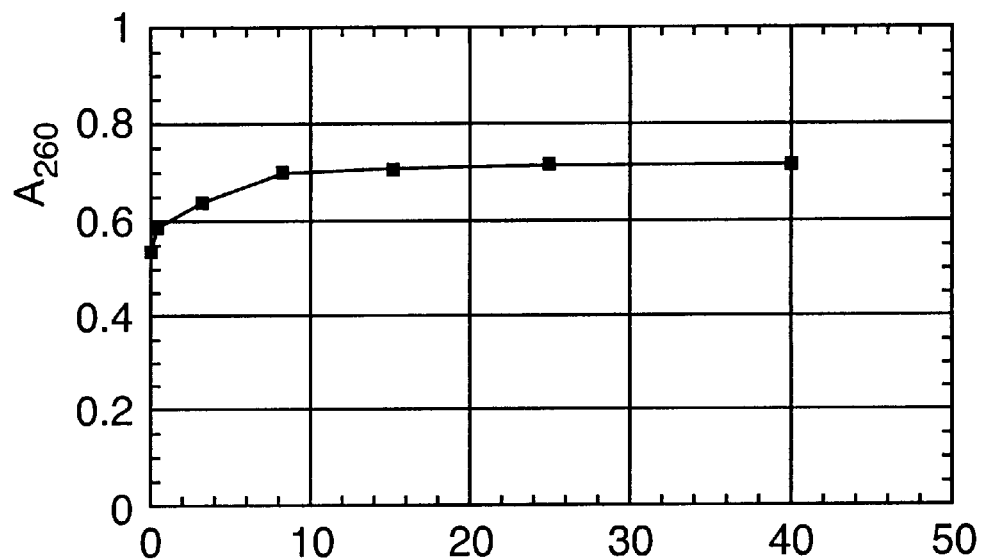
FIG. 17 is a graph of absorbance at 260 nm versus time for the degradation of 40 μg/ml DNA in the presence of 50 Kunitz units of DNase in 5 mM $MgCl_2$/HBS at a pH of 7.4.

Incubation of DNA/lipopeptide complexes with DNase I does not appear to significantly affect the ability of DNA to co-sediment with lipid. See, FIG. 16, where: sample "A" was 200 µg/ml DNA, no lipopeptide; sample "B" was 200 µg/ml DNA, 0.4 mM (Pro$_3$)-Glu(C$_{16}$H$_{33}$)$_2$; and sample "C" was 0.4 mM (Pro$_3$)-Glu(C$_{16}$H$_{33}$)$_2$. FIG. 17 presents data from a control experiment and demonstrates that the DNase used for this example was active. Negligible A$_{260}$ in all fractions obtained from the lipopeptide sample containing no DNA (sample 3, FIG. 16) shows that possible adsorption of the DNase to the HARMS does not contribute to A$_{260}$, and hence does not effect estimating DNA concentration. Individual nucleotides apparently cannot form stable complexes with the lipopeptide. Hence, FIG. 16 shows that incorporating DNA, into lipopeptide complexes protects the DNA against enzymatic degradation.

EXAMPLE 20

This example concerns the synthesis of HARMs from glutamic acid dihexadecyl amide [Glu(NHC$_{16}$H$_{33}$)$_2$; GADH] and loading those HARMs with a green fluorescent protein encoding plasmid, pEGFP-N1 (Clontech Laboratories, Inc., Palo, Alto, Calif.)

pEGFP-N1 was propagated in DH5-alpha *E. coli* strand according to a standard protocol. Plasmid Purification Giga Kit was used to isolate (Qiagen, Santa Clarita, Calif.). The structure of pEGFP-N1 obtained was confirmed by 1% agarose electrophoresis after degradation with endonucleases NotI and BamHI (MBI Ferments, Amherst, N.Y.) according to the manufacture's protocol.

Figure 18:
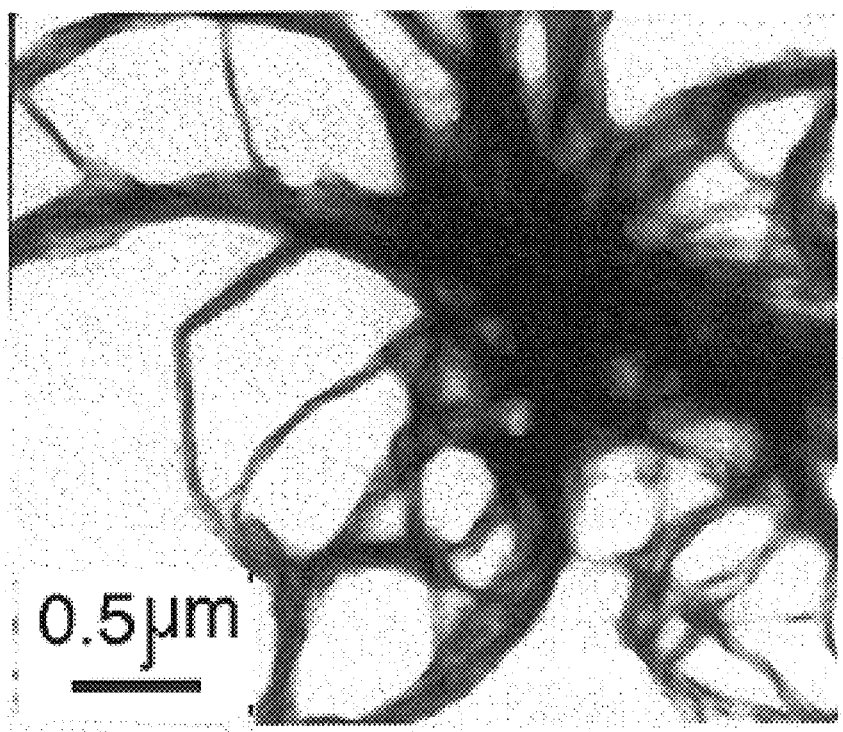
FIG. 18 is a TEM image of HARMs obtained after incubation and dialysis of 0.4 mM $(Pro)_3$-Glu$(NHC_{16}H_{33})_2$, 50 μg/ml pEGFP-N1 and 40 mM OG.

A 0.5 ml aliquot of the mixed micellar solution of the lipopeptide in 40 mM OG was added to 0.5 ml of 50 µg/ml pEGFP-N1 in 40 mM OG. The resulting mixture was incubated at room temperature overnight, then dialyzed against two changes of 300-fold volume of HBS for 36 hours at room temperature. pEGFP-N1/lipopeptide complexes with morphologies very close to those of thymus/lipopeptide were revealed as illustrated by FIG. 18, which is a TEM image of the dialyzed sample.

Alternatively, pEGFP-N1/(Pro)$_3$-Glu(NHC$_{16}$H$_{33}$)2 complexes were formed by co-incubation of the preformed empty HARMs in the presence of pEGFP-N1. Empty (Pro)$_3$-Glu(NHC$_{16}$H$_{33}$)$_2$ HARMs were formed by cooling a solution of the surfactant in 30% MeOH at 0.2° C/minute. The (Pro)$_3$-Glu(NHC$_{16}$H$_{33}$)$_2$ HARMs were transferred to HBS using centrifugal-driven filtration. Such HARMs at a concentration of about $10^{-7}$ M lipopeptide were incubated for 30 minutes at room temperature with HBS solution of pEGFP-N1 at a concentration ranging from $10^{-8}$ to $10^{-7}$ M. HARM-bound and free PEGFP-NI were separated. by centrifugation at 16,000× g for 15 minutes. Concentrations of pEGFP-N1 in the resultant samples were estimated by A$_{260}$ in 1.5% SDS, pH 7.4.

Figure 19:
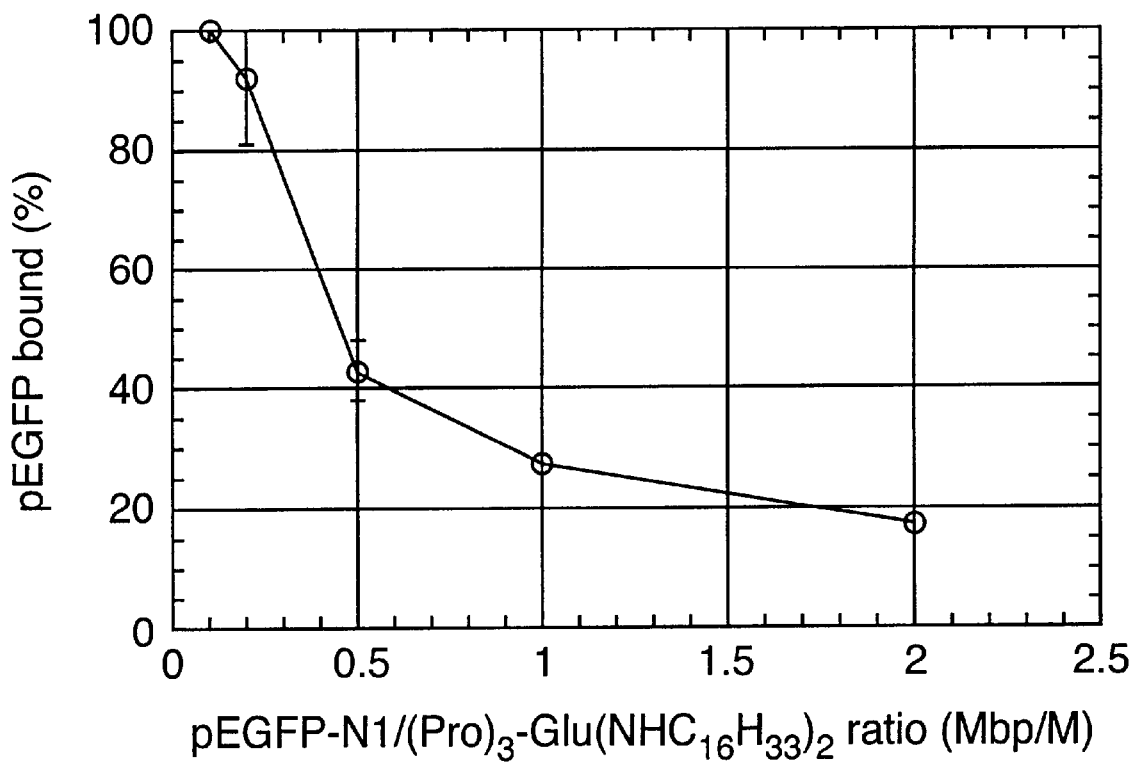
FIG. 19 is a graph of the pEGFP-N1/$(Pro)_3$-Glu $(NHC_{16}H_{33})_2$ (Mbp/M) ratio versus the percent of bound pEGFP.

FIG. 19 shows relative binding of increasing mole fraction of pEGFP-N1 to a constant quantity of (Pro)$_3$-Glu (NHC$_{16}$H$_{33}$)$_2$ HARMs. The X-axis of FIG. 19 is the ratio pEGFP-N1/(Pro)$_3$-Glu(NHC$_{16}$H$_{33}$)$_2$ (Mbp/M); the Y-axis is percent of bound pEGFP. The data obtained demonstrate very efficient pEGFP-N1 binding to the HARMs. This data also allowed estimation of the maximum pEGFP-N1/(Pro)$_3$-Glu(NHC$_{16}$H$_{33}$)$_2$ ratio to be about 1 DNA base pair per 4 lipopeptide molecules. Furthermore, unlike liposomes formed from typical cationic lipid transfection reagents, HARMs formed from (Pro)$_3$-Glu(NHC$_{16}$H$_{33}$)$_2$ do not change their morphology after up to 2 weeks of co-incubation with DNA at room temperature.

EXAMPLE 21

This example further evaluates the protective effect of HARMs on DNA. Complexes made by the methods described above in Example 20 were made. The complexes were then exposed to 10 Kunitz units of DNase I in the presence of 5 mM MgCl$_2$ for 5 min, 30 min and 2 hours. Each sample contained 0.5 µg of pEGFP-N1 as measured by A$_{260}$ of aliquots of samples washed by centrifugation. Enzymatic degradation was stopped by addition of EDTA to 10 mM and freezing in dry ice. DNA was precipitated by adding absolute ethanol to 70% and washing with absolute ethanol. Re-dissolved samples were subjected to electrophoresis on 1% agarose gel. The gels were stained in a 50 µg/ml solution of ethidium bromide and photographed while transilluminated 350 nm. The electrophoresis gel (lanes 4–9) confirm formation of of DNA/surfactant complexes, in both detergent dialysis and cooincubation, and shows that incorporating pEGFP-N1 into Pro$_3$-GADH HARMs does not affect the integrity of the pEGFP-N1. And, incorporating pEGFP-N1 into HARMs provides at least partial protection of the DNA from DNase I.

EXAMPLE 22

This example concerns transfection of FVB mice with pEGFP-N1/(Pro)$_3$-Glu(NHC$_{16}$H$_{33}$)$_2$ HARMs. These pEGFP-N1/lipopeptide HARMs were synthesized in a manner similar to that of Example 21.

A number of mice (Table 5) received IV injections of p-GFP-N1/lipopeptide complex obtained by detergent dialysis (see above). Each mouse received 25 µg of DNA, 125 µg of lipopeptide in 50 µl of HBS per injection to each upper thigh. Empty HARM suspensions and pEGFP-N1 in HBS, pH 7.4, were used as controls. After 5–8 hours, 24 hours, 3 days, 1 week, and 2 weeks post-injection, 3 animals from each group were sacrificed. Their muscles were removed, and fixed for microscopy by known procedures.

The samples obtained were studied using a fluorescent microscope (Carl Zeiss, Thornwood, N.Y.) equipped with a FITC fluorescence filter (illumination 450–490 nm, emission >510 nm). The images were acquired using a CCD video camera with fixed gain. The fluorescence intensity was measured using image processing software, NIH Image 1.61.

None of the mice tested died or demonstrated any type of health abnormality before sacrifice. There were no consistent changes in body weight throughout the study. These data demonstrate that the complexes are not acutely toxic. But, to date fluorescence intensities of control samples were very high, which did not allow detection of EGFP expression.

TABLE 5

| Group | Number of Rodents | Type of Rodent | Strain | Sample |
|---|---|---|---|---|
| 1 | 15 | Mouse | FVB | HARM-encapsulated pEGFP-N1 |
| 2 | 15 | Mouse | FVB | HARMS Without the Plasmid |
| 3 | 15 | Mouse | FVB | pEGFP-N1 Without the HARMS |

EXAMPLE 23

This example concerns the preparation of pCX1 lipopeptides. The plasmid, pcDNA3HumHer2 Neu(pCX1), encodes HER-2/neu. HER-2/neu is a highly specific breast cancer protein, which can be used to develop a vaccine for treating and preventing breast cancer.

First, the plasmid pCXI (Corixa, Seattle, Wash.) was propagated in XLI *E. coli* (Stratagene, La Jolla, Calif.) according to known methods (for example, see Chapter 1, J. Sambrook et al., MOLECULAR CLONING, 2nd ed., 1989). Briefly, 100 µl of competent XLI bacteria were transformed with 0.4 µl of 2.3 mg/ml pCX1 in TE (10 mM Tris-HCl, 1 mM EDTA, pH 8) by heat shock. The transformed cells were plated onto selective media and one of the resulting colonies was selected and used to inoculate LB medium containing 100 µg/ml ampicillin. The plasmid was isolated using Plasmid Purification Giga Kit (Qiagen, Santa Clarita, Calif.) and its structure verified. XbaI (MBI Ferments, Amherst, N.Y., digestion produced two fragments identical to the original pCX1.

Next, micellar solutions of lipopeptides were prepared. 1.5 ml aliqouts containing 40 µM OG in HBS at pH 7.4 were added to 1.4×10$^{-6}$ moles of either (Pro)$_3$-Glu (NHC$_{12}$H$_{25}$)$_2$ Tabel 2, Kyujin et al., supra, or (Pro)$_3$-Glu (NHC$_{16}$H$_{33}$)$_2$. The mixtures were incubated at 60° C. for 5 minutes then cooled to room temperature. 0.3 ml aliquots of 1.2 mg/ml pCX1 in TE buffer were added to 1.5 ml of each lipopeptide micellar solution while vortexing.

Controls were also prepared and used. A first control, (Pro)$_3$-Glu(NHC$_{12}$H$_{25}$)$_2$ containing no plasmid, was formed by substituting TE buffer for the pCX1 solution. Another control sample, "no lipopeptide control", consisted of 300 µl of 1.2 mg/ml pure pCX1 in TE.

All samples, including the controls, were dialyzed against one liter of HBS over two days at room temperature with three changes. The dialyzed samples, except "no lipopeptide control", were centrifuged at 2300× g for 40 minutes at room temperature. The pellets obtained were resuspended in 400 µl of HBS. The volume of dialyzed pure pCX1 sample was adjusted to 400 µl. Aliquots of each preparation obtained were diluted to a final volume of 0.5 ml with HBS and mixed with 1.5 ml of 2% SDS (sodium dodecyl sulfate) in HBS. The aliquots were handled using 1 cc syringes with 28 gauge needles (the same size syringe used for injections in animal experiments). DNA concentrations in the resultant samples were estimated by $A_{260}$ in 1×1 quartz cuvette.

Table 6 provides the concentration of DNA in pCX1/lipopeptide complexes as determined by optical density at 260 nm.

TABLE 6

| Preparation | Vol. used (µl) | $A_{260}$ | DNA Concentration in the Preparation (mg/ml) |
|---|---|---|---|
| pCX1/(Pro)$_3$Glu(NHC$_{12}$H$_{25}$)$_2$ | | | |
| preparation | 50 | 0.35 | 0.75 |
| supernatant | 500 | 0.02 | 0.004 |
| pCX1/(Pro)$_3$Glu(NHC$_{16}$H$_{33}$)$_2$ | | | |
| preparation | 50 | 0.41 | 0.86 |
| supernatant | 500 | 0.01 | 0.002 |
| Dialyzed pCX1 | 50 | 0.45 | 0.95 |
| pCX1/(Pro)$_3$Glu(NHC$_{12}$H$_{25}$)$_2$ | 50 | 0.02 | N/A |
| pCX1/(Pro)$_3$Glu(NHC$_{16}$H$_{33}$)$_2$ | 50 | 0.02 | N/A |

As shown by Table 6, the supernatants obtained after centrifugation of pCX1/(Pro)$_3$-Glu (NHC$_{12}$H$_{25}$)$_2$ and pCX1/(Pro)$_3$-Glu (NHC$_{16}$H$_{33}$)$_2$ complexes have very low DNA concentrations. This indicates that DNA was incorporated into the lipopeptide complexes in both cases with close to 100% efficiency. However, the concentration of DNA in the pCX1/(Pro)$_3$-Glu(NHC$_{12}$H$_{25}$)2 preparation itself was slightly lower than 0.9 mg/ml (100% yield), which may reflect some loss during sample handling (using a syringe) rather than the efficiency of incorporation. Such a loss is easy to explain by the relatively large size of the complexes (see, for example, FIG. 20). Still, the data show that the loss in syringes is minimal, suggesting that the preparations may be administered to animals with acceptable accuracy.

Figure 20:
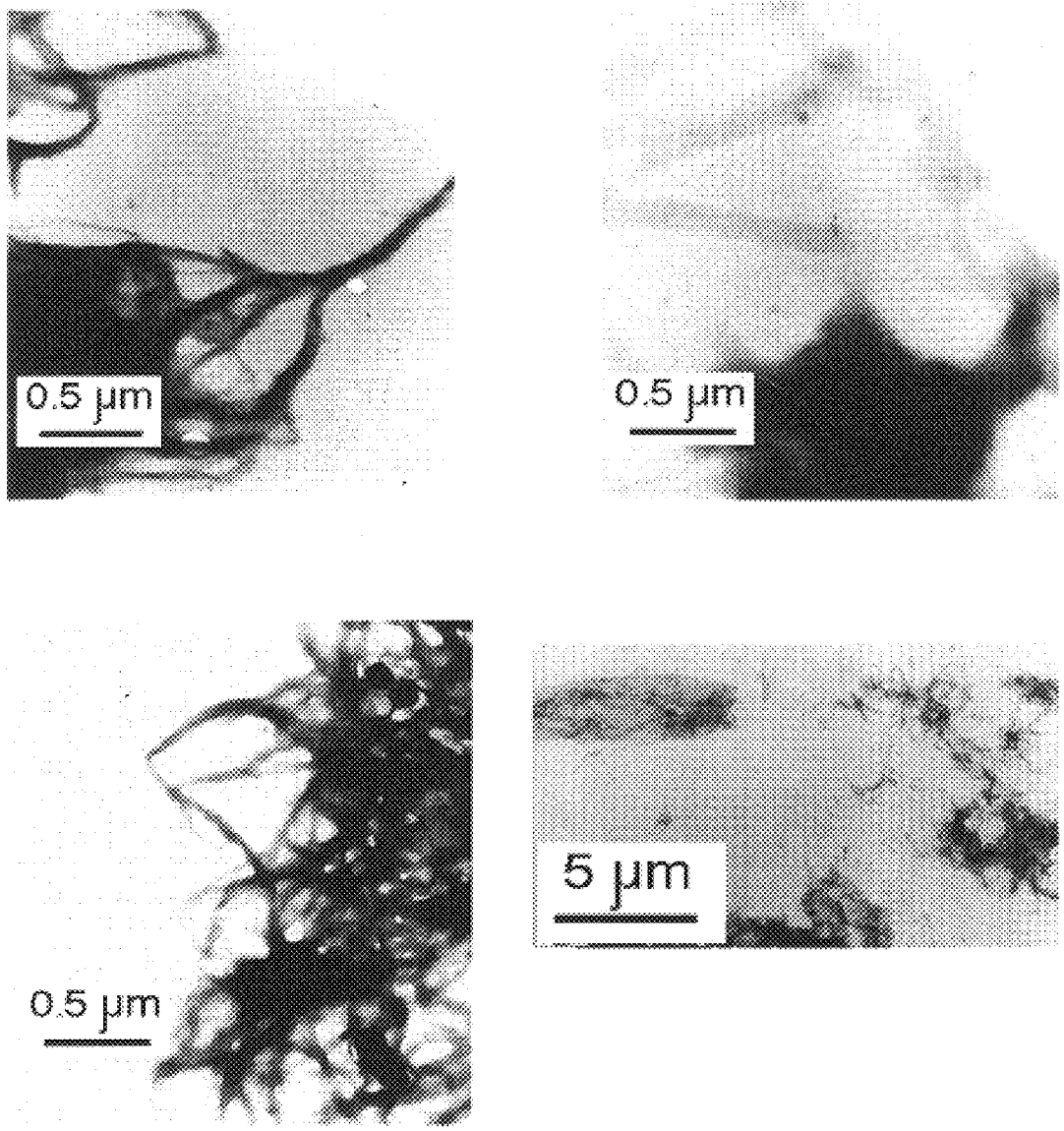
FIG. 20 is a TEM image of HARM complexes comprising pCX1 and glutamic acid dialkyl amides.

To confirm that the produced pCX1/lipopeptides formed HARMs, TEM images of samples were obtained. Aliquots of each sample (20 µl) were applied to Formvar-coated 150 mesh copper TEM sample grids. No stain was used. Samples were dried in air for at least 24 hours before observation with a Phillips EM 410 transmission electron microscope. As shown in FIG. 20, HARMs were observed in pCX1/glutamic acid dialkyl amide complexes. Lipopeptides prepared in the absence of pCX1 also were examined with TEM. Interestingly, (Pro)$_3$-Glu(NHC$_{12}$H$_{25}$)$_2$ formed HARMs with lower yield and different. morphology from pCX1/lipopeptide complexes, while (Pro)$_3$-Glu(NHC$_{16}$H$_{33}$)$_2$ formed no HARMs.

EXAMPLE 24

This example concerns the generation of a humoral immune response against HER-2/neu in HER2 transgenic mice injected with the pCX1/lipopeptides described in Example 23. HER2 transgenic mice, FVB/N-TgN (MMTVneu) 202 (Jackson Lab, Bartlaubou, Me.), carry the non-transforming rat neu gene on an MMTV (mouse mammary tumor virus) promotor. Mice with this gene develop breast cancer, histologically similar to human breast cancer, 100–200 days after birth. This breast cancer in the transgenic mice is mediated by rat neu overexpression. Thus, HER2 is a nonmutated tumor antigen in these animals. The ability to immunize animals to HER2 should demonstrate the ability to immunize patients whose tumors overexpress HER2.

HER2 transgenic mice were immunized (8–12 wks) with preparations (described in Example 23) containing 45 Ag of pCX1/lipopeptides, pCX1 alone or (Pro)$_3$-Glu(NHC$_{12}$H$_{25}$)$_2$ alone, in 50 µl of HBS. Injections were administered intermuscularly (IM) or interdermally (ID). Immunized mice were sacrificed 30-days post injection and their sera were analyzed by ELISA for the presence of antibodies against HER2. Indirect ELISA was performed in 96-well plates, Immuon 4 (DynexTech, Chanthy, Va.). The wells were coated with recombinant human HER2 protein (Corixa, Seattle, Wash.) overnight at room temperature. Carbonate buffer (50 mM Na-carbonate pH 9.5) containing no protein was used as a control. After blocking with PBS-20 mM Na-phosphate, 140 mM NaCl pH 7.4 and washing with PBS 10/050 Tween 1% BSA for one hour, the mouse sera were added at dilutions of 1:100, 1:200, 1:400, and 1:800. The plates were incubated for one hour at room temperature and washed with PBS/0.50 Tween. The secondary antibody goat-anti-mouse-IgG conjugated to horseradish peroxidase (Zymed, San Francisco, Calif.) diluted 1:5000 in PBS/0.5% Tween was added to the wells, incubated for 45 minutes at room temperature, then washed three times with PBS/0.5% Tween. TMB developing reagent (Kirkeyaard and Perry Laboratories, Gaithersburg, Md.) was added.

Figure 21:
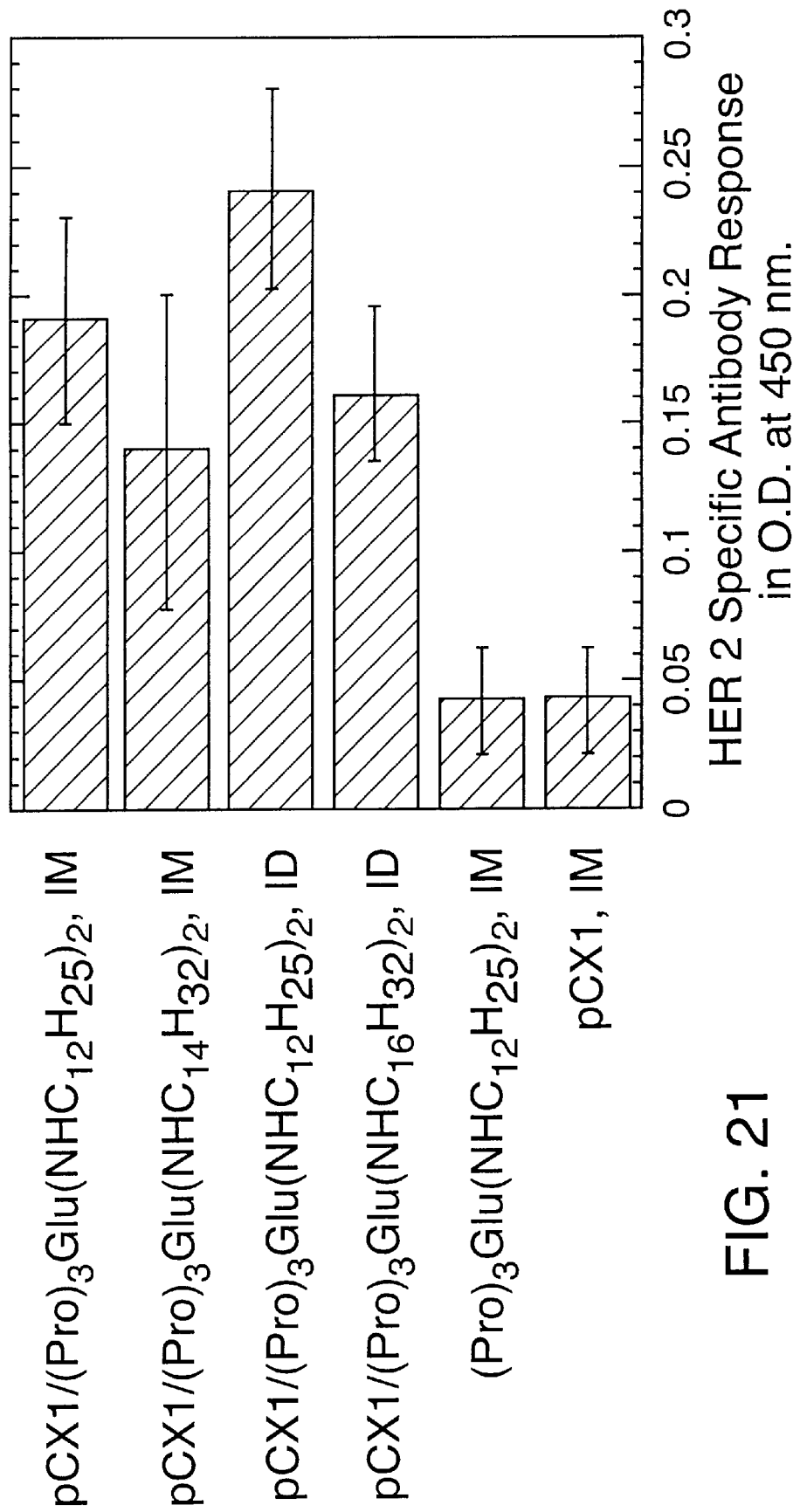
FIG. 21 is a graph illustrating HER 2 specific antibody responses to various samples by optical density at 450 nm.

After the wells developed colors (5–10 min at room temperature), OD values were read at 450 nm. As shown in FIG. 21, mice immunized with either of the two pCX1/lipopeptides, administered either IM or ID, generated a significant humoral immune response. This is indicated by the significant generation of antibodies against HER2. In contrast, neither the plasmid (pCX1) nor the lipoprotein alone generated an immune response.

Therefore, the pCX1 plasmid alone cannot generate a significant immune response against HER2, if only administered once. This could be due to the short survival time of the plasmid in vivo, since it was not protected from nucleases. In addition, the lipopeptide itself was also unable to generate specific immune response. This is advantageous since it would be detrimental to a patient if they developed an immune response to the lipopeptide. Importantly, this data demonstrates that an immune response can be generated to the HER2 protein if the pCX1 plasmid is administered as coupled to or associated with HARMs. The HARMs protect the DNA from degradation by nucleases, thus allowing for expression of the DNA for a long enough period to generate an immune response.

The present invention has been described in accordance with preferred embodiments. However, it will be understood that certain substitutions and alterations may be made thereto without departing from the spirit and scope of the invention.

We claim:

1. A complex self assembled into high axial ratio microstructures, the complex satisfying the formula HARM-Lg, where HARM is a high axial ratio microstructure forming material and Lg is a ligand noncovalently associated with the high axial ratio microstructure forming material, the HARM comprising less than 50 mole percent of a negatively charmed high axial ratio microstructure forming material.

2. The complex according to claim 1 where the HARM is selected from the group consisting of tubules, cochleate cylinders, helical ribbons, twisted ribbons, and mixtures thereof.

3. The complex according to claim 1 Inhere the Lg is a therapeutic.

4. The complex according to claim 1 and further comprising a therapeutic covalently bonded to the complex.

5. The complex according to claim 1 and further comprisng a therapeutic entrapped in the lumen of the HARM.

6. The complex according to claim 1 where the high axial ratio microstructure forming material is selected from the group consisting of $DC_{8,9}PC$, NFA-Galactocerebroside, HFA-Galactocerebroside, $NH_2$-Glu-(NH–$C_{12}H_{25}$)$_2$, $NH_2$-Pro-Glu-(NH—$C_{12}H_{25}$)$_2$, $NH_2$-Gly-Lys-Sar-Pro-Glu-(NH—$C_{12}H_{25}$)$_2$, NAcPro-ceramide, $NH_2$-Glu-(NH—$C_{14}H_{29}$)$_2$, N-hexanoyl ceramide, N-heptanoyl ceramide, N-octanoyl ceramide, psychosine, N-decanoyl ceramide, N-myristoyl ceramide, N-palmitoyl ceramide, N-oleoyl ceramide, N-stearoyl ceramide, N-palmitoyl-1-O-allyl ceramide, N-palmitoyl-3-O-allyl-ceramide, $NH_2$-Glu-(NH—$C_{16}H_{33}$)$_2$, N-nervonoyl ceramide, N-nervonoyl-(1,3-formyl acetal) ceramide, N-nervonoyl-3-oxo ceramide, N-nervonoyl-1-amino ceramide, N-octanoyl-11-1-O-triphenylmethyl ceramide, N-nervonoyl-1-O-allyl ceramide, N-nervonoyl-3-O-allyl ceramide, N-nervonoyl-3-O-methoxymethyl ceramide, N-palmitoyl galactocerebroside, N-nervonoyl-(1,3-(3-hydroxy)-propyl acetal) ceramide, N-oleoyl galactocerbroside, N-nervonoyl-1-O-mesyl ceramide, N-stearoyl galactocerebroside, N-nervonoyl-(1,3-hexyl acetal) ceramide, NAcGly-ceramide, N-nervonoyl-1-phthalimido ceramide, Pro-Pro-Pro-Glu-($NHC_{12}H_{25}$)$_2$ 1, N-palmitoyl-1-O-triphenylmethyl ceramide, N-nervonoyl-1-O-tosyl ceramide, N-nervonoyl-1-(2-napthoic acid)-ceramide, N-nervonoyl galactocerebroside, Pro-Pro-Pro-Glu-($NHC_{12}H_{25}$)$_2$, N-nervonoyl-1-(coumarin-3-CO2H) ceramide, N-nervonoyl-1-O-tertbutyldiphenylsilyl ceramide, Pro-Pro-Pro-Glu-($NHC_{12}H_{25}$)$_2$, K-A-Ser-P-Glu-($NHC_{12}H_{25}$)$_2$, N-nervonoyl-1-O-triphenylmethyl-3-methoxymethyl-ceramide, N-nervonoyl-1-O-trityl ceramide, Gly-Lys-(e!-Z)-Ser-Pro-Glu-($NHC_{12}H_{25}$)$_2$, Ac-GRAGGAAPPP-E-($NHC_{14}H_{29}$)$_2$, and mixtures thereof.

7. The complex according to claim 3 where the therapeutic is a nucleic acid.

8. The complex according to claim 7 wherein the nucleic acid is nuclear or plasmid DNA.

9. The complex according to claim 3 where the high axial ratio microstructure forming material is selected from the group consisting of amino-acid based amphiphiles, phospholipid-based amphphiles, sphingosine-based amphiphiles, aldonamide-based amphiphiles, and mixtures thereof.

10. The complex according to claim 9 where the amino-acid based amphiphiles satisfy the formula 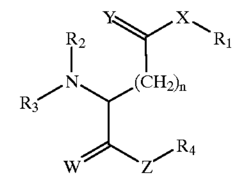 where n=1–10, $R_1$ is an aromatic ring or rings, or an aliphatic organic or heteroaliphatic organic chain having from about 1–30 atoms, 0–6 sites of unsaturation and 0–6 heteroatoms, $R_2$ is H, $R_1$ or $R_4$, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, W is O or S, X is O, S, NH, $NR_1$ $NR_3$ or $NR_4$ Y is O or S, and Z is O, S, NH or $NR_1$.

11. The complex according to claim 9 where the phospholipid-based amphiphiles satisfy the formula 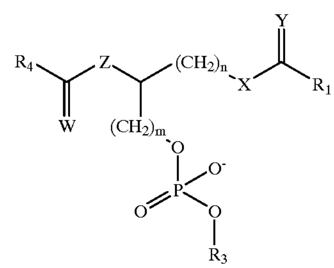 where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_3$ is a functional group that allows noncovalent bonding of LS, to HARM, $R_4$ is an aromatic ring or rings, or an aliphatic organic or heteroaliphatic organic chain having from about 1–30 atoms, 0–6 sites of unsaturation and 0–6 heteroatoms, W is O or S, X is O, S, NH, $NR_1$, $NR_3$ or $NR_4$, Y is O or S, and Z is O, S, NH or $NR_1$.

12. The complex according to claim 9 where the sphingosine-based amphiphiles satisfy the formula where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, X is O, S, NH, $NR_1$, $NR_3$ or $NR_4$, and Y is O or S.

13. The complex according to claim 9 where the sphingosine-based amphiphiles satisfy the formula $$\text{R}_1\underset{Y}{\overset{O}{\diagdown}}\text{C}\overset{(CH_2)_m}{\diagdown}\text{CH}\overset{R_3}{\diagup}$$
$$\text{R}_4\underset{X}{\diagup}\text{C}\underset{(CH_2)_n}{\diagup}$$

where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, X

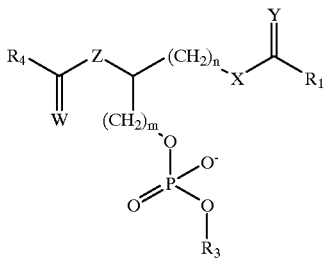

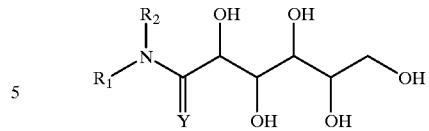

where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, W is O or S, X is O, S, NH, $NR_1$, $NR_3$ or $NR_4$, Y is O or S, and Z is O, S, NH or $NR_1$.

33. The complex according to claim 30 where the sphingosine-based amphiphiles satisfy the formula

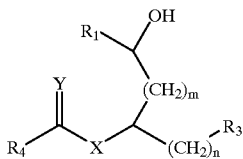

where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, X is O, S, NH, $NR_1$, $NR_3$ or $NR_4$, and Y is O or S.

34. The complex according to claim 30 where the sphingosine-based amphiphiles satisfy the formula

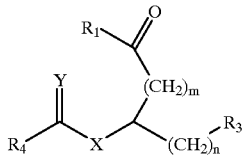

where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, X is O, S, NH, $NR_1$, $NR_3$ or $NR_4$, and Y is O or S.

35. The complex according to claim 30 where the aldonamide-based amphiphiles satisfy the formula where $R_1$ is an aromatic ring or rings, or an aliphatic organic or heteroaliphatic organic chain heaving from about 1–30 atoms, 0–6 sites of unsaturation and 0–6 heteroatoms, $R_2$ is H or $R_1$, and Y is O or S.

36. The method according to claim 29 where the high axial ratio microstructure forming material is a glutamic acid dialkyl amide.

37. The method according to claim 29 where the high axial ratio microstructure forming material is glutamic acid didodecyl amide or glutamic acid dihexadecyl amide.

38. The method according to claim 29 where the high axial ratio microstructure forming material is selected from the group consisting of $DC_{8,9}PC$, ceramides, cerebrosides, glutamate-based amphiphiles and glutamic acid dialkyl amides.

39. The method according to claim 23 where the nucleic acid is nuclear or plasmid DNA.

40. A method for delivering a therapeutic complex to an organism, comprising:
    providing a complex having a high axial ratio microstructure, the complex comprising nuclear or plasmid DNA noncovalently associated with a high axial ratio microstructure forming material, the high axial ratio microstructure forming material further comprising less than 50 mole percent of a negatively charged high axial ratio microstructure forming material; and
    administering an effective amount of the complex to the mammal.

41. The method according to claim 40 where the high axial ratio microstructure forming material is selected from the group consisting of glutamate-based amphiphiles, polyglutamate-based amphiphiles, $DC_{8,9}PC$, cerbreosides, ceramides, psychosine, analogs thereof, and mixtures thereof.

42. The method according to claim 40 where the high axial ratio microstructure forming material is selected from the group consisting of $DC_{8,9}PC$, NFA-Galactocerebroside, HFA-Galactocerebroside, $NH_2$-Glu-(NH—$C_{12}H_{25}$)$_2$, $NH_2$-Pro-Glu-(NH—$C_{12}H_{25}$)$_2$, $NH_2$-Gly-Lys-Sar-Pro-Glu-(NH—$C_{12}H_{25}$)$_2$, NAcPro-ceramide, $NH_2$-Glu-(NH—$C_{14}H_{29}$)$_2$, N-hexanoyl ceramide, N-heptanoyl ceramide, N-octanoyl ceramide, psychosine, N-decanoyl ceramide, N-myristoyl ceramide, N-palmitoyl ceramide, N-oleoyl ceramide, N-stearoyl ceramide, N-palmitoyl-1-O-allyl ceramide, N-palmitoyl-3-O-allyl-ceramide, $NH_2$-Glu-(NH—$C_{16}H_{33}$)$_2$, N-nervonoyl ceramide, N-nervonoyl-(1,3-formyl acetal) ceramide, N-nervonoyl-3-oxo ceramide, N-nervonoyl-1-amino ceramide, N-octanoyl-1-O-triphenylmethyl ceramide, N-nervonoyl-1-O-allyl ceramide, N-nervonoyl-3-O-allyl ceramide, N-nervonoly-3-O-methoxymethyl ceramide, N-palmitoyl galactocerebroside, N-nervonoyl-(1,3-(3-hydroxy)-propyl acetal) ceramide, N-oleoyl galactocerbroside, N-nervonoyl-1-O-mesyl ceramide, N-stearoyl galactocerebroside, N-nervonoyl-(1,3-hexyl acetal) ceramide, NAcGly-ceramide, N-nervonoyl-1-phthalimido ceramide, Pro-Pro-Pro-Glu-(NHC$_1$H$_{25}$)$_2$ 1, N-palmitoyl-1-O-triphenylmethyl ceramide, N-nervonoyl-1-O-tosyl ceramide, N-nervonoyl-1-(2-napthoic acid)- ceramide, N-nervonoyl galactocerebroside, Pro-Pro-Pro-Glu-$(NHC_{14}H_{29})_2$, N-nervonoyl-1-(coumarin-3-CO2H) ceramide, N-nervonoyl-1-O-tertbutyldiphenylsilyl ceramide, Pro-Pro-Pro-Glu-$(NHC_{16}H_{33})_2$, Lys-Ala-Sar-Pro-Glu—$(NHC_{12}H_{25})_2$, N-nervonoyl-1-O-triphenylmethyl-3-methoxymethyl-ceramide, N-nervonoyl-1-O-trityl ceramide, Gly-Lys-(e-Z)-Sar-Pro-Glu-$(NHC_{12}H_{28})_2$, II-Ac-Gly-Aug-Ala-$(Gly)_2$-$(Pro)_3$-Glu-$(NHC_{14}H_{29})$ 2, and mixtures thereof.

43. The method according to claim 40 where the high axial ratio microstructure forming material is a glutamic acid dialkyl amide.

44. The method according to claim 43 where the high axial ratio microstructure forming material is glutamic acid didodecyl amide or glutamic acid dihexadecyl amide.

45. The method according to claim 18 where the complex is a DNA vaccine.

46. The method according to claim 40 where the complex is a DNA vaccine.

47. The complex of claim 1 where the HARM has a neutral or positive net charge.

48. The method of claim 18 where the high axial ratio microstructure complex has a neutral or positive net charge.

49. A method for delivering a therapeutic to an organism, comprising:

forming a high axial ratio microstructure complex comprising a therapeutic noncovalently associated with a high axial ratio microstructure forming material in a solution or suspension comprising the high axial ratio microstructure and the ligand but excluding divalent cations while forming the complex; and administering an effective amount of the complex to the organism.

50. The method according to claim 49 where the therapeutic is a nucleic acid.

51. The method according to claim 49 where the high axial ratio forming material has a neutral or positive net charge.

52. The method according to claim 49 where the solution or suspension consists essentially of high axial ratio microstructure forming material, and a ligand noncovalently associated with the high axial ratio microstructure forming material.

53. A complex for providing substantially zero order or psuedo first order kinetics, comprising a positively charged HARM molecule and a negatively charged nucleic acid noncovalently associated with the HARM molecule.

54. The complex according to claim 53 where the nucleic acid is nuclear or plasmid DNA.

55. The complex of claim 53 where the HARM material comprises less than 50 mole percent of a negatively charged high axial microstructure forming material.

56. The complex of claim 53 where the complex has neutral or positive net charge.

57. The complex according to claim 53 and further comprising a therapeutic covalently bonded to the complex.

58. The complex according to claim 53 and further comprising a therapeutic entrapped in a lumen defined by the HARM.

59. The complex according to claim 53 where the high axial ratio microstructure forming material is selected from the group consisting of $DC_{8,9}PC$, NFA-Galactocerebroside, HFA-Galactocerebroside, $NH_2$-Glu-(NH—$C_{12}H_{25})_2$, $NH_2$-Pro-Glu-(NH—$C_{12}H_{25})_2$, $NH_2$-Gly-Lys-Ser-Pro-Glu-(NH—$C_{12}H_{25})_2$, NAcPro-ceramide, $NH_2$-Glu-(NH-$C_{14}H_{29})_2$, N-hexanoyl ceramide, N-heptanoyl ceramide, N-octanoyl ceramide, psychosine, N-decanoyl ceramide, N-myristoyl ceramide, N-palmitoyl ceramide, N-oleoyl ceramide, N-stearoyl ceramide, N-palmitoyl-1-O-allyl ceramide, N-palmitoyl-3-O-allyl-ceramide, $NH_2$-Glu-(NH—$C_{16}H_{33})_2$, N-nervonoyl ceramide, N-nervonoyl-(1,3-formyl acetal) ceramide, N-nervonoyl-3-oxo ceramide, N-nervonoyl-1-amino ceramide, N-octanoyl-1-O-triphenylmethyl ceramide, N-nervonoyl-1-O-allyl ceramide, N-nervonoyl-3-O-allyl ceramide, N-nervonyl-3-O-methoxymethyl ceramide, N-palmitoyl galactocerebroside, N-nervonoyl-(1,3-(3-hydroxy)-propyl acetal) ceramide, N-oleoyl galactocerbroside, N-nervonoyl-1-O-mesyl ceramide, N-stearoyl galactocerebroside, N-nervonoyl-(1,3-hexyl acetal) ceramide, NAcGly-ceramide, N-nervonoyl-1-phthalimido ceramide, Pro-Pro-Pro-Glu-$(NHC_{12}H_{25})_2$ 1, N-palmitoyl-1-O-triphenylmethyl ceramide, N-nervonoyl-1-O-tosyl ceramide, N-nervonoyl-1-(2-napthoic acid)-ceramide, N-nervonoyl galactocerebroside, Pro-Pro-Pro-Glu-$(NHC_{12}H_{25})_2$, N-nervonoyl-1-(coumarin-3-CO2H) ceramide, N-nervonoyl-1-O-tertbutyldiphenylsilyl ceramide, Pro-Pro-Pro-Glu-$(NHC_{12}H_{25})_2$, K-A-Ser-P-Glu-$(NHC_{12}H_{25})_2$, N-nervonoyl-1-O-triphenylmethyl-3-methoxymethyl-ceramide, N-nervonoyl-1-O-trityl ceramide, Gly-Lys-(e-Z)-Ser-Pro-Glu-$(NHC_{12}H_{25})_2$, Ac-GRAGGAAPPP-E-$(NHC_{14}H_{29})_2$, and mixtures thereof.

60. The complex according to claim 53 where the high axial ratio microstructure forming material is selected from the group consisting of amino-acid based amphiphiles, phospholipid-based amphiphiles, sphingosine-based amphiphiles, aldonamide-based amphiphiles, and mixtures thereof.

61. A complex self assembled into high axial ratio microstructures, the complex satisfying the formula HARM-Lg, where Lg is a ligand noncovalently associated with a high axial ratio microstructure forming material and HARM is a high axial ratio microstructure forming material selected from the group consisting of amino-acid based amphiphiles, phospholipid-based amphiphiles, sphingosine based amphiphiles, aldonamide-based amphiphiles, and mixtures thereof, the amino-acid based amphiphiles satisfying a formula 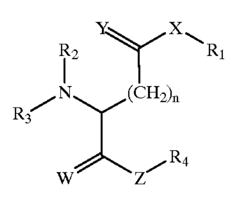 where n=1–10, $R_1$ is an aromatic ring or rings, or an aliphatic organic or heteroaliphatic organic chain having from about 1–30 atoms, 0–6 sites of unsaturation and 0–6 heteroatoms, $R_2$ is H, $R_1$ or $R_4$, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, W is O or S, X is O, S, NH, $NR_1$, $NR_3$ or $NR_4$, Y is O or S, and Z is O, S, NH or $NR_1$, the phospholipid-based amphiphiles satisfying the formula

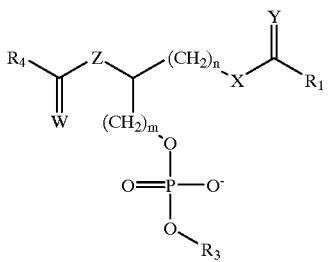

where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_3$ is a functional group that allows noncovalent bonding, of Lg to HARM, $R_4$ is an aromatic ring or rings, or an aliphatic organic or heteroaliphatic organic chain having from about 1–30 atoms, 0–6 sites of unsaturation and 0–6 heteroatoms, W is O or S, X is O, S, NH, NR, $NR_3$ or $NR_4$, Y is O or S, and Z is O, S, NH or $NR_1$, the sphingosine-based amphiphiles satisfying the formula or where n=1–10, m=1–10, $R_1$ is an aromatic ring or rings, or an aliphatic organic or heteroaliphatic organic chain having from about 1–30 atoms, 0–6 sites of unsaturation and 0–6 heteroatoms, $R_3$ is a functional group that allows noncovalent bonding of Lg to HARM, $R_4$ is an aromatic ring or rings, or an aliphatic organic or heteroaliphatic organic chain having from about 1–30 atoms, 0–6 sites of unsaturation and 0–6 heteroatoms, X is O, S, NH, $NR_1$, $NR_3$ or $NR_4$, and Y is O or S, and the aldonamide-based amphiphiles satisfying the formula where $R_1$ is an aromatic ring or rings, or an aliphatic organic or heteroaliphatic organic chain having from about 1–30 atoms, 0–6 sites of unsaturation and 0–6 heteroatoms, $R_2$ is H or $R_1$, and Y is O or S.

62. The complex according to claim 61 where the high axial ratio forming microstructure material comprises less than 50 mole percent of a negatively charged high axial ratio microstructure forming material.

63. The complex according to claim 62 where the high axial ratio forming microstructure material is a glutamic acid dialkyl amide.

64. The complex according to claim 63 wherein the high axial ratio microstructure forming material is a glutamic acid didodecyl amide or a glutamic acid dihexadecyl amide.

65. The complex according to claim 64 where the high axial ratio microstructure forming material is (Pro)3-Glu $(NHC_{16}H_{33})_2$.

66. A therapeutic delivery complex self assembled into high axial ratio microstructures, the complex satisfying t he formula HARM-Lg, where Lg is a ligand noncovalently associated with the high axial ratio microstructure forming material and the high axial ratio microstructure forming material is selected from the group consisting of $DC_{8,6}PC$, NFA-Galactocerebroside, HFA-Galactocerebroside, $NH_2$-Glu-$(NH—C_{12}H_{25})_2$, $NH_2$-Pro-Glu-$(NH—C_{12}H_{25})_2$, NH-Gly-Lys-Ser-Pro-Glu-$(NH—C_{12}H_{25})_2$, NAcPro-ceramide, $NH_2$-Glu-$(NH–C_{14}H_{29})_2$, N-hexanoyl ceramide, N-heptanoyl ceramide, N-octanoyl ceramide, psychosine, N-decanoyl ceramide, N-myristoyl ceramide, N-palmitoyl ceramide, N-oleoyl ceramide, N-stearoyl ceramide, N-palmitoyl-1-O-allyl ceramide, N-palmitoyl-3-O-allyl-ceramide, $NH_2$-Glu-$(NH–C_{16}H_{33})_2$, N-nervonoyl ceramide, N-nervonoyl-(1,3-formyl acetal) ceramide, N-nervonoyl-3-oxo ceramide, N-nervonoyl-1-amino ceramide, N-octanoyl-1-O-triphenylmethyl ceramide, N-nervonoyl-1-O-allyl ceramide, N-nervonoyl-3-O-allyl ceramide, N-nervonyl-3-O-methoxymethyl ceramide, N-palmitoyl galactocerebroside, N-nervonoyl-(1,3-(3-hydroxy)-propyl acetal) ceramide, N-oleoyl galactocerbroside, N-nervonoyl-1-O-mesyl ceramide, N-stearoyl galactocerebroside, N-nervonoyl-(1,3-hexyl acetal) ceramide, NAcGly-ceramide, N-nervonoyl-1-phthalimido ceramide, Pro-Pro-Pro-Glu-$(NHC_{12}H_{25})_2$ 1, N-palmitoyl-1-O-triphenylmethyl ceramide, N-nervonoyl-1-O-tosyl ceramide, N-nervonoyl-1-(2-napthoic acid)-ceramide, N-nervonoyl galactocerebroside, Pro-Pro-Pro-Glu-$(NHC_{12}H_{25})_2$, N-nervonoyl-1-(coumarin-3-CO2H) ceramide, N-nervonoyl-1-O-tertbutyldiphenylsilyl ceramide, Pro-Pro-Pro-Glu-$(NHC_{12}H_{25})_2$, K-A-Ser-P-Glu-$(NHC_{12}H_{25})_2$, N-nervonoyl-1-O-triphenylmethyl-3-methoxymethyl-ceramide, N-nervonoyl-1-O-trityl ceramide, Gly-Lys-(e-Z)-Ser-Pro-Glu-$(NHC_{12}H_{25})_2$, Ac-GRAGGAAPPP-E-$(NHC_{14}H_{29})_2$, and mixtures thereof.

67. The complex of claim 66 where the high axial ratio microstructure forming material has a net neutral or positive charge.

68. A complex self assembled into high axial ratio microstructures, the complex satisfying the formula HARM-Lg and having a neutral or positive net charge, where HARM is a high axial ratio microstructure forming material and Lg is a nucleic acid ligand noncovalently associated with the high axial ratio microstructure forming material.

69. The complex according to claim 68 further comprising a therapeutic entrapped in the lumen of the HARM.

70. The complex according to claim 68 where the high axial ratio microstructure forming material is selected from the group consisting of $DC_{8,9}PC$, NFA-Galactocerebroside, HFA-Galactocerebroside, $NH_2$-Glu-$(NH—C_{12}H_{25})_2$, $NH_2$-Pro-Glu-$(NH—C_{12}H_{25})_2$, $NH_2$-Gly-Lys-Ser-Pro-Glu-$(NH—C_{12}H_{25})_2$, NAcPro-ceramide, $NH_2$-Glu-$(NH—C_{14}H_{29})_2$, N-hexanoyl ceramide, N-heptanoyl ceramide, N-octanoyl ceramide, psychosine, N-decanoyl ceramide, N-myristoyl ceramide, N-palmitoyl ceramide, N-oleoyl ceramide, N-stearoyl ceramide, N-palmitoyl-1-O-allyl ceramide, N-palmitoyl-3-O—allyl-ceramide, $NH_2$-Glu-$(NH–C_{16}H_{33})_2$, N-nervonoyl ceramide, N-nervonoyl-(1,3-formyl acetal) ceramide, N-nervonoyl-3-oxo ceramide, N-nervonoyl-1-amino ceramide, N-octanoyl-1-O-triphenylmethyl ceramide, N-nervonoyl-1-O-allyl ceramide, N-nervonoyl-3-O-allyl ceramide, N-nervonyl-3-O-methoxymethyl ceramide, N-palmitoyl galactocerebroside, N-nervonoyl-(1,3-(3-hydroxy)-propyl acetal) ceramide, N-oleoyl galactocerbroside, N-nervonoyl-1-O-mesyl ceramide, N-stearoyl galactocerebroside, N-nervonoyl-(1,3-hexyl acetal) ceramide, NAcGly-ceramide, N-nervonoyl-1-phthalimido ceramide, Pro-Pro-Pro-Glu-(NHC$_{12}$H$_{25}$)$_2$ 1, N-palmitoyl-1-O-triphenylmethyl ceramide, N-nervonoyl-1-O-tosyl ceramide, N-nervonoyl-1-(2-napthoic acid)-ceramide, N-nervonoyl galactocerebroside, Pro-Pro-Pro-Glu-(NHC$_{12}$H$_{25}$)$_2$, N-nervonoyl-1-(coumarin-3-CO2H) ceramide, N-nervonoyl-1-O-tertbutyldiphenylsilyl ceramide, Pro-Pro-Pro-Glu-(NHC$_{12}$H$_{25}$)$_2$, K-A-Ser-P-Glu-(NHC$_{12}$H$_{25}$)$_2$, N-nervonoyl-1-O-triphenylmethyl-3-methoxymethyl-ceramide, N-nervonoyl-1-O-trityl ceramide, Gly-Lys-(e-Z)-Ser-Pro-Glu-(NHC$_{12}$H$_{25}$)$_2$, Ac-GRA(GGAAPPP-E-(NHC$_{14}$H$_{29}$)$_2$, and mixtures thereof.

71. The complex according to claim 68 wherein the nucleic a,-id is nuclear or plasmid DNA.

* * * * *

UNITED STATES PATENT AND TRADEMARK OFFICE
CERTIFICATE OF CORRECTION

PATENT NO. : 6,180,114 B1
DATED : January 30, 2001
INVENTOR(S) : Yager et al.

It is certified that error appears in the above-identified patent and that said Letters Patent is hereby corrected as shown below:

Title page,
Item [57], ABSTRACT
Line 10, change "oranisms", to -- organisms --.

Column 3,
Line 32, "bee(n observed" should be -- been observed --.
Line 58, "phopholipids," should be -- phospholipids, --.

Column 4,
Line 46, "*he" should be -- the --.

Column 5,
Line 3, "Ligands" should be -- ligands --.
Line 36, "microsrtucture" should be -- microstructure --.
Line 38, "micrstructure" should be -- microstructure --.
Line 45, "amphphiles" should be -- amphiphiles --.

Column 7,
Line 47, "$DC_{8,9PC}$" should be -- $DC_{8,9}PC$ --.
Line 52, "$H_{33}$)" should be -- $H_{33})_2$. --.
Line 56, "-Glu" should be -- Glu --.

Column 11,
Line 42, "compound s" should be -- compounds --.
Line 52, "gee," should be -- See, --.

Column 12,
Line 60, "form" should be -- forming --.
Line 62, "HFA-GAL-Cer." should be -- HFA-GAL-cer. --.

Column 18,
Line 48, "below. formula for" should be -- below. --.

Column 29,
Line 22, "$_2$/Pro" should be -- $_2$, P --.
Line 22, ") $_2$" should be -- )$_2$ --.
Line 48, "$_2$ and" should be -- $_2$, and --.

Column 30,
Line 32, "eg" should be -- e.g. --.
Line 39, "hixh" should be -- high --.

UNITED STATES PATENT AND TRADEMARK OFFICE
CERTIFICATE OF CORRECTION

PATENT NO. : 6,180,114 B1
DATED : January 30, 2001
INVENTOR(S) : Yager et al.

It is certified that error appears in the above-identified patent and that said Letters Patent is hereby corrected as shown below:

Column 31,
Line 43, "HA?MS" should be -- HARMS --.

Column 32,
Lines 52 and 67, "a-amino" should be -- α-amino --.

Column 33,
Line 65, "HTR-forming" should be -- HAR-forming --.

Column 35,
Line 16, "Galactocerebrcsides" should be -- Galactocerebrosides --.
Line 49, "school" should be -- School --.

Column 36,
Line 3, "physiolgocial" should be -- physiological --.
Line 17, "Cylinder" should be -- cylinder --.

Column 37,
Line 17, "180" should be -- 18% --.
Line 65, "multi lamellar $DC_{8,8}PC$" should be -- multilamellar $DC_{8,9}PC$ --.

Column 38,
Line 7, "other" should be -- outer --.
Line 18, "that" should be -- than --.
Line 55, "2. Detergent Dissolution Kinetics Bile" should be
-- 2. Detergent Dissolution Kinetics
     Bile --.
Line 57, "is; a" should be -- is a --.
Line 65, "multi-lamellar" should be -- multilamellar --.

Column 39,
Line 10, "c)r" should be -- or --.
Line 63, "$DC_{89}PC$" should be -- $DC_{8,9}PC$ --.

Column 40,
Lines 5-6, "self-assembly" should be -- self-assemble --.
Line 7, "vesices" should be -- vesicles --.
Line 34, ":n" should be -- in --.

UNITED STATES PATENT AND TRADEMARK OFFICE
CERTIFICATE OF CORRECTION

PATENT NO. : 6,180,114 B1
DATED : January 30, 2001
INVENTOR(S) : Yager et al.

It is certified that error appears in the above-identified patent and that said Letters Patent is hereby corrected as shown below:

<u>Column 41,</u>
Line 33, "Glu] Pro$_3$" should be -- Glu]. Pro$_3$ --.
Line 56, "Histopatholigcal" should be -- Histopathological --.
Line 60, "negatives" should be -- negative --.

<u>Column 42,</u>
Line 24, "gnerally" should be -- generally --.
Line 30, "Al" should be -- All --.
Line 46, "1k" should be -- 1% --.
Line 52, "thee" should be -- the --.
Lines 57 and 60, "0C" should be -- 0°C --.
Line 63, "tc" should be -- to --.
Line 67, "NaHCO3" should be -- NaHCO$_3$, --.

<u>Column 43,</u>
Line 14, "twenty fours." should be -- twenty four hours. --.
Line 52, "N-dimethylforriamide" should be -- N-dimethyformamide --.
Line 56, "0C." should be -- 0°C. --.
Line 58, "microlitters" should be -- microliters --.

<u>Column 44,</u>
Line 2, "HC1,'dioxane" should be -- HC1/dioxane --.
Line 20, "DCC)." should be -- DCC. --.
Line 39, "Nu" should be -- Nα --.
Lines 50 and 52, "H$_2$C" should be -- H$_2$O --.
Line 53, "Ná" should be -- Nα --.
Line 53, "Nù" should be -- Nω --.
Line 56, "2:2.8" should be -- 22.8 --.

<u>Column 45,</u>
Line 13, "alany" should be -- alanyl --.
Line 14, "-(glutamide" should be -- -glutamide --.
Line 22, "TFT" should be -- TFA --.
Line 27, "0.27 ES-MS" should be -- 0.27. ES-MS --.
Line 38, "di carbonate" should be -- dicarbonate --.

UNITED STATES PATENT AND TRADEMARK OFFICE
CERTIFICATE OF CORRECTION

PATENT NO. : 6,180,114 B1
DATED : January 30, 2001
INVENTOR(S) : Yager et al.

It is certified that error appears in the above-identified patent and that said Letters Patent is hereby corrected as shown below:

Column 47,
Line 6, "Rf" should be -- $R_f$ --.
Line 15, "2D7.0" should be -- 207.0 --.
Line 16, "and; stirred" should be -- and stirred --.
Line 18, "MeOh" should be -- MeOH --.
Line 43, "-o-" should be -- -O- --.
Line 44, "[butylsilyl]" should be -- butylsilyl] --.
Line 46, "mmol)." should be -- mmol), --.
Line 65, "[(diphenyl" should be -- [diphenyl --.

Column 48,
Line 5, "0.0:34" should be -- 0.034 --.
Line 5, "Rf" should be -- $R_f$ --.
Line 7, "5.3:3" should be -- 5.33 --.
Line 10, "1.8f" should be -- 1.86 --.
Line 16, "butylsilyh" should be -- butylsilyl --.
Line 24, "-1O-" should be -- -1-O- --.
Line 63, "Ch$_3$" should be -- $CH_3$ --.

Column 49,
Line 3, "Rf" should be -- $R_f$ --.
Line 36, "15.5)," should be -- 15.5Hz), --.

Column 50,
Line 11, "EL" should be -- a --.
Line 13, "990C" should be -- 99°C --.
Line 21, "MeOH were" should be -- MeOH and were --.
Line 28, "particles; were" should be -- particles were --.
Line 33, "particles," should be -- particles --.
Line 42, "HAIM's" should be -- HARMs --.
Line 56, "H$_{25}$)$_2$" should be -- $H_{25})_2$. --.

Column 51,
Line 11, "at." should be -- at --.
Line 38, "that injection" should be -- that after injection --.
Line 48, "qlutamide" should be -- glutamide --.

UNITED STATES PATENT AND TRADEMARK OFFICE
CERTIFICATE OF CORRECTION

PATENT NO. : 6,180,114 B1
DATED : January 30, 2001
INVENTOR(S) : Yager et al.

It is certified that error appears in the above-identified patent and that said Letters Patent is hereby corrected as shown below:

Column 52,
Line 27, "above)." should be -- above. --.
Line 34, "Mhz" should be -- MHz --.
Line 34, "buffers, listed" should be -- buffers listed --.

Column 53,
Line 2, "results;" should be -- results --.
Line 14, "° Carl" should be -- (Carl --.
Line 26, "HEBS" should be -- HBS --.
Line 27, "aliquouts" should be -- aliquots --.
Line 33, "(Pro)3-Glue(NHC$_{16}$H$_{33}$)2" should be -- (Pro)$_3$-Glu(NHC$_{16}$H$_{33}$)$_2$ --.
Lines 47 and 49, "(NHC$_1$6H$_{33}$)$_2$" should be -- (NHC$_{16}$H$_{33}$)$_2$ --.
Line 63, "ir" should be -- in --.

Column 54,
Lines 2, 3, 42 and 43, "(Pro$_3$)-Glu($_{16}$H$_{33}$)$_2$" should be -- (Pro)$_3$-Glu(NHC$_{16}$H$_{33}$)$_2$ --.
Line 23, "degration" should be -- degradation --.
Line 24, "A1" should be -- $\mu$1 --.
Line 35, "succesively" should be -- successively --.
Line 48, "HARMS" should be -- HARMs --.
Line 53, "DNA," should be -- DNA --.
Line 60, "Palo, Alto, Calif.)" should be -- Palo Alto, Calif.). --.
Line 67, "manufacture's" should be -- manufacturer's --.

Column 55,
Line 10, "H$_{33}$)2" should be -- H$_{33}$)$_2$ --.
Line 20, "PEGFP-NI were separated. by" should be -- pEGFP-NI were separated by --.
Line 54, "of of" should be -- of --.
Line 55, "cooincubation," should be -- co-incubation, --.
Line 67, "p-GFP-N1" should be -- pEGFP-N1 --.

Column 56,
Line 44, "pCXI" should be -- pCX1 --.
Line 55, "N.Y.," should be -- N.Y.) --.
Line 61, "Tabel" should be -- Table --.

Column 57,
Line 43, "H$_{25}$)2" should be -- H$_{25}$)$_2$ --.
Line 61, "different." should be -- different --.

UNITED STATES PATENT AND TRADEMARK OFFICE
CERTIFICATE OF CORRECTION

PATENT NO.   : 6,180,114 B1
DATED        : January 30, 2001
INVENTOR(S)  : Yager et al.

It is certified that error appears in the above-identified patent and that said Letters Patent is hereby corrected as shown below:

Column 58,
Line 14, "45 Ag" should be -- 45 $\mu$g --.
Line 28, "10/050" should be -- 10/0.5% --.
Line 31, "PBS/0.05" should be -- PBS/0.5% --.

Column 59,
Line 8, "charmed" should be -- charged --.
Line 15, "Inhere" should be -- where --.
Lines 20-21, "comprisng" should be -- comprising --.
Line 36, "N-octanoyl-11-1-O-" should be -- N-octanoyl-1-O- --.
Line 53, "e!" should be -- e --.
Line 63, "amphphiles" should be -- amphiphiles --.

Column 60,
Line 19, "Nr$_4$ Y" should be -- NR$_4$, Y --.
Line 40, "LS," should be -- Lg --.

Column 62,
Lines 19-20, "-1-triphenylmethyl" should be -- -1-O-triphenylmethyl --.
Line 27, "Gly" should be -- Glu --.
Line 42, "amphphiles" should be -- amphiphiles --.

Column 64,
Line 41, "cerbreosides" should be -- cerebrosides --.
Line 59, "nervonoly" should be -- nervonoyl --.
Line 62, "galactocerbroside" should be -- galactocerebroside --.

Column 65,
Line 7, "H28" should be -- H25 --.
Line 8, "H$_{29}$) 2" should be -- H$_{29}$)$_2$ --.

Column 66,
Line 12, "galactocerbroside" should be -- galactocerebroside --.

Column 67,
Line 20, "NR," should be -- NR$_1$, --.

UNITED STATES PATENT AND TRADEMARK OFFICE
CERTIFICATE OF CORRECTION

PATENT NO. : 6,180,114 B1
DATED : January 30, 2001
INVENTOR(S) : Yager et al.

It is certified that error appears in the above-identified patent and that said Letters Patent is hereby corrected as shown below:

Column 68,
Line 2, "(Pro)3" should be -- $(Pro)_3$ --.
Line 5, "t he" should be -- the --.
Line 9, "$DC_{8,6}PC$," should be -- $DC_{8,9}PC$ --.
Line 12, "NH" should be -- $NH_2$ --.
Line 25, "galactocerbroside" should be -- galactocerebroside --.

Column 69,
Line 2, "galactocerbroside" should be -- galactocerebroside --.

Column 70,
Line 5, "GRA(GGAAPPP" should be -- GRAGGAAPPP --.
Line 8, "a,-id" should be -- acid --.

Signed and Sealed this

Tenth Day of February, 2004

JON W. DUDAS
*Acting Director of the United States Patent and Trademark Office*